(12) United States Patent
Zhu et al.

(10) Patent No.: US 11,649,441 B2
(45) Date of Patent: *May 16, 2023

(54) TAQ DNA POLYMERASE MUTANTS FOR PROBE QPCR

(71) Applicant: AbClonal Science, Inc., Woburn, MA (US)

(72) Inventors: Zhenyu Zhu, Lynnfield, MA (US); Dapeng Sun, Lexington, MA (US); Aine Quimby, Newburyport, MA (US)

(73) Assignee: ABCLONAL SCIENCE, INC., Woborn, MA (US)

(*) Notice: Subject to any disclaimer, the term of this patent is extended or adjusted under 35 U.S.C. 154(b) by 41 days.

This patent is subject to a terminal disclaimer.

(21) Appl. No.: 17/470,557

(22) Filed: Sep. 9, 2021

(65) Prior Publication Data

US 2022/0106576 A1 Apr. 7, 2022

Related U.S. Application Data

(60) Provisional application No. 63/088,546, filed on Oct. 7, 2020.

(51) Int. Cl.
| | | |
|---|---|---|
| *C12N 9/12* | (2006.01) | |
| *C12Q 1/686* | (2018.01) | |
| *C12Q 1/6853* | (2018.01) | |

(52) U.S. Cl.
CPC .......... *C12N 9/1252* (2013.01); *C12Q 1/686* (2013.01); *C12Q 1/6853* (2013.01); *C12Y 207/07007* (2013.01)

(58) Field of Classification Search
None
See application file for complete search history.

(56) References Cited

U.S. PATENT DOCUMENTS

2017/0058330 A1* 3/2017 Chiou .................. C12Q 1/6818
2018/0305673 A1* 10/2018 Vander Horn ....... C12N 9/1252

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

* cited by examiner

*Primary Examiner* — Richard G Hutson
(74) *Attorney, Agent, or Firm* — Eric P. Mirabel

(57) ABSTRACT

Disclosed are Taq DNA polymerase mutants which exhibit enhanced efficiency in qPCR compared to the wild type Taq DNA polymerase. Such mutants include: V62S, V64S, A70F, F73A, A77F, P253G, E255K, D257R, A259F, A271F, L288S, E289K, S357I, L361S, L376S, P382G, T385I, G418P, R419D, E421K, L461S, A472F, E497K, L498S, E524K, D551R, R556D, S679I, L789S, E189K/E507K/ E742K (See Sequence Listing Guide for the mutants' amino acid and protein sequences).

6 Claims, 35 Drawing Sheets

Specification includes a Sequence Listing.

F73A

A77F

P253G

E255K

WT

V64S

A70F

L288S

E289K

S357I

L361S

WT

D257R

A259F

A271F

G418P

R419D

E421K

L461S

WT

L376S

P382G

T385I

E524K

D551R

R556D

S679I

WT

A472F

E497K

L498S

WT

L789S

E189K/E507K/E742K

SEQUENCE LISTING

```
<160> NUMBER OF SEQ ID NOS: 65

<210> SEQ ID NO 1
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
```

-continued

| | |
|---|---|
| atgcgcggta tgctgccgtt atttgaaccg aaaggtcgtg tgctgctggt tgatggtcat | 60 |
| cacttagcat atcgtacctt tcatgccctg aaaggcctga ccacctctcg cggcgaaccg | 120 |
| gttcaggcag tgtatggttt tgccaaatca ctgctgaaag cattaaaaga gatggcgat | 180 |
| gcagtgattg ttgtgtttga tgccaaagcc ccgagctttc gtcatgaagc ctatggcggc | 240 |
| tacaaagcag gtcgcgcccc gaccccggaa gattttccgc gtcagctggc cttaattaaa | 300 |
| gaattagttg acttgctggg cttagcacgt ctggaagttc cgggctatga agcagatgat | 360 |
| gttttagcct cactggccaa aaaagccgaa aaagaaggct atgaagttcg cattctgacc | 420 |
| gcagataagg atctgtatca gctgctgagc gatcgtattc atgtgttaca tccggaaggc | 480 |
| tatctgatta ccccggcatg gttatgggaa aaatatggtt tacgtccgga tcagtgggca | 540 |
| gattatcgtg cactgaccgg tgacgaatca gataatctgc cggcgttaa aggtattggt | 600 |
| gaaaaaaccg cccggaaatt attagaagaa tggggtagtc tggaagcatt actgaaaaat | 660 |
| ctggatcgcc tgaaaccggc aattcgcgaa aaaatttttag cccacatgga tgacttaaaa | 720 |
| ctgtcttggg atctggccaa agtgcgtacc gatctgccgt tagaagttga ttttgccaaa | 780 |
| cgtcgcgaac cggatcgtga acgcctacga gcctttctgg aacgcttaga atttggctca | 840 |
| ctgttacatg aatttggctt actggaatct ccgaaagcat tagaagaagc cccgtggccg | 900 |
| ccgccggaag gcgcctttgt gggctttgtg ctgagtagga aagaaccgat gtgggcagac | 960 |
| ttgctggccc tggccgcagc acgcggcggt cgcgttcatc gtgccccgga accgtacaaa | 1020 |
| gccctgcgtg acctgaaaga agcacgcggc ttattagcca aagacctgag tgttctggca | 1080 |
| ttaagggaag gcttaggcct gccgccgggc gatgatccga tgctgctggc ctatctgctt | 1140 |
| gacccgagta ataccacccc ggaaggcgtt gcacgtcgct atggcggcga gtggaccgaa | 1200 |
| gaagcaggcg aacgtgcagc cctgtcagaa cgtctgtttg ccaatctgtg gggtcgctta | 1260 |
| gaaggcgaag aacgcttact gtggttatat cgtgaagtgg aacgtccgct gagcgcagtg | 1320 |
| ctggcacaca tggaagccac cggtgtgcgc ttagatgttg catatctgcg tgccctgtct | 1380 |
| ctggaagttg cagaagaaat tgcacgctta gaagccgaag ttttcgctt agcaggtcat | 1440 |
| ccgtttaact aaatagtcg cgatcagctg gaaagggttc tgtttgatga attaggcctg | 1500 |
| ccggcaattg gcaagaccga aaaaaccggt aaacgctcta cctcagccgc agttctggaa | 1560 |
| gccctgcgcg aagcccatcc gattgttgaa aaattttac agtatcgtga actgaccaaa | 1620 |
| ctgaaatcta cctatattga tccgttaccg gatctaattc atccgcgtac cggtcgctta | 1680 |
| catacccgtt ttaatcagac cgccaccgcc accggtcgct tatcaagtag cgatccgaac | 1740 |
| ttgcagaata ttccggtgcg taccccgtta ggtcagcgca ttcgtcgtgc ctttattgca | 1800 |
| gaagaaggtt ggttattagt tgcattagat tatagtcaga ttgaactgcg tgtgttagcc | 1860 |
| catctgagcg gcgacgaaaa tctgattcgt gtgtttcagg aaggtcgcga tattcatacc | 1920 |
| gaaaccgcct cttggatgtt tggtgttccg cgcgaagcag ttgatccgtt aatgcgccgt | 1980 |
| gcagccaaaa ccattaattt tggtgtgctg tatggtatga gcgcacatcg cctgtcacag | 2040 |
| gaactggcaa ttccgtatga agaagcacag gcctttattg aacgctattt tcagtctttt | 2100 |
| ccgaaagttc gcgcatggat tgaaaaaacc ttagaagaag gtcgtcgtcg cggctatgtg | 2160 |
| gaaaccctgt ttggtcgtcg tcgctatgtt ccggatctgg aagcgagagt taaatcagtg | 2220 |
| cgtgaagccg ccgaacgcat ggcctttaat atgccggttc agggaacggc agctgacctt | 2280 |
| atgaaactgg caatggttaa actgtttccg cgcctgaaag aaatgggtgc acgaatgctg | 2340 |
| ttacaggttc atgatgaatt agttctggaa gccccgaaag aacgcgccga agcagttgca | 2400 |

-continued

```
cgtctggcca aagaagtgat ggaaggtgtg tatccgttag cagttccgtt agaagtggaa    2460
gtgggtattg gtgaagattg gctgagcgcc aaagaaggtt ctggcagttc aggtcatcac    2520
caccatcatc actaa                                                     2535
```

<210> SEQ ID NO 2
<211> LENGTH: 844
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
```

```
                    325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
                595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
            690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
                740                 745                 750
```

```
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
        770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
                820                 825                 830
Gly Ser Gly Ser Ser Gly His His His His His His
        835                 840

<210> SEQ ID NO 3
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcatctattg ttgtgtttga tgccaaagcc ccgagctttc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc gggctatga gcagatgat      360 gttttagcct cactggccaa aaaagccgaa aagaaggct atgaagttcg cattctgacc      420
gcagataagg atctgtatca gctgctgagc gatcgtattc atgtgttaca tccggaaggc     480
tatctgatta ccccggcatg gttatgggaa aaatatggtt acgtccgga tcagtgggca      540 gattatcgtg cactgaccgg tgacgaatca gataatctgc cggcgttaa aggtattggt      600 gaaaaaaccg cccggaaatt attagaagaa tggggtagtc tggaagcatt actgaaaaat     660
ctggatcgcc tgaaaccggc aattcgcgaa aaaatttag cccacatgga tgacttaaaa     720
ctgtcttggg atctggccaa agtgcgtacc gatctgccgt tagaagttga ttttgccaaa     780
cgtcgcgaac cggatcgtga acgcctacga gcctttctgg aacgcttaga atttggctca     840
ctgttacatg aatttggctt actggaatct ccgaaagcat agaagaagc cccgtggccg     900 ccgccggaag cgccctttgt gggctttgtg ctgagtagga agaaccgat gtgggcagac     960 ttgctggccc tggccgcagc acgcggcggt cgcgttcatc gtgccccgga accgtacaaa    1020
gccctgcgtg acctgaaaga agcacgcggc ttattagcca aagacctgag tgttctggca    1080
ttaagggaag gcttaggcct gccgccgggc gatgatccga tgctgctggc ctatctgctt    1140
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
ctggaagttg cagaagaaat tgcacgctta gaagccgaag ttttcgctt agcaggtcat    1440 ccgtttaact aaatagtcg cgatcagctg gaaagggttc tgtttgatga attaggcctg    1500
```

```
ccggcaattg gcaagaccga aaaaaccggt aaacgctcta cctcagccgc agttctggaa      1560
gccctgcgcg aagcccatcc gattgttgaa aaaattttac agtatcgtga actgaccaaa      1620
ctgaaatcta cctatattga tccgttaccg gatctaattc atccgcgtac cggtcgctta      1680
catacccgtt ttaatcagac cgccaccgcc accggtcgct tatcaagtag cgatccgaac      1740
ttgcagaata ttccggtgcg taccccgtta ggtcagcgca ttcgtcgtgc ctttattgca      1800
gaagaaggtt ggttattagt tgcattagat tatagtcaga ttgaactgcg tgtgttagcc      1860
catctgagcg gcgacgaaaa tctgattcgt gtgtttcagg aaggtcgcga tattcatacc      1920
gaaaccgcct cttggatgtt tggtgttccg cgcgaagcag ttgatccgtt aatgcgccgt      1980
gcagccaaaa ccattaattt tggtgtgctg tatggtatga gcgcacatcg cctgtcacag      2040
gaactggcaa ttccgtatga agaagcacag gcctttattg aacgctattt tcagtctttt      2100
ccgaaagttc gcgcatggat tgaaaaaacc ttagaagaag gtcgtcgtcg cggctatgtg      2160
gaaaccctgt ttggtcgtcg tcgctatgtt ccggatctgg aagcgagagt taaatcagtg      2220
cgtgaagccg ccgaacgcat ggcctttaat atgccggttc agggaacggc agctgacctt      2280
atgaaactgg caatggttaa actgtttccg cgcctggaag aaatgggtgc acgaatgctg      2340
ttacaggttc atgatgaatt agttctggaa gccccgaaag aacgcgccga agcagttgca      2400
cgtctggcca agaagtgat ggaaggtgtg tatccgttag cagttccgtt agaagtggaa      2460
gtgggtattg gtgaagattg gctgagcgcc aaagaaggtt ctggcagttc aggtcatcac      2520
caccatcatc actaa                                                     2535
```

<210> SEQ ID NO 4
<211> LENGTH: 844
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Ser Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
```

```
                         165                 170                 175
Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590
```

Arg Ile Arg Arg Ala Phe Ile Ala Glu Glu Gly Trp Leu Val Ala
    595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
    835                 840

<210> SEQ ID NO 5
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattt ctgtgtttga tgccaaagcc ccgagctttc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc gggctatga agcagatgat    360 gttttagcct cactggccaa aaaagccgaa aaagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt acgtccggga tcagtgggca    540
gattatcgtg cactgaccgg tgacgaatca gataatctgc cgggcgttaa aggtattggt    600

```
gaaaaaaccg cccggaaatt attagaagaa tggggtagtc tggaagcatt actgaaaaat      660
ctggatcgcc tgaaaccggc aattcgcgaa aaaattttag cccacatgga tgacttaaaa      720
ctgtcttggg atctggccaa agtgcgtacc gatctgccgt tagaagttga ttttgccaaa      780
cgtcgcgaac cggatcgtga acgcctacga gcctttctgg aacgcttaga atttggctca      840
ctgttacatg aatttggctt actggaatct ccgaaagcat tagaagaagc cccgtggccg      900
ccgccggaag gcgcctttgt gggctttgtg ctgagtagga agaaccgat gtgggcagac       960 ttgctggccc tggccgcagc acgcggcggt cgcgttcatc gtgccccgga accgtacaaa     1020
gccctgcgtg acctgaaaga agcacgcggc ttattagcca aagacctgag tgttctggca     1080
ttaagggaag gcttaggcct gccgccgggc gatgatccga tgctgctggc ctatctgctt     1140
gacccgagta ataccacccc ggaaggcgtt gcacgtcgct atggcggcga gtggaccgaa     1200
gaagcaggcg aacgtgcagc cctgtcagaa cgtctgtttg ccaatctgtg gggtcgctta     1260
gaaggcgaag aacgcttact gtggttatat cgtgaagtgg aacgtccgct gagcgcagtg     1320
ctggcacaca tggaagccac cggtgtgcgc ttagatgttg catatctgcg tgccctgtct     1380
ctggaagttg cagaagaaat tgcacgctta gaagccgaag ttttcgctt agcaggtcat      1440 ccgtttaact aaatagtcg cgatcagctg gaaagggttc tgtttgatga attaggcctg      1500
ccggcaattg gcaagaccga aaaaaccggt aaacgctcta cctcagccgc agttctggaa     1560
gccctgcgcg aagcccatcc gattgttgaa aaaattttac agtatcgtga actgaccaaa     1620
ctgaaatcta cctatattga tccgttaccg gatctaattc atccgcgtac cggtcgctta     1680
catacccgtt ttaatcagac cgccaccgcc accggtcgct tatcaagtag cgatccgaac     1740
ttgcagaata ttccggtgcg tacccccgtta ggtcagcgca ttcgtcgtgc ctttattgca    1800
gaagaaggtt ggttattagt tgcattagat tatagtcaga ttgaactgcg tgtgttagcc     1860
catctgagcg gcgacgaaaa tctgattcgt gtgtttcagg aaggtcgcga tattcatacc     1920
gaaaccgcct cttggatgtt tggtgttccg cgcgaagcag ttgatccgtt aatgcgccgt     1980
gcagccaaaa ccattaattt tggtgtgctg tatggtatga gcgcacatcg cctgtcacag     2040
gaactggcaa ttccgtatga agaagcacag gcctttattg aacgctattt tcagtctttt    2100
ccgaaagttc gcgcatggat tgaaaaaacc ttagaagaag gtcgtcgtcg cggctatgtg     2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgaccttt   2280 atgaaactgg caatggttaa actgtttccg cgcctggaaa aaatgggtgc acgaatgctg    2340
ttacaggttc atgatgaatt agttctggaa gccccgaaag aacgcgccga agcagttgca    2400
cgtctggcca aagaagtgat ggaagtgtg tatccgttag cagttccgtt agaagtggaa      2460
gtgggtattg gtgaagattg gctgagcgcc aaagaaggtt ctggcagttc aggtcatcac    2520
caccatcatc actaa                                                     2535
```

<210> SEQ ID NO 6
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Arg Gly Met Leu Pro Leu Phe Glu Pro Lys Gly Arg Val Leu Leu

```
1               5                    10                   15
Val Asp Gly His His Leu Ala Tyr Arg Thr Phe His Ala Leu Lys Gly
                20                  25                  30
Leu Thr Thr Ser Arg Gly Glu Pro Val Gln Ala Val Tyr Gly Phe Ala
                35                  40                  45
Lys Ser Leu Leu Lys Ala Leu Lys Glu Asp Gly Asp Ala Val Ile Ser
                50                  55                  60
Val Phe Asp Ala Lys Ala Pro Ser Phe Arg His Glu Ala Tyr Gly Gly
 65                 70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
                100                 105                 110
Val Pro Gly Tyr Glu Ala Asp Asp Val Leu Ala Ser Leu Ala Lys Lys
                115                 120                 125
Ala Glu Lys Glu Gly Tyr Glu Val Arg Ile Leu Thr Ala Asp Lys Asp
                130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
                210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
                275                 280                 285
Glu Ser Pro Lys Ala Leu Glu Glu Ala Pro Trp Pro Pro Pro Glu Gly
                290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
```

```
Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
                515                 520                 525

Val Glu Lys Ile Leu Gln Tyr Arg Glu Leu Thr Lys Leu Lys Ser Thr
                530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
                690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

Gly Ser Gly Ser Ser Gly His His His His His
835                 840
```

<210> SEQ ID NO 7
<211> LENGTH: 2535
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

| | | | | | |
|---|---|---|---|---|---|
| atgcgcggta | tgctgccgtt | atttgaaccg | aaaggtcgtg | tgctgctggt | tgatggtcat | 60 |
| cacttagcat | atcgtacctt | tcatgccctg | aaaggcctga | ccacctctcg | cggcgaaccg | 120 |
| gttcaggcag | tgtatggttt | tgccaaatca | ctgctgaaag | cattaaaaga | agatggcgat | 180 |
| gcagtgattg | ttgtgtttga | tgccaaattc | ccgagctttc | gtcatgaagc | ctatggcggc | 240 |
| tacaaagcag | tcgcgcccc | gaccccggaa | gattttccgc | gtcagctggc | cttaattaaa | 300 |
| gaattagttg | acttgctggg | cttagcacgt | ctggaagttc | cgggctatga | agcagatgat | 360 |
| gttttagcct | cactgccaa | aaaagccgaa | aaagaaggct | atgaagttcg | cattctgacc | 420 |
| gcagataagg | atctgtatca | gctgctgagc | gatcgtattc | atgtgttaca | tccggaaggc | 480 |
| tatctgatta | ccccggcatg | gttatgggaa | aaatatggtt | tacgtccgga | tcagtgggca | 540 |
| gattatcgtg | cactgaccgg | tgacgaatca | gataatctgc | cgggcgttaa | aggtattggt | 600 |
| gaaaaaaccg | cccggaaatt | attagaagaa | tggggtagtc | tggaagcatt | actgaaaaat | 660 |
| ctggatcgcc | tgaaaccggc | aattcgcgaa | aaaattttag | cccacatgga | tgacttaaaa | 720 |
| ctgtcttggg | atctggccaa | agtgcgtacc | gatctgccgt | tagaagttga | ttttgccaaa | 780 |
| cgtcgcgaac | cggatcgtga | acgcctacga | gcctttctgg | aacgcttaga | atttggctca | 840 |
| ctgttacatg | aatttggctt | actggaatct | ccgaaagcat | tagaagaagc | ccgtggccg | 900 |
| ccgccggaag | gcgcctttgt | gggctttgtg | ctgagtagga | agaaccgat | gtgggcagac | 960 |
| ttgctggccc | tggccgcagc | acgcggcggt | cgcgttcatc | gtgccccgga | accgtacaaa | 1020 |
| gccctgcgtg | acctgaaaga | agcacgcggc | ttattagcca | aagacctgag | tgttctggca | 1080 |
| ttaagggaag | gcttaggcct | gccgccgggc | gatgatccga | tgctgctggc | ctatctgctt | 1140 |
| gacccgagta | ataccacccc | ggaaggcgtt | gcacgtcgct | atggcggcga | gtggaccgaa | 1200 |
| gaagcaggcg | aacgtgcagc | cctgtcagaa | cgtctgtttg | ccaatctgtg | gggtcgctta | 1260 |
| gaaggcgaag | aacgcttact | gtggttatat | cgtgaagtgg | aacgtccgct | gagcgcagtg | 1320 |
| ctggcacaca | tggaagccac | cggtgtgcgc | ttagatgttg | catatctgcg | tgccctgtct | 1380 |
| ctggaagttg | cagaagaaat | tgcacgctta | gaagccgaag | ttttcgctt | agcaggtcat | 1440 |
| ccgtttaact | aaatagtcg | cgatcagctg | gaaagggttc | tgtttgatga | attaggcctg | 1500 |
| ccggcaattg | gcaagaccga | aaaaaccggt | aaacgctcta | cctcagccgc | agttctggaa | 1560 |
| gccctgcgcg | aagcccatcc | gattgttgaa | aaaattttac | agtatcgtga | actgaccaaa | 1620 |
| ctgaaatcta | cctatattga | tccgttaccg | gatctaattc | atccgcgtac | cggtcgctta | 1680 |
| cataccccgtt | taatcagac | cgccaccgcc | accggtcgct | atcaagtag | cgatccgaac | 1740 |
| ttgcagaata | ttccggtgcg | taccccgtta | ggtcagcgca | ttcgtcgtgc | ctttattgca | 1800 |
| gaagaaggtt | ggttattagt | tgcattagat | tatagtcaga | ttgaactgcg | tgtgttagcc | 1860 |
| catctgagcg | gcgacgaaaa | tctgattcgt | gtgtttcagg | aaggtcgcga | tattcatacc | 1920 |
| gaaaccgcct | cttggatgtt | tggtgttccg | cgcgaagcag | ttgatccgtt | aatgcgccgt | 1980 |
| gcagccaaaa | ccattaattt | tggtgtgctg | tatggtatga | gcgcacatcg | cctgtcacag | 2040 |

```
gaactggcaa ttccgtatga agaagcacag gcctttattg aacgctattt tcagtctttt     2100
ccgaaagttc gcgcatggat tgaaaaaacc ttagaagaag gtcgtcgtcg cggctatgtg     2160
gaaaccctgt ttggtcgtcg tcgctatgtt ccggatctgg aagcgagagt taaatcagtg     2220
cgtgaagccg ccgaacgcat ggcctttaat atgccggttc agggaacggc agctgacctt     2280
atgaaactgg caatggttaa actgtttccg cgcctggaag aaatgggtgc acgaatgctg     2340
ttacaggttc atgatgaatt agttctggaa gccccgaaag aacgcgccga agcagttgca     2400
cgtctggcca aagaagtgat ggaaggtgtg tatccgttag cagttccgtt agaagtggaa     2460
gtgggtattg gtgaagattg gctgagcgcc aaagaaggtt ctggcagttc aggtcatcac     2520
caccatcatc actaa                                                      2535
```

<210> SEQ ID NO 8
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Phe Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

```
Leu Glu Arg Leu Glu Phe Gly Ser Leu Leu His Glu Phe Gly Leu Leu
        275                 280                 285

Glu Ser Pro Lys Ala Leu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685
```

```
Ala Gln Ala Phe Ile Glu Arg Tyr Phe Gln Ser Phe Pro Lys Val Arg
        690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830
Gly Ser Gly Ser Ser Gly His His His His His His
        835                 840

<210> SEQ ID NO 9
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga gatggcgat     180 gcagtgattg ttgtgtttga tgccaaagcc ccgagcgctc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc cgggctatga agcagatgat     360
gttttagcct cactggccaa aaaagccgaa aagaaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt acgtccgga tcagtgggca     540 gattatcgtg cactgaccgg tgacgaatca gataatctgc cggcgttaa aggtattggt     600 gaaaaaccg cccggaaatt attagaagaa tggggtagtc tggaagcatt actgaaaaat     660
ctggatcgcc tgaaaccggc aattcgcgaa aaaattttag cccacatgga tgacttaaaa     720
ctgtcttggg atctggccaa agtgcgtacc gatctgccgt tagaagttga ttttgccaaa     780
cgtcgcgaac cggatcgtga cgcctacga gcctttctgg aacgcttaga atttggctca     840
ctgttacatg aatttggctt actggaatct ccgaaagcat tagaagaagc cccgtggccg     900
ccgccggaag gcgcctttgt gggctttgtg ctgagtagga agaaccgat gtgggcagac     960 ttgctggccc tggccgcagc acgcggcggt cgcgttcatc gtgccccgga accgtacaaa    1020
gccctgcgtg acctgaaaga agcacgcggc ttattagcca agacctgag tgttctggca    1080 ttaagggaag gcttaggcct gccgccgggc gatgatccga tgctgctggc ctatctgctt    1140
```

```
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
ctggaagttg cagaagaaat tgcacgctta gaagccgaag tttttcgctt agcaggtcat    1440
ccgtttaact aaatagtcg cgatcagctg gaaagggttc tgtttgatga attaggcctg     1500
ccggcaattg gcaagaccga aaaaaccggt aaacgctcta cctcagccgc agttctggaa    1560
gccctgcgcg aagcccatcc gattgttgaa aaaattttac agtatcgtga actgaccaaa    1620
ctgaaatcta cctatattga tccgttaccg gatctaattc atccgcgtac cggtcgctta    1680 cataccgtt ttaatcagac cgccaccgcc accggtcgct atcaagtag cgatccgaac      1740 ttgcagaata ttccggtgcg tacccgtta ggtcagcgca ttcgtcgtgc ctttattgca     1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaattt tggtgtgctg tatggtatga gcgcacatcg cctgtcacag    2040
gaactggcaa ttccgtatga agaagcacag gcctttattg aacgctattt tcagtctttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
ttacaggttc atgatgaatt agttctggaa gccccgaaag aacgcgccga agcagttgca    2400
cgtctggcca agaagtgat ggaaggtgtg tatccgttag cagttccgtt agaagtggaa     2460
gtgggtattg gtgaagattg gctgagcgcc aaagaaggtt ctggcagttc aggtcatcac    2520
caccatcatc actaa                                                     2535
```

<210> SEQ ID NO 10
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Ala Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

```
Val Pro Gly Tyr Glu Ala Asp Val Leu Ala Ser Leu Ala Lys Lys
            115                 120                 125

Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525
```

```
Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
        835                 840
```

<210> SEQ ID NO 11
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaatt ctatggcggc    240

| | |
|---|---|
| tacaaagcag gtcgcgcccc gacccggaa gattttccgc gtcagctggc cttaattaaa | 300 |
| gaattagttg acttgctggg cttagcacgt ctggaagttc cgggctatga agcagatgat | 360 |
| gttttagcct cactggccaa aaaagccgaa aaagaaggct atgaagttcg cattctgacc | 420 |
| gcagataagg atctgtatca gctgctgagc gatcgtattc atgtgttaca tccggaaggc | 480 |
| tatctgatta ccccggcatg gttatgggaa aaatatggtt tacgtccgga tcagtgggca | 540 |
| gattatcgtg cactgaccgg tgacgaatca gataatctgc cgggcgttaa aggtattggt | 600 |
| gaaaaaccg cccggaaatt attagaagaa tggggtagtc tggaagcatt actgaaaaat | 660 |
| ctggatcgcc tgaaaccggc aattcgcgaa aaaattttag cccacatgga tgacttaaaa | 720 |
| ctgtcttggg atctggccaa agtgcgtacc gatctgccgt tagaagttga ttttgccaaa | 780 |
| cgtcgcgaac cggatcgtga acgcctacga gcctttctgg aacgcttaga atttggctca | 840 |
| ctgttacatg aatttggctt actggaatct ccgaaagcat tagaagaagc cccgtggccg | 900 |
| ccgccggaag gcgcctttgt gggctttgtg ctgagtagga agaaccgat gtgggcagac | 960 |
| ttgctggccc tggccgcagc acgcggcggt cgcgttcatc gtgccccgga accgtacaaa | 1020 |
| gccctgcgtg acctgaaaga agcacgcggc ttattagcca aagacctgag tgttctggca | 1080 |
| ttaagggaag gcttaggcct gccgccgggc gatgatccga tgctgctggc ctatctgctt | 1140 |
| gacccgagta ataccacccc ggaaggcgtt gcacgtcgct atggcggcga gtggaccgaa | 1200 |
| gaagcaggcg aacgtgcagc cctgtcagaa cgtctgtttg ccaatctgtg gggtcgctta | 1260 |
| gaaggcgaag aacgcttact gtggttatat cgtgaagtgg aacgtccgct gagcgcagtg | 1320 |
| ctggcacaca tggaagccac cggtgtgcgc ttagatgttg catatctgcg tgccctgtct | 1380 |
| ctggaagttg cagaagaaat tgcacgctta gaagccgaag tttttcgctt agcaggtcat | 1440 |
| ccgtttaact taaatagtcg cgatcagctg gaaagggttc tgtttgatga attaggcctg | 1500 |
| ccggcaattg gcaagaccga aaaaaccggt aaacgctcta cctcagccgc agttctggaa | 1560 |
| gccctgcgcg aagcccatcc gattgttgaa aaaattttac agtatcgtga actgaccaaa | 1620 |
| ctgaaatcta cctatattga tccgttaccg gatctaattc atccgcgtac cggtcgctta | 1680 |
| catacccgtt ttaatcagac cgccaccgcc accggtcgct tatcaagtag cgatccgaac | 1740 |
| ttgcagaata ttccggtgcg taccccgtta ggtcagcgca ttcgtcgtgc ctttattgca | 1800 |
| gaagaaggtt ggttattagt tgcattagat tatagtcaga ttgaactgcg tgtgttagcc | 1860 |
| catctgagcg gcgacgaaaa tctgattcgt gtgtttcagg aaggtcgcga tattcatacc | 1920 |
| gaaaccgcct cttggatgtt tggtgttccg cgcgaagcag ttgatccgtt aatgcgccgt | 1980 |
| gcagccaaaa ccattaattt tggtgtgctg tatggtatga gcgcacatcg cctgtcacag | 2040 |
| gaactggcaa ttccgtatga agaagcacag gcctttattg aacgctattt tcagtctttt | 2100 |
| ccgaaagttc gcgcatggat tgaaaaaacc ttagaagaag gtcgtcgtcg cggctatgtg | 2160 |
| gaaaccctgt ttggtcgtcg tcgctatgtt ccggatctgg aagcgagagt taaatcagtg | 2220 |
| cgtgaagccg ccgaacgcat ggcctttaat atgccggttc agggaacggc agctgacctt | 2280 |
| atgaaactgg caatggttaa actgtttccg cgcctggaag aaatgggtgc acgaatgctg | 2340 |
| ttacaggttc atgatgaatt agttctggaa gccccgaaag aacgcgccga agcagttgca | 2400 |
| cgtctggcca agaagtgat ggaaggtgtg tatccgttag cagttccgtt agaagtggaa | 2460 |
| gtgggtattg gtgaagattg gctgagcgcc aaagaaggtt ctggcagttc aggtcatcac | 2520 |
| caccatcatc actaa | 2535 |

```
<210> SEQ ID NO 12
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Phe Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365
```

-continued

```
Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
                515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
```

```
                    785                 790                 795                 800
Arg Leu Ala Lys Glu Val Met Glu Gly Val Tyr Pro Leu Ala Val Pro
                        805                 810                 815

Leu Glu Val Glu Val Gly Ile Gly Glu Asp Trp Leu Ser Ala Lys Glu
                820                 825                 830

Gly Ser Gly Ser Ser Gly His His His His His His
                835                 840

<210> SEQ ID NO 13
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcagtgattg ttgtgtttga tgccaaagcc ccgagctttc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc gggctatga agcagatgat     360 gttttagcct cactggccaa aaaagccgaa aagaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt acgtccgga tcagtgggca     540 gattatcgtg cactgaccgg tgacgaatca gataatctgc cggcgttaa aggtattggt     600 gaaaaaaccg cccggaaatt attagaagaa tggggtagtc tggaagcatt actgaaaaat     660
ctggatcgcc tgaaaccggc aattcgcgaa aaaattttag cccacatgga tgacttaaaa     720
ctgtcttggg atctggccaa agtgcgtacc gatctggggt tagaagttga ttttgccaaa     780
cgtcgcgaac cggatcgtga acgcctacga gcctttctgg aacgcttaga atttggctca     840
ctgttacatg aatttggctt actggaatct ccgaaagcat tagaagaagc cccgtggccg     900
ccgccggaag gcgcctttgt gggctttgtg ctgagtagga agaaccgat gtgggcagac     960 ttgctggccc tggccgcagc acgcggcggt cgcgttcatc gtgccccgga accgtacaaa    1020
gccctgcgtg aacctgaaaga agcacgcggc ttattagcca agacctgag tgttctggca    1080 ttaagggaag gcttaggcct gccgccgggc gatgatccga tgctgctggc ctatctgctt    1140
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
ctggaagttg cagaagaaat tgcacgctta aagccgaag ttttcgctt agcaggtcat    1440 ccgtttaact aaatagtcg cgatcagctg gaaagggttc tgtttgatga attaggcctg    1500
ccggcaattg gcaagaccga aaaaccggt aaacgctcta cctcagccgc agttctggaa    1560
gccctgcgcg aagcccatcc gattgttgaa aaattttac agtatcgtga actgaccaaa    1620
ctgaaatcta cctatattga tccgttaccg gatctaattc atccgcgtac cggtcgctta    1680
catacccgtt ttaatcagac cgccaccgcc accggtcgct tatcaagtag cgatccgaac    1740
```

```
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                    2535
```

<210> SEQ ID NO 14
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205
```

```
Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Gly Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Ile His Thr
```

```
            625                 630                 635                 640
Glu Thr Ala Ser Trp Met Phe Gly Val Pro Arg Glu Ala Val Asp Pro
                    645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
        690                 695                 700
Ala Trp Ile Glu Lys Thr Leu Glu Glu Gly Arg Arg Gly Tyr Val
705                 710                 715                 720
Glu Thr Leu Phe Gly Arg Arg Tyr Val Pro Asp Leu Glu Ala Arg
                    725                 730                 735
Val Lys Ser Val Arg Glu Ala Ala Glu Arg Met Ala Phe Asn Met Pro
                740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
        770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                    805                 810                 815
Leu Glu Val Glu Val Gly Ile Gly Glu Asp Trp Leu Ser Ala Lys Glu
                820                 825                 830
Gly Ser Gly Ser Ser Gly His His His His His
            835                 840

<210> SEQ ID NO 15
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcagtgattg ttgtgtttga tgccaaagcc ccgagctttc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc gggctatga agcagatgat     360 gttttagcct cactgccaa aaagccgaa aagaaggct atgaagttcg cattctgacc      420
gcagataagg atctgtatca gctgctgagc gatcgtattc atgtgttaca tccggaaggc     480
tatctgatta ccccggcatg gttatgggaa aaatatggtt acgtccgga tcagtgggca     540 gattatcgtg cactgaccgg tgacgaatca gataatctgc cggcgttaa aggtattggt     600 gaaaaaaccg cccggaaatt attagaagaa tgggtagtc tggaagcatt actgaaaaat     660
ctggatcgcc tgaaaccggc aattcgcgaa aaattttag cccacatgga tgacttaaaa     720
ctgtcttggg atctgccaa agtgcgtacc gatctgccgt taaagttga ttttgccaaa     780 cgtcgcgaac cggatcgtga acgcctacga gcctttctgg aacgcttaga atttggctca     840
```

```
ctgttacatg aatttggctt actggaatct ccgaaagcat tagaagaagc cccgtggccg    900
ccgccggaag gcgcctttgt gggctttgtg ctgagtagga agaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta aagccgaag ttttcgctt agcaggtcat    1440
ccgtttaact aaatagtcg cgatcagctg aaagggttc tgtttgatga attaggcctg    1500
ccggcaattg gcaagaccga aaaaccggt aaacgctcta cctcagccgc agttctggaa    1560
gccctgcgcg aagcccatcc gattgttgaa aaattttac agtatcgtga actgaccaaa   1620
ctgaaatcta cctatattga tccgttaccg gatctaattc atccgcgtac cggtcgctta   1680
cataccgtt ttaatcagac cgccaccgcc accggtcgct atcaagtag cgatccgaac   1740
ttgcagaata ttccggtgcg tacccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacgg agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaagtgtg tatccgttag cagttccgtt agaagtggaa   2460
gtgggtattg gtgaagattg gctgagcgcc aaagaaggtt ctggcagttc aggtcatcac   2520
caccatcatc actaa                                                   2535
```

<210> SEQ ID NO 16
<211> LENGTH: 844
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

```
Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Lys Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
```

```
                465                 470                 475                 480
        Pro Phe Asn Leu Asn Ser Arg Asp Gln Leu Glu Arg Val Leu Phe Asp
                        485                 490                 495

Glu Leu Gly Leu Pro Ala Ile Gly Lys Thr Glu Lys Thr Gly Lys Arg
                    500                 505                 510

Ser Thr Ser Ala Ala Val Leu Glu Ala Leu Arg Glu Ala His Pro Ile
                    515                 520                 525

Val Glu Lys Ile Leu Gln Tyr Arg Glu Leu Thr Lys Leu Lys Ser Thr
                530                 535                 540

Tyr Ile Asp Pro Leu Pro Asp Leu Ile His Pro Arg Thr Gly Arg Leu
        545                 550                 555                 560

His Thr Arg Phe Asn Gln Thr Ala Thr Ala Thr Gly Arg Leu Ser Ser
                        565                 570                 575

Ser Asp Pro Asn Leu Gln Asn Ile Pro Val Arg Thr Pro Leu Gly Gln
                    580                 585                 590

Arg Ile Arg Arg Ala Phe Ile Ala Glu Glu Gly Trp Leu Leu Val Ala
                    595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
        625                 630                 635                 640

Glu Thr Ala Ser Trp Met Phe Gly Val Pro Arg Glu Ala Val Asp Pro
                        645                 650                 655

Leu Met Arg Arg Ala Ala Lys Thr Ile Asn Phe Gly Val Leu Tyr Gly
                    660                 665                 670

Met Ser Ala His Arg Leu Ser Gln Glu Leu Ala Ile Pro Tyr Glu Glu
                    675                 680                 685

Ala Gln Ala Phe Ile Glu Arg Tyr Phe Gln Ser Phe Pro Lys Val Arg
                690                 695                 700

Ala Trp Ile Glu Lys Thr Leu Glu Glu Gly Arg Arg Arg Gly Tyr Val
        705                 710                 715                 720

Glu Thr Leu Phe Gly Arg Arg Arg Tyr Val Pro Asp Leu Glu Ala Arg
                        725                 730                 735

Val Lys Ser Val Arg Glu Ala Ala Glu Arg Met Ala Phe Asn Met Pro
                    740                 745                 750

Val Gln Gly Thr Ala Ala Asp Leu Met Lys Leu Ala Met Val Lys Leu
                    755                 760                 765

Phe Pro Arg Leu Glu Glu Met Gly Ala Arg Met Leu Leu Gln Val His
                770                 775                 780

Asp Glu Leu Val Leu Glu Ala Pro Lys Glu Arg Ala Glu Ala Val Ala
        785                 790                 795                 800

Arg Leu Ala Lys Glu Val Met Glu Gly Val Tyr Pro Leu Ala Val Pro
                        805                 810                 815

Leu Glu Val Glu Val Gly Ile Gly Glu Asp Trp Leu Ser Ala Lys Glu
                    820                 825                 830

Gly Ser Gly Ser Ser Gly His His His His His
                    835                 840

<210> SEQ ID NO 17
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 17

```
atgcgcggta tgctgccgtt atttgaaccg aaaggtcgtg tgctgctggt tgatggtcat    60
cacttagcat atcgtacctt tcatgccctg aaaggcctga ccacctctcg cggcgaaccg   120
gttcaggcag tgtatggttt tgccaaatca ctgctgaaag cattaaaaga agatggcgat   180
gcagtgattg ttgtgtttga tgccaaagcc ccgagctttc gtcatgaagc ctatggcggc   240
tacaaagcag gtcgcgcccc gacccggaa gattttccgc gtcagctggc cttaattaaa   300
gaattagttg acttgctggg cttagcacgt ctggaagttc cgggctatga agcagatgat   360
gttttagcct cactgccaa aaagccgaa aagaaggct atgaagttcg cattctgacc   420
gcagataagg atctgtatca gctgctgagc gatcgtattc atgtgttaca tccggaaggc   480
tatctgatta ccccggcatg gttatgggaa aaatatggtt tacgtccgga tcagtgggca   540
gattatcgtg cactgaccgg tgacgaatca gataatctgc cgggcgttaa aggtattggt   600
gaaaaaccg cccggaaatt attagaagaa tggggtagtc tggaagcatt actgaaaaat   660
ctggatcgcc tgaaaccggc aattcgcgaa aaaatttag cccacatgga tgacttaaaa   720
ctgtcttggg atctggccaa agtgcgtacc gatctgccgt tagaagttcg ttttgccaaa   780
cgtcgcgaac cggatcgtga acgcctacga gcctttctgg aacgcttaga atttggctca   840
ctgttacatg aatttggctt actggaatct ccgaaagcat tagaagaagc cccgtggccg   900
ccgccggaag gcgcctttgt gggctttgtg ctgagtagga agaaccgat gtgggcagac   960
ttgctggccc tggccgcagc acgcggcggt cgcgttcatc gtgccccgga accgtacaaa  1020
gccctgcgtg acctgaaaga agcacgcggc ttattagcca aagacctgag tgttctggca  1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
ctggaagttg cagaagaaat tgcacgctta gaagccgaag tttttcgctt agcaggtcat  1440
ccgtttaact aaatagtcg cgatcagctg gaaagggttc tgtttgatga attaggcctg  1500
ccggcaattg gcaagaccga aaaaaccggt aaacgctcta cctcagccgc agttctggaa  1560
gccctgcgcg aagcccatcc gattgttgaa aaaattttac agtatcgtga actgaccaaa  1620
ctgaaatcta cctatattga tccgttaccg gatctaattc atccgcgtac cggtcgctta  1680
catacccgtt ttaatcagac cgccaccgcc accggtcgct tatcaagtag cgatccgaac  1740
ttgcagaata ttccggtgcg tacccccgtta ggtcagcgca ttcgtcgtgc ctttattgca  1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgtcacag  2040
gaactggcaa ttccgtatga agaagcacag gcctttattg aacgctattt tcagtctttt  2100
ccgaaagttc gcgcatggat tgaaaaaacc ttagaagaag tcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
```

```
atgaaactgg caatggttaa actgtttccg cgcctggaag aaatgggtgc acgaatgctg    2340
ttacaggttc atgatgaatt agttctggaa gccccgaaag aacgcgccga agcagttgca    2400
cgtctggcca agaagtgat ggaaggtgtg tatccgttag cagttccgtt agaagtggaa     2460
gtgggtattg gtgaagattg gctgagcgcc aaagaaggtt ctggcagttc aggtcatcac    2520
caccatcatc actaa                                                     2535
```

<210> SEQ ID NO 18
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Arg Gly Met Leu Pro Leu Phe Glu Pro Lys Gly Arg Val Leu Leu
 1               5                  10                  15

Val Asp Gly His His Leu Ala Tyr Arg Thr Phe His Ala Leu Lys Gly
             20                  25                  30

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Ile Val
     50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Arg Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
```

```
            305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
                515                 520                 525
Val Glu Lys Ile Leu Gln Tyr Arg Glu Leu Thr Lys Leu Lys Ser Thr
    530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Ala
                595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
                675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Gly Tyr Val
705                 710                 715                 720
Glu Thr Leu Phe Gly Arg Arg Arg Tyr Val Pro Asp Leu Glu Ala Arg
                725                 730                 735
```

```
Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His His
            835                 840
```

<210> SEQ ID NO 19
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | | |
|---|---|---:|
| atgcgcggta tgctgccgtt atttgaaccg aaaggtcgtg tgctgctggt tgatggtcat | | 60 |
| cacttagcat atcgtacctt tcatgccctg aaaggcctga ccacctctcg cggcgaaccg | | 120 |
| gttcaggcag tgtatggttt tgccaaatca ctgctgaaag cattaaaaga gatgggcgat | | 180 |
| gcagtgattg ttgtgtttga tgccaaagcc ccgagctttc gtcatgaagc ctatggcggc | | 240 |
| tacaaagcag gtcgcgcccc gaccccggaa gattttccgc gtcagctggc cttaattaaa | | 300 |
| gaattagttg acttgctggg cttagcacgt ctggaagttc cgggctatga agcagatgat | | 360 |
| gttttagcct cactggccaa aaaagccgaa aagaaggct atgaagttcg cattctgacc | | 420 |
| gcagataagg atctgtatca gctgctgagc gatcgtattc atgtgttaca tccggaaggc | | 480 |
| tatctgatta ccccggcatg gttatgggaa aaatatggtt acgtccgga tcagtgggca | | 540 |
| gattatcgtg cactgaccgg tgacgaatca gataatctgc cgggcgttaa aggtattggt | | 600 |
| gaaaaaaccg cccggaaatt attagaagaa tggggtagtc tggaagcatt actgaaaaat | | 660 |
| ctggatcgcc tgaaaccggc aattcgcgaa aaatttag cccacatgga tgacttaaaa | | 720 |
| ctgtcttggg atctggccaa agtgcgtacc gatctgccgt tagaagttga ttttttcaaa | | 780 |
| cgtcgcgaac cggatcgtga acgcctacga gcctttctgg aacgcttaga atttggctca | | 840 |
| ctgttacatg aatttggctt actggaatct ccgaaagcat agaagaagc cccgtggccg | | 900 |
| ccgccggaag gcgcctttgt gggctttgtg ctgagtagga agaaccgat gtgggcagac | | 960 |
| ttgctggccc tggccgcagc acgcggcggt cgcgttcatc gtgccccgga accgtacaaa | | 1020 |
| gccctgcgtg acctgaaaga agcacgcggc ttattagcca aagacctgag tgttctggca | | 1080 |
| ttaagggaag gcttaggcct gccgccgggc gatgatccga tgctgctggc ctatctgctt | | 1140 |
| gacccgagta ataccacccc ggaaggcgtt gcacgtcgct atggcggcga gtggaccgaa | | 1200 |
| gaagcaggcg aacgtgcagc cctgtcagaa cgtctgtttg ccaatctgtg gggtcgctta | | 1260 |
| gaaggcgaag aacgcttact gtggttatat cgtgaagtgg aacgtccgct gagcgcagtg | | 1320 |
| ctggcacaca tggaagccac cggtgtgcgc ttagatgttg catatctgcg tgccctgtct | | 1380 |

-continued

```
ctggaagttg cagaagaaat tgcacgctta gaagccgaag ttttcgctt agcaggtcat      1440 ccgtttaact taaatagtcg cgatcagctg gaaagggttc tgtttgatga attaggcctg      1500
ccggcaattg gcaagaccga aaaaaccggt aaacgctcta cctcagccgc agttctggaa      1560
gccctgcgcg aagcccatcc gattgttgaa aaaattttac agtatcgtga actgaccaaa      1620
ctgaaatcta cctatattga tccgttaccg gatctaattc atccgcgtac cggtcgctta      1680 cataccccgtt ttaatcagac cgccaccgcc accggtcgct tatcaagtag cgatccgaac      1740
ttgcagaata ttccggtgcg taccccgtta ggtcagcgca ttcgtcgtgc ctttattgca      1800
gaagaaggtt ggttattagt tgcattagat tatagtcaga ttgaactgcg tgtgttagcc      1860
catctgagcg gcgacgaaaa tctgattcgt gtgtttcagg aaggtcgcga tattcatacc      1920
gaaaccgcct cttggatgtt tggtgttccg cgcgaagcag ttgatccgtt aatgcgccgt      1980
gcagccaaaa ccattaattt tggtgtgctg tatggtatga gcgcacatcg cctgtcacag      2040
gaactggcaa ttccgtatga agaagcacag gcctttattg aacgctattt tcagtctttt      2100
ccgaaagttc gcgcatggat tgaaaaaacc ttagaagaag tcgtcgtcg cggctatgtg      2160 gaaaccctgt ttggtcgtcg tcgctatgtt ccggatctgg aagcgagagt taaatcagtg      2220
cgtgaagccg ccgaacgcat ggcctttaat atgccggttc agggaacggc agctgacctt      2280
atgaaactgg caatggttaa actgtttccg cgcctggaag aaatgggtgc acgaatgctg      2340
ttacaggttc atgatgaatt agttctggaa gccccgaaag aacgcgccga agcagttgca      2400
cgtctggcca aagaagtgat ggaaggtgtg tatccgttag cagttccgtt agaagtggaa      2460
gtgggtattg gtgaagattg gctgagcgcc aaagaaggtt ctggcagttc aggtcatcac      2520
caccatcatc actaa                                                       2535
```

<210> SEQ ID NO 20
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
```

```
            145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
                210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Phe Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
                275                 280                 285
Glu Ser Pro Lys Ala Leu Glu Glu Ala Pro Trp Pro Pro Pro Glu Gly
                290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
                370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
                515                 520                 525
Val Glu Lys Ile Leu Gln Tyr Arg Glu Leu Thr Lys Leu Lys Ser Thr
                530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
```

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
    835                 840

<210> SEQ ID NO 21
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag tcgcgcccc gaccccggaa gattttccgc gtcagctggc cttaattaaa    300
gaattagttg acttgctggg cttagcacgt ctggaagttc gggctatga agcagatgat    360 gttttagcct cactgccaa aaagccgaa aagaaggct atgaagttcg cattctgacc    420
gcagataagg atctgtatca gctgctgagc gatcgtattc atgtgttaca tccggaaggc    480

```
tatctgatta ccccggcatg gttatgggaa aaatatggtt tacgtccgga tcagtgggca   540
gattatcgtg cactgaccgg tgacgaatca gataatctgc cgggcgttaa aggtattggt   600
gaaaaaccg cccggaaatt attagaagaa tggggtagtc tggaagcatt actgaaaaat    660
ctggatcgcc tgaaaccggc aattcgcgaa aaaattttag cccacatgga tgacttaaaa   720
ctgtcttggg atctggccaa agtgcgtacc gatctgccgt tagaagttga ttttgccaaa   780
cgtcgcgaac cggatcgtga acgcctacga ttctttctgg aacgcttaga atttggctca   840
ctgttacatg aatttggctt actggaatct ccgaaagcat tagaagaagc cccgtggccg   900
ccgccggaag cgcctttgt gggctttgtg ctgagtagga agaaccgat gtgggcagac     960
ttgctggccc tggccgcagc acgcggcggt cgcgttcatc gtgccccgga accgtacaaa  1020
gccctgcgtg acctgaaaga gcacgcggc ttattagcca aagacctgag tgttctggca   1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
ctggaagttg cagaagaaat tgcacgctta gaagccgaag ttttcgctt agcaggtcat   1440
ccgtttaact aaatagtcg cgatcagctg aaagggttc tgtttgatga attaggcctg    1500
ccggcaattg gcaagaccga aaaaaccggt aaacgctcta cctcagccgc agttctggaa  1560
gccctgcgcg aagcccatcc gattgttgaa aaattttac agtatcgtga actgaccaaa   1620
ctgaaatcta cctatattga tccgttaccg gatctaattc atccgcgtac cggtcgctta  1680
cataccgtt ttaatcagac cgccaccgcc accggtcgct tatcaagtag cgatccgaac   1740
ttgcagaata ttccggtgcg taccccgtta ggtcagcgca ttcgtcgtgc ctttattgca  1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgtcacag  2040
gaactggcaa ttccgtatga agaagcacag gcctttattg aacgctattt tcagtctttt  2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaactgg caatggttaa actgtttccg cgcctggaag aaatgggtgc acgaatgctg  2340
ttacaggttc atgatgaatt agttctggaa gccccgaaag aacgcgccga agcagttgca  2400
cgtctggcca agaagtgat ggaaggtgtg tatccgttag cagttccgtt agaagtggaa   2460
gtgggtattg gtgaagattg gctgagcgcc aaagaaggtt ctggcagttc aggtcatcac  2520
caccatcatc actaa                                                    2535
```

<210> SEQ ID NO 22
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Arg Gly Met Leu Pro Leu Phe Glu Pro Lys Gly Arg Val Leu Leu
1               5                   10                  15
Val Asp Gly His His Leu Ala Tyr Arg Thr Phe His Ala Leu Lys Gly
            20                  25                  30
Leu Thr Thr Ser Arg Gly Glu Pro Val Gln Ala Val Tyr Gly Phe Ala
        35                  40                  45
Lys Ser Leu Leu Lys Ala Leu Lys Glu Asp Gly Asp Ala Val Ile Val
    50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
        115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
        195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Phe Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
        355                 360                 365
Pro Gly Asp Asp Pro Met Leu Leu Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
```

```
Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830
```

Gly Ser Gly Ser Ser Gly His His His His His His
        835                 840

<210> SEQ ID NO 23
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| | |
|---|---|
| atgcgcggta tgctgccgtt atttgaaccg aaaggtcgtg tgctgctggt tgatggtcat | 60 |
| cacttagcat atcgtacctt tcatgccctg aaaggcctga ccacctctcg cggcgaaccg | 120 |
| gttcaggcag tgtatggttt tgccaaatca ctgctgaaag cattaaaaga agatggcgat | 180 |
| gcagtgattg ttgtgtttga tgccaaagcc ccgagctttc gtcatgaagc ctatggcggc | 240 |
| tacaaagcag gtcgcgcccc gacccccgaa gattttccgc gtcagctggc cttaattaaa | 300 |
| gaattagttg acttgctggg cttagcacgt ctggaagttc cgggctatga agcagatgat | 360 |
| gttttagcct cactggccaa aaaagccgaa aagaaggct atgaagttcg cattctgacc | 420 |
| gcagataagg atctgtatca gctgctgagc gatcgtattc atgtgttaca tccggaaggc | 480 |
| tatctgatta ccccggcatg gttatgggaa aaatatggtt acgtccgga tcagtgggca | 540 |
| gattatcgtg cactgaccgg tgacgaatca gataatctgc cggcgttaa aggtattggt | 600 |
| gaaaaaccg cccggaaatt attagaagaa tggggtagtc tggaagcatt actgaaaaat | 660 |
| ctggatcgcc tgaaaccggc aattcgcgaa aaaattttag cccacatgga tgacttaaaa | 720 |
| ctgtcttggg atctggccaa agtgcgtacc gatctgccgt tagaagttga ttttgccaaa | 780 |
| cgtcgcgaac cggatcgtga acgcctacga gcctttctgg aacgcttaga atttggctca | 840 |
| ctgttacatg aatttggctt atctgaatct ccgaaagcat agaagaagc cccgtggccg | 900 |
| ccgccggaag cgccctttgt gggctttgtg ctgagtagga agaaccgat gtgggcagac | 960 |
| ttgctggccc tggccgcagc acgcggcggt cgcgttcatc gtgccccgga accgtacaaa | 1020 |
| gccctgcgtg acctgaaaga agcacgcggc ttattagcca aagacctgag tgttctggca | 1080 |
| ttaagggaag gcttaggcct gccgccgggc gatgatccga tgctgctggc ctatctgctt | 1140 |
| gacccgagta ataccacccc ggaaggcgtt gcacgtcgct atggcggcga gtggaccgaa | 1200 |
| gaagcaggcg aacgtgcagc cctgtcagaa cgtctgtttg ccaatctgtg gggtcgctta | 1260 |
| gaaggcgaag aacgcttact gtggttatat cgtgaagtgg aacgtccgct gagcgcagtg | 1320 |
| ctggcacaca tggaagccac cggtgtgcgc ttagatgttg catatctgcg tgccctgtct | 1380 |
| ctggaagttg cagaagaaat tgcacgctta gaagccgaag tttttcgctt agcaggtcat | 1440 |
| ccgtttaact aaatagtcg cgatcagctg gaaagggttc tgtttgatga attaggcctg | 1500 |
| ccggcaattg gcaagaccga aaaaaccggt aaacgctcta cctcagccgc agttctggaa | 1560 |
| gccctgcgcg aagcccatcc gattgttgaa aaaattttac agtatcgtga actgaccaaa | 1620 |
| ctgaaatcta cctatattga tccgttaccg gatctaattc atccgcgtac cggtcgctta | 1680 |
| cataccccgtt ttaatcagac cgccaccgcc accggtcgct atcaagtag cgatccgaac | 1740 |
| ttgcagaata ttccggtgcg taccccgtta ggtcagcgca ttcgtcgtgc ctttattgca | 1800 |
| gaagaaggtt ggttattagt tgcattagat tatagtcaga ttgaactgcg tgtgttagcc | 1860 |
| catctgagcg gcgacgaaaa tctgattcgt gtgtttcagg aaggtcgcga tattcatacc | 1920 |
| gaaaccgcct cttggatgtt tggtgttccg cgcgaagcag ttgatccgtt aatgcgccgt | 1980 |

```
gcagccaaaa ccattaattt tggtgtgctg tatggtatga gcgcacatcg cctgtcacag    2040
gaactggcaa ttccgtatga agaagcacag gcctttattg aacgctattt tcagtctttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
ttacaggttc atgatgaatt agttctggaa gccccgaaag aacgcgccga agcagttgca    2400
cgtctggcca aagaagtgat ggaaggtgtg tatccgttag cagttccgtt agaagtggaa    2460
gtgggtattg gtgaagattg gctgagcgcc aaagaaggtt ctggcagttc aggtcatcac    2520
caccatcatc actaa                                                    2535
```

<210> SEQ ID NO 24
<211> LENGTH: 844
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255
```

-continued

```
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Ser
        275                 280                 285
Glu Ser Pro Lys Ala Leu Glu Glu Ala Pro Trp Pro Pro Glu Gly
290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
            325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
            405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
            450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
            485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Thr Gly Arg Leu Ser Ser
            565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
            595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
            645                 650                 655
Leu Met Arg Arg Ala Ala Lys Thr Ile Asn Phe Gly Val Leu Tyr Gly
            660                 665                 670
```

Met Ser Ala His Arg Leu Ser Gln Glu Leu Ala Ile Pro Tyr Glu Glu
           675                 680                 685

Ala Gln Ala Phe Ile Glu Arg Tyr Phe Gln Ser Phe Pro Lys Val Arg
       690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
               740                 745                 750

Val Gln Gly Thr Ala Ala Asp Leu Met Lys Leu Ala Met Val Lys Leu
           755                 760                 765

Phe Pro Arg Leu Glu Glu Met Gly Ala Arg Met Leu Leu Gln Val His
       770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
           820                 825                 830

Gly Ser Gly Ser Ser Gly His His His His His
       835                 840

<210> SEQ ID NO 25
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcagtgattg ttgtgtttga tgccaaagcc ccgagctttc gtcatgaagc ctatggcggc     240
tacaaagcag tcgcgccccc gaccccggaa gattttccgc gtcagctggc cttaattaaa     300
gaattagttg acttgctggg cttagcacgt ctggaagttc gggctatga agcagatgat     360 gttttagcct cactgccaa aaagccgaa aagaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt acgtccggga tcagtgggca     540
gattatcgtg cactgaccgg tgacgaatca gataatctgc cgggcgttaa aggtattggt     600
gaaaaaaccg cccggaaatt attagaagaa tggggtagtc tggaagcatt actgaaaaat     660
ctggatcgcc tgaaaccggc aattcgcgaa aaaattttag cccacatgga tgacttaaaa     720
ctgtcttggg atctggccaa agtgcgtacc gatctgccgt agaagttga ttttgccaaa     780 cgtcgcgaac cggatcgtga acgcctacga gcctttctgg aacgcttaga atttggctca     840
ctgttacatg aatttggctt actgaaatct ccgaaagcat agaagaagc cccgtggccg     900 ccgccggaag cgcctttgt gggctttgtg ctgagtagga agaaccgat gtgggcagac     960 ttgctggccc tggccgcagc acgcggcggt cgcgttcatc gtgccccgga accgtacaaa    1020
gccctgcgtg acctgaaaga agcacgcggc ttattagcca agacctgag tgttctggca    1080

```
ttaagggaag gcttaggcct gccgccgggc gatgatccga tgctgctggc ctatctgctt    1140
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
ctggaagttg cagaagaaat tgcacgctta gaagccgaag tttttcgctt agcaggtcat    1440
ccgtttaact aaatagtcg cgatcagctg aaagggttc tgtttgatga attaggcctg      1500
ccggcaattg gcaagaccga aaaaccggt aaacgctcta cctcagccgc agttctggaa     1560
gccctgcgcg aagcccatcc gattgttgaa aaatttttac agtatcgtga actgaccaaa    1620
ctgaaatcta cctatattga tccgttaccg gatctaattc atccgcgtac cggtcgctta    1680 cataccgtt ttaatcagac cgccaccgcc accggtcgct tatcaagtag cgatccgaac     1740
ttgcagaata ttccggtgcg tacccgttta ggtcagcgca ttcgtcgtgc ctttattgca    1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaattt tggtgtgctg tatggtatga gcgcacatcg cctgtcacag    2040
gaactggcaa ttccgtatga agaagcacag gcctttattg aacgctattt tcagtctttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
ttacaggttc atgatgaatt agttctggaa gccccgaaag aacgcgccga agcagttgca    2400
cgtctggcca aagaagtgat ggaaggtgtg tatccgttag cagttccgtt agaagtggaa    2460
gtgggtattg gtgaagattg gctgagcgcc aaagaaggtt ctggcagttc aggtcatcac    2520
caccatcatc actaa                                                    2535

<210> SEQ ID NO 26
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95
```

```
Ala Leu Ile Lys Glu Leu Val Asp Leu Gly Leu Ala Arg Leu Glu
            100                 105                 110

Val Pro Gly Tyr Glu Ala Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Lys Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510
```

```
Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
        835                 840

<210> SEQ ID NO 27
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
```

```
gcagtgattg ttgtgtttga tgccaaagcc ccgagctttc gtcatgaagc ctatggcggc    240
tacaaagcag gtcgcgcccc gacccccggaa gatttttccgc gtcagctggc cttaattaaa    300
gaattagttg acttgctggg cttagcacgt ctggaagttc cgggctatga agcagatgat    360
gttttagcct cactgccaa aaaagccgaa aaagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg cactgaccgg tgacgaatca gataatctgc cgggcgttaa aggtattggt    600 gaaaaaccg cccggaaatt attagaagaa tggggtagtc tggaagcatt actgaaaaat    660
ctggatcgcc tgaaaccggc aattcgcgaa aaaatttttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga agaaccgat gtgggcagac    960 ttgctggccc tggccgcagc acgcggcggt cgcgttcatc gtgccccgga accgtacaaa    1020
gccctgcgtg acctgaaaga agcacgcggc ttattagcca aagacctgat cgttctggca    1080
ttaagggaag gcttaggcct gccgccgggc gatgatccga tgctgctggc ctatctgctt    1140
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
ctggaagttg cagaagaaat tgcacgctta gaagccgaag ttttttcgctt agcaggtcat    1440 ccgtttaact taaatagtcg cgatcagctg gaaagggttc tgtttgatga attaggcctg    1500
ccggcaattg gcaagaccga aaaaaccggt aaacgctcta cctcagccgc agttctggaa    1560
gccctgcgcg aagcccatcc gattgttgaa aaaattttac agtatcgtga actgaccaaa    1620
ctgaaatcta cctatattga tccgttaccg gatctaattc atccgcgtac cggtcgctta    1680 cataccccgtt ttaatcagac cgccaccgcc accggtcgct tatcaagtag cgatccgaac    1740
ttgcagaata ttccggtgcg tacccgtta ggtcagcgca ttcgtcgtgc cttattgca    1800 gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaatt tggtgtgctg tatggtatga gcgcacatcg cctgtcacag    2040
gaactggcaa ttccgtatga agaagcacag gcctttattg aacgctattt tcagtctttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctgaag aaatgggtgc acgaatgctg    2340
ttacaggttc atgatgaatt agttctggaa gccccgaaag aacgcgccga agcagttgca    2400
cgtctggcca aagaagtgat ggaaggtgtg tatccgttag cagttccgtt agaagtggaa    2460
gtgggtattg gtgaagattg gctgagcgcc aaagaaggt ctggcagttc aggtcatcac    2520
```
caccatcatc actaa                                              2535

<210> SEQ ID NO 28
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

```
Ala Lys Asp Leu Ile Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
        740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
```

|  | 770 |  | 775 |  | 780 |  |
|---|---|---|---|---|---|---|

Asp Glu Leu Val Leu Glu Ala Pro Lys Glu Arg Ala Glu Ala Val Ala
785         790             795             800

Arg Leu Ala Lys Glu Val Met Glu Gly Val Tyr Pro Leu Ala Val Pro
        805             810             815

Leu Glu Val Glu Val Gly Ile Gly Glu Asp Trp Leu Ser Ala Lys Glu
            820             825             830

Gly Ser Gly Ser Ser Gly His His His His His His
            835             840

<210> SEQ ID NO 29
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

| atgcgcggta tgctgccgtt atttgaaccg aaaggtcgtg tgctgctggt tgatggtcat | 60 |
|---|---|
| cacttagcat atcgtacctt tcatgccctg aaaggcctga ccacctctcg cggcgaaccg | 120 |
| gttcaggcag tgtatggttt tgccaaatca ctgctgaaag cattaaaaga agatggcgat | 180 |
| gcagtgatta ttgtgtttga tgccaaagcc ccgagctttc gtcatgaagc ctatggcggc | 240 |
| tacaaagcag gtcgcgcccc gaccccggaa gattttccgc gtcagctggc cttaattaaa | 300 |
| gaattagttg acttgctggg cttagcacgt ctggaagttc cgggctatga agcagatgat | 360 |
| gttttagcct cactggccaa aaaagccgaa aagaaggct atgaagttcg cattctgacc | 420 |
| gcagataagg atctgtatca gctgctgagc gatcgtattc atgtgttaca tccggaaggc | 480 |
| tatctgatta ccccggcatg gttatgggaa aaatatggtt acgtccgga tcagtgggca | 540 |
| gattatcgtg cactgaccgg tgacgaatca gataatctgc cggcgttaa aggtattggt | 600 |
| gaaaaaaccg cccggaaatt attagaagaa tggggtagtc tggaagcatt actgaaaaat | 660 |
| ctggatcgcc tgaaaccggc aattcgcgaa aaaatttag cccacatgga tgacttaaaa | 720 |
| ctgtcttggg atctggccaa agtgcgtacc gatctgccgt tagaagttga ttttgccaaa | 780 |
| cgtcgcgaac cggatcgtga acgcctacga gcctttctgg aacgcttaga atttggctca | 840 |
| ctgttacatg aatttggctt actggaatct ccgaaagcat agaagaagc cccgtggccg | 900 |
| ccgccggaag cgcctttgt gggctttgtg ctgagtagga agaaccgat gtgggcagac | 960 |
| ttgctggccc tggccgcagc acgcggcggt cgcgttcatc gtgccccgga accgtacaaa | 1020 |
| gccctgcgtg acctgaaaga agcacgcggc ttattagcca agacctgag tgttctggca | 1080 |
| tctagggaag gcttaggcct gccgccgggc gatgatccga tgctgctggc ctatctgctt | 1140 |
| gacccgagta ataccacccc ggaaggcgtt gcacgtcgct atggcggcga gtggaccgaa | 1200 |
| gaagcaggcg aacgtgcagc cctgtcagaa cgtctgtttg ccaatctgtg ggtcgctta | 1260 |
| gaaggcgaag aacgcttact gtggttatat cgtgaagtgg aacgtccgct gagcgcagtg | 1320 |
| ctggcacaca tggaagccac cggtgtgcgc ttagatgttg catatctgcg tgccctgtct | 1380 |
| ctggaagttg cagaagaaat tgcacgctta gaagccgaag ttttcgctt agcaggtcat | 1440 |
| ccgtttaact taaatagtcg cgatcagctg gaagggttc tgtttgatga attaggcctg | 1500 |
| ccggcaattg gcaagaccga aaaaccggt aaacgctcta cctcagccgc agttctggaa | 1560 |
| gccctgcgcg aagcccatcc gattgttgaa aaaatttac agtatcgtga actgaccaaa | 1620 |

-continued

```
ctgaaatcta cctatattga tccgttaccg gatctaattc atccgcgtac cggtcgctta    1680 cataccegtt ttaatcagac cgccaccgcc accggtcgct tatcaagtag cgatccgaac    1740
ttgcagaata ttccggtgcg taccccgtta ggtcagcgca ttcgtcgtgc ctttattgca    1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaattt tggtgtgctg tatggtatga gcgcacatcg cctgtcacag    2040
gaactggcaa ttccgtatga agaagcacag gcctttattg aacgctattt tcagtctttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
ttacaggttc atgatgaatt agttctggaa gccccgaaag aacgcgccga agcagttgca    2400
cgtctggcca agaagtgat ggaaggtgtg tatccgttag cagttccgtt agaagtggaa    2460
gtgggtattg gtgaagattg gctgagcgcc aaagaaggtt ctggcagttc aggtcatcac    2520
caccatcatc actaa                                                     2535
```

<210> SEQ ID NO 30
<211> LENGTH: 844
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190
```

```
Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
```

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His His
    835                 840

<210> SEQ ID NO 31
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga gatggcgat      180 gcagtgattg ttgtgtttga tgccaaagcc ccgagctttc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc gggctatga agcagatgat     360 gttttagcct cactggccaa aaaagccgaa aagaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt acgtccgga tcagtgggca     540 gattatcgtg cactgaccgg tgacgaatca gataatctgc cggcgttaa aggtattggt     600 gaaaaaaccg cccggaaatt attagaagaa tggggtagtc tggaagcatt actgaaaaat     660
ctggatcgcc tgaaaccggc aattcgcgaa aaaatttag cccacatgga tgacttaaaa     720

```
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag cgcctttgt gggctttgtg ctgagtagga agaaccgat gtgggcagac      960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag gcttaggcct gccgccgggc gatgatccga tgctgtctgc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttcgctt agcaggtcat    1440
ccgtttaact aaatagtcg cgatcagctg gaaagggttc tgtttgatga attaggcctg    1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct tatcaagtag cgatccgaac   1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca agaagtgat ggaaggtgtg tatccgttag cagttccgtt agaagtggaa    2460
gtgggtattg gtgaagattg gctgagcgcc aaagaaggtt ctggcagttc aggtcatcac   2520
caccatcatc actaa                                                    2535
```

<210> SEQ ID NO 32
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

```
Leu Thr Thr Ser Arg Gly Glu Pro Val Gln Ala Val Tyr Gly Phe Ala
        35                  40                  45
Lys Ser Leu Leu Lys Ala Leu Lys Glu Asp Gly Asp Ala Val Ile Val
 50                  55                  60
Val Phe Asp Ala Lys Ala Pro Ser Phe Arg His Glu Ala Tyr Gly Gly
 65                  70                  75                  80
Tyr Lys Ala Gly Arg Ala Pro Thr Pro Glu Asp Phe Pro Arg Gln Leu
                 85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
        115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
        195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
        355                 360                 365
Pro Gly Asp Asp Pro Met Leu Ser Ala Tyr Leu Leu Asp Pro Ser Asn
    370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
        435                 440                 445
Val Arg Leu Asp Val Ala Tyr Leu Arg Ala Leu Ser Leu Glu Val Ala
```

```
              450                 455                 460
Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

Gly Ser Gly Ser Ser Gly His His His His His
            835                 840

<210> SEQ ID NO 33
<211> LENGTH: 2535
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 33

| | |
|---|---:|
| atgcgcggta tgctgccgtt atttgaaccg aaaggtcgtg tgctgctggt tgatggtcat | 60 |
| cacttagcat atcgtacctt tcatgccctg aaaggcctga ccacctctcg cggcgaaccg | 120 |
| gttcaggcag tgtatggttt tgccaaatca ctgctgaaag cattaaaaga agatggcgat | 180 |
| gcagtgattg ttgtgtttga tgccaaagcc ccgagctttc gtcatgaagc ctatggcggc | 240 |
| tacaaagcag gtcgcgcccc gacccccgaa gattttccgc gtcagctggc cttaattaaa | 300 |
| gaattagttg acttgctggg cttagcacgt ctggaagttc cgggctatga agcagatgat | 360 |
| gttttagcct cactggccaa aaaagccgaa aagaaggct atgaagttcg cattctgacc | 420 |
| gcagataagg atctgtatca gctgctgagc gatcgtattc atgtgttaca tccggaaggc | 480 |
| tatctgatta ccccggcatg gttatgggaa aaatatggtt tacgtccgga tcagtgggca | 540 |
| gattatcgtg cactgaccgg tgacgaatca gataatctgc cggcgttaa aggtattggt | 600 |
| gaaaaaaccg cccggaaatt attagaagaa tggggtagtc tggaagcatt actgaaaaat | 660 |
| ctggatcgcc tgaaaccggc aattcgcgaa aaaattttag cccacatgga tgacttaaaa | 720 |
| ctgtcttggg atctggccaa agtgcgtacc gatctgccgt tagaagttga ttttgccaaa | 780 |
| cgtcgcgaac cggatcgtga acgcctacga gcctttctgg aacgcttaga atttggctca | 840 |
| ctgttacatg aatttggctt actggaatct ccgaaagcat tagaagaagc cccgtggccg | 900 |
| ccgccggaag gcgcctttgt gggctttgtg ctgagtagga agaaccgat gtgggcagac | 960 |
| ttgctggccc tggccgcagc acgcggcggt cgcgttcatc gtgccccgga accgtacaaa | 1020 |
| gccctgcgtg acctgaaaga agcacgcggc ttattagcca aagacctgag tgttctggca | 1080 |
| ttaagggaag gcttaggcct gccgccgggc gatgatccga tgctgctggc ctatctgctt | 1140 |
| gacggtagta ataccacccc ggaaggcgtt gcacgtcgct atggcggcga gtggaccgaa | 1200 |
| gaagcaggcg aacgtgcagc cctgtcagaa cgtctgtttg ccaatctgtg gggtcgctta | 1260 |
| gaaggcgaag aacgcttact gtggttatat cgtgaagtgg aacgtccgct gagcgcagtg | 1320 |
| ctggcacaca tggaagccac cggtgtgcgc ttagatgttg catatctgcg tgccctgtct | 1380 |
| ctggaagttg cagaagaaat tgcacgctta gaagccgaag tttttcgctt agcaggtcat | 1440 |
| ccgtttaact aaatagtcg cgatcagctg gaaagggttc tgtttgatga attaggcctg | 1500 |
| ccggcaattg gcaagaccga aaaaaccggt aaacgctcta cctcagccgc agttctggaa | 1560 |
| gccctgcgcg aagcccatcc gattgttgaa aaaattttac agtatcgtga actgaccaaa | 1620 |
| ctgaaatcta cctatattga tccgttaccg gatctaattc atccgcgtac cggtcgctta | 1680 |
| cataccgtt ttaatcagac cgccaccgcc accggtcgct tatcaagtag cgatccgaac | 1740 |
| ttgcagaata ttccggtgcg taccccgtta ggtcagcgca ttcgtcgtgc ctttattgca | 1800 |
| gaagaaggtt ggttattagt tgcattagat tatagtcaga ttgaactgcg tgtgttagcc | 1860 |
| catctgagcg gcgacgaaaa tctgattcgt gtgtttcagg aaggtcgcga tattcatacc | 1920 |
| gaaaccgcct cttggatgtt tggtgttccg cgcgaagcag ttgatccgtt aatgcgccgt | 1980 |
| gcagccaaaa ccattaattt tggtgtgctg tatggtatga gcgcacatcg cctgtcacag | 2040 |
| gaactggcaa ttccgtatga agaagcacag gcctttattg aacgctattt tcagtctttt | 2100 |
| ccgaaagttc gcgcatggat tgaaaaaacc ttagaagaag tcgtcgtcg cggctatgtg | 2160 |
| gaaaccctgt ttggtcgtcg tcgctatgtt ccggatctgg aagcgagagt taaatcagtg | 2220 |

```
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
ttacaggttc atgatgaatt agttctggaa gccccgaaag aacgcgccga agcagttgca    2400
cgtctggcca aagaagtgat ggaaggtgtg tatccgttag cagttccgtt agaagtggaa    2460
gtgggtattg gtgaagattg gctgagcgcc aaagaaggtt ctggcagttc aggtcatcac    2520
caccatcatc actaa                                                    2535
```

<210> SEQ ID NO 34
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
```

```
                290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Gly Ser Asn
                370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
                450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
                500                 505                 510
Ser Thr Ser Ala Ala Val Leu Glu Ala Leu Arg Glu Ala His Pro Ile
                515                 520                 525
Val Glu Lys Ile Leu Gln Tyr Arg Glu Leu Thr Lys Leu Lys Ser Thr
                530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
                580                 585                 590
Arg Ile Arg Arg Ala Phe Ile Ala Glu Glu Gly Trp Leu Leu Val Ala
                595                 600                 605
Leu Asp Tyr Ser Gln Ile Glu Leu Arg Val Leu Ala His Leu Ser Gly
                610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
                660                 665                 670
Met Ser Ala His Arg Leu Ser Gln Glu Leu Ala Ile Pro Tyr Glu Glu
                675                 680                 685
Ala Gln Ala Phe Ile Glu Arg Tyr Phe Gln Ser Phe Pro Lys Val Arg
                690                 695                 700
Ala Trp Ile Glu Lys Thr Leu Glu Glu Gly Arg Arg Gly Tyr Val
705                 710                 715                 720
```

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His His
        835                 840

<210> SEQ ID NO 35
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcagtgattg ttgtgtttga tgccaaagcc ccgagctttc gtcatgaagc ctatggcggc     240
tacaaagcag tcgcgccccc gaccccggaa gattttccgc gtcagctggc cttaattaaa     300
gaattagttg acttgctggg cttagcacgt ctggaagttc gggctatga agcagatgat     360 gttttagcct cactgccaa aaagccgaa aaagaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt acgtccgga tcagtgggca     540 gattatcgtg cactgaccgg tgacgaatca gataatctgc cgggcgttaa aggtattggt     600
gaaaaaaccg cccggaaatt attagaagaa tggggtagtc tggaagcatt actgaaaaat     660
ctggatcgcc tgaaaccggc aattcgcgaa aaaatttag cccacatgga tgacttaaaa     720
ctgtcttggg atctggccaa agtgcgtacc gatctgccgt tagaagttga ttttgccaaa     780
cgtcgcgaac cggatcgtga acgcctacga gcctttctgg aacgcttaga atttggctca     840
ctgttacatg aatttggctt actggaatct ccgaaagcat tagaagaagc cccgtggccg     900
ccgccggaag gcgcctttgt gggctttgtg ctgagtagga agaaccgat gtgggcagac     960 ttgctggccc tggccgcagc acgcggcggt cgcgttcatc gtgccccgga accgtacaaa    1020
gccctgcgtg acctgaaaga agcacgcggc ttattagcca aagacctgag tgttctggca    1080
ttaagggaag gcttaggcct gccgccgggc gatgatccga tgctgctggc ctatctgctt    1140
gacccgagta atatcacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320

```
ctggcacaca tggaagccac cggtgtgcgc ttagatgttg catatctgcg tgccctgtct   1380
ctggaagttg cagaagaaat tgcacgctta gaagccgaag tttttcgctt agcaggtcat   1440
ccgtttaact taaatagtcg cgatcagctg gaaagggttc tgtttgatga attaggcctg   1500
ccggcaattg gcaagaccga aaaaaccggt aaacgctcta cctcagccgc agttctggaa   1560
gccctgcgcg aagcccatcc gattgttgaa aaatttttac agtatcgtga actgaccaaa   1620
ctgaaatcta cctatattga tccgttaccg gatctaattc atccgcgtac cggtcgctta   1680 catcccgtt  ttaatcagac cgccaccgcc accggtcgct atcaagtagc gatccgaac    1740 ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                    2535
```

<210> SEQ ID NO 36
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
```

```
            130                 135                 140
Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Ile Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560
```

```
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
        595                 600                 605
Leu Asp Tyr Ser Gln Ile Glu Leu Arg Val Leu Ala His Leu Ser Gly
    610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
        675                 680                 685
Ala Gln Ala Phe Ile Glu Arg Tyr Phe Gln Ser Phe Pro Lys Val Arg
    690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
        755                 760                 765
Phe Pro Arg Leu Glu Glu Met Gly Ala Arg Met Leu Leu Gln Val His
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
            820                 825                 830
Gly Ser Gly Ser Ser Gly His His His His His His
        835                 840

<210> SEQ ID NO 37
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atgcgcggta tgctgccgtt atttgaaccg aaaggtcgtg tgctgctggt tgatggtcat     60
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag tcgcgccccc gacccccgaa gattttccgc gtcagctggc cttaattaaa    300
gaattagttg acttgctggg cttagcacgt ctggaagttc cgggctatga agcagatgat    360
gttttagcct cactggccaa aaaagccgaa aagaaggct atgaagttcg cattctgacc    420
```

```
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg cactgaccgg tgacgaatca gataatctgc cgggcgttaa aggtattggt    600
gaaaaaaccg cccggaaatt attagaagaa tggggtagtc tggaagcatt actgaaaaat    660
ctggatcgcc tgaaaccggc aattcgcgaa aaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga agaaccgat gtgggcagac    960 ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gcctcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttttcgctt agcaggtcat   1440 ccgtttaact aaatagtcg cgatcagctg gaaagggttc tgtttgatga attaggcctg   1500
ccggcaattg gcaagaccga aaaaaccggt aaacgctcta cctcagccgc agttctggaa   1560
gccctgcgcg aagcccatcc gattgttgaa aaattttac agtatcgtga actgaccaaa   1620
ctgaaatcta cctatattga tccgttaccg gatctaattc atccgcgtac cggtcgctta   1680 cataccgtt ttaatcagac cgccaccgcc accggtcgct tatcaagtag cgatccgaac   1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag tcgtcgtcg cggctatgtg   2160 gaaaccctgt ttggtcgtcg tcgctatgtt ccggatctgg aagcgagagt aaatcagtg   2220 cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca agaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                    2535
```

<210> SEQ ID NO 38
<211> LENGTH: 844
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 38

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400
```

```
Glu Ala Gly Glu Arg Ala Ala Leu Ser Glu Arg Leu Phe Ala Asn Leu
                405                 410                 415

Trp Pro Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815
```

Leu Glu Val Glu Val Gly Ile Gly Glu Asp Trp Leu Ser Ala Lys Glu
                820                 825                 830

Gly Ser Gly Ser Ser Gly His His His His His His
            835                 840

<210> SEQ ID NO 39
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

| | | |
|---|---|---|
| atgcgcggta tgctgccgtt atttgaaccg aaaggtcgtg tgctgctggt tgatggtcat | | 60 |
| cacttagcat atcgtacctt tcatgccctg aaaggcctga ccacctctcg cggcgaaccg | | 120 |
| gttcaggcag tgtatggttt tgccaaatca ctgctgaaag cattaaaaga agatggcgat | | 180 |
| gcagtgattg ttgtgtttga tgccaaagcc ccgagctttc gtcatgaagc ctatggcggc | | 240 |
| tacaaagcag gtcgcgcccc gacccccgaa gattttccgc gtcagctggc cttaattaaa | | 300 |
| gaattagttg acttgctggg cttagcacgt ctggaagttc gggctatga agcagatgat | | 360 |
| gttttagcct cactggccaa aaaagccgaa aagaaggct atgaagttcg cattctgacc | | 420 |
| gcagataagg atctgtatca gctgctgagc gatcgtattc atgtgttaca tccgaaggc | | 480 |
| tatctgatta ccccggcatg gttatgggaa aaatatggtt tacgtccgga tcagtgggca | | 540 |
| gattatcgtg cactgaccgg tgacgaatca gataatctgc cggcgttaa aggtattggt | | 600 |
| gaaaaaaccg cccggaaatt attagaagaa tggggtagtc tggaagcatt actgaaaaat | | 660 |
| ctggatcgcc tgaaaccggc aattcgcgaa aaaattttag cccacatgga tgacttaaaa | | 720 |
| ctgtcttggg atctggccaa agtgcgtacc gatctgccgt tagaagttga ttttgccaaa | | 780 |
| cgtcgcgaac cggatcgtga acgcctacga gcctttctgg aacgcttaga atttggctca | | 840 |
| ctgttacatg aatttggctt actggaatct ccgaaagcat agaagaagc cccgtggccg | | 900 |
| ccgccggaag cgccctttgt gggctttgtg ctgagtagga agaaccgat gtgggcagac | | 960 |
| ttgctggccc tggccgcagc acgcggcggt cgcgttcatc gtgccccgga accgtacaaa | | 1020 |
| gccctgcgtg acctgaaaga agcacgcggc ttattagcca aagacctgag tgttctggca | | 1080 |
| ttaagggaag gcttaggcct gccgccgggc gatgatccga tgctgctggc ctatctgctt | | 1140 |
| gacccgagta ataccacccc ggaaggcgtt gcacgtcgct atggcggcga gtggaccgaa | | 1200 |
| gaagcaggcg aacgtgcagc cctgtcagaa cgtctgtttg ccaatctgtg gggtgactta | | 1260 |
| gaaggcgaag aacgcttact gtggttatat cgtgaagtgg aacgtccgct gagcgcagtg | | 1320 |
| ctggcacaca tggaagccac cggtgtgcgc ttagatgttg catatctgcg tgccctgtct | | 1380 |
| ctggaagttg cagaagaaat tgcacgctta gaagccgaag ttttcgctt agcaggtcat | | 1440 |
| ccgtttaact aaatagtcg cgatcagctg gaaagggttc tgtttgatga attaggcctg | | 1500 |
| ccggcaattg gcaagaccga aaaaaccggt aaacgctcta cctcagccgc agttctggaa | | 1560 |
| gccctgcgcg aagcccatcc gattgttgaa aaaattttac agtatcgtga actgaccaaa | | 1620 |
| ctgaaatcta cctatattga tccgttaccg gatctaattc atccgcgtac cggtcgctta | | 1680 |
| cataccccgtt taatcagac cgccaccgcc accggtcgct atcaagtag cgatccgaac | | 1740 |
| ttgcagaata ttccggtgcg taccccgtta ggtcagcgca ttcgtcgtgc ctttattgca | | 1800 |
| gaagaaggtt ggtattagt tgcattagat tatagtcaga ttgaactgcg tgtgttagcc | | 1860 |

```
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                   2535
```

<210> SEQ ID NO 40
<211> LENGTH: 844
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240
```

-continued

```
Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Asp Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655
```

```
Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
        835                 840

<210> SEQ ID NO 41
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcagtgattg ttgtgtttga tgccaaagcc ccgagctttc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc gggctatga agcagatgat     360 gttttagcct cactggccaa aaaagccgaa aagaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt acgtccgga tcagtgggca     540 gattatcgtg cactgaccgg tgacgaatca gataatctgc cggcgttaa aggtattggt     600 gaaaaaaccg cccggaaatt attagaagaa tggggtagtc tggaagcatt actgaaaaat     660
ctggatcgcc tgaaaccggc aattcgcgaa aaaattttag cccacatgga tgacttaaaa     720
ctgtcttggg atctggccaa agtgcgtacc gatctgccgt tagaagttga ttttgccaaa     780
cgtcgcgaac cggatcgtga acgcctacga gcctttctgg aacgcttaga atttggctca     840
ctgttacatg aatttggctt actggaatct ccgaaagcat tagaagaagc cccgtggccg     900
ccgccggaag gcgccttgt gggctttgt ctgagtagga aagaaccgat gtgggcagac     960
```

-continued

```
ttgctggccc tggccgcagc acgcggcggt cgcgttcatc gtgccccgga accgtacaaa    1020
gccctgcgtg acctgaaaga agcacgcggc ttattagcca aagacctgag tgttctggca    1080
ttaagggaag gcttaggcct gccgccgggc gatgatccga tgctgctggc ctatctgctt    1140
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
aaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
ctggaagttg cagaagaaat tgcacgctta aagccgaag ttttcgctt agcaggtcat     1440 ccgtttaact aaatagtcg cgatcagctg gaaagggttc tgtttgatga attaggcctg     1500
ccggcaattg gcaagaccga aaaaaccggt aaacgctcta cctcagccgc agttctggaa    1560
gccctgcgcg aagcccatcc gattgttgaa aaaattttac agtatcgtga actgaccaaa    1620
ctgaaatcta cctatattga tccgttaccg gatctaattc atccgcgtac cggtcgctta    1680
catacccgtt taatcagac cgccaccgcc accggtcgct atcaagtag cgatccgaac     1740 ttgcagaata ttccggtgcg taccccgtta ggtcagcgca ttcgtcgtgc ctttattgca    1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaattt tggtgtgctg tatggtatga gcgcacatcg cctgtcacag    2040
gaactggcaa ttccgtatga agaagcacag gcctttattg aacgctattt tcagtctttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctggaaa aaatgggtgc acgaatgctg    2340
ttacaggttc atgatgaatt agttctggaa gccccgaaag aacgcgccga agcagttgca    2400
cgtctggcca aagaagtgat ggaaggtgtg tatccgttag cagttccgtt agaagtggaa    2460
gtgggtattg gtgaagattg gctgagcgcc aaagaaggtt ctggcagttc aggtcatcac    2520
caccatcatc actaa                                                    2535
```

<210> SEQ ID NO 42
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

```
Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Lys Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495
```

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Thr Gly Arg Leu Ser Ser
                565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
            835                 840

<210> SEQ ID NO 43
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atgcgcggta tgctgccgtt atttgaaccg aaaggtcgtg tgctgctggt tgatggtcat      60

```
cacttagcat atcgtacctt tcatgccctg aaaggcctga ccacctctcg cggcgaaccg    120
gttcaggcag tgtatggttt tgccaaatca ctgctgaaag cattaaaaga agatggcgat    180
gcagtgattg ttgtgtttga tgccaaagcc ccgagctttc gtcatgaagc ctatggcggc    240
tacaaagcag gtcgcgcccc gaccccggaa gattttccgc gtcagctggc cttaattaaa    300
gaattagttg acttgctggg cttagcacgt ctggaagttc cgggctatga agcagatgat    360
gttttagcct cactgccaaa aaagccgaaa aagaaggct atgaagttcg cattctgacc    420
gcagataagg atctgtatca gctgctgagc gatcgtattc atgtgttaca tccggaaggc    480
tatctgatta ccccggcatg gttatgggaa aaatatggtt tacgtccgga tcagtgggca    540
gattatcgtg cactgaccgg tgacgaatca gataatctgc cgggcgttaa aggtattggt    600
gaaaaaccg cccggaaatt attagaagaa tggggtagtc tggaagcatt actgaaaaat    660
ctggatcgcc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgccttgt gggctttgtg ctgagtagga agaaccgat gtgggcagac    960
ttgctggccc tggccgcagc acgcggcggt cgcgttcatc gtgccccgga accgtacaaa   1020
gccctgcgtg acctgaaaga agcacgcggc ttattagcca aagacctgag tgttctggca   1080
ttaaggggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
tctgaagttg cagaagaaat tgcacgctta gaagccgaag tttttcgctt agcaggtcat   1440
ccgtttaact aaatagtcg cgatcagctg gaaagggttc tgtttgatga attaggcctg   1500
ccggcaattg gcaagaccga aaaaccggt aaacgctcta cctcagccgc agttctggaa   1560
gccctgcgcg aagcccatcc gattgttgaa aaaatttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct tatcaagtag cgatccgaac   1740
ttgcagaata ttccggtgcg tacccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctgaa gccccgaaag aacgcgccga agcagttgca   2400
cgtctggcca agaagtgat ggaaggtgtg tatccgttag cagttccgtt agaagtggaa   2460
```

```
gtgggtattg gtgaagattg gctgagcgcc aaagaaggtt ctggcagttc aggtcatcac   2520
caccatcatc actaa                                                    2535
```

<210> SEQ ID NO 44
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335
```

```
Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Ser Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
```

|     |     |     | 755 |     |     |     | 760 |     |     |     | 765 |     |     |
| --- | --- | --- | --- | --- | --- | --- | --- | --- | --- | --- | --- | --- | --- |
| Phe | Pro | Arg | Leu | Glu | Glu | Met | Gly | Ala | Arg | Met | Leu | Leu | Gln | Val | His |
|     |     |     | 770 |     |     |     | 775 |     |     |     | 780 |     |     |

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                    805                 810                 815

Leu Glu Val Glu Val Gly Ile Gly Glu Asp Trp Leu Ser Ala Lys Glu
            820                 825                 830

Gly Ser Gly Ser Ser Gly His His His His His His
            835                 840

<210> SEQ ID NO 45
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atgcgcggta tgctgccgtt atttgaaccg aaaggtcgtg tgctgctggt tgatggtcat        60
cacttagcat atcgtacctt tcatgccctg aaaggcctga ccacctctcg cggcgaaccg       120
gttcaggcag tgtatggttt tgccaaatca ctgctgaaag cattaaaaga gatggcgat       180 gcagtgattg ttgtgtttga tgccaaagcc ccgagctttc gtcatgaagc ctatgcggc       240 tacaaagcag gtcgcgcccc gaccccggaa gattttccgc gtcagctggc cttaattaaa       300
gaattagttg acttgctggg cttagcacgt ctggaagttc cgggctatga gcagatgat       360 gttttagcct cactggccaa aaaagccgaa aagaaggct atgaagttcg cattctgacc       420
gcagataagg atctgtatca gctgctgagc gatcgtattc atgtgttaca tccggaaggc       480
tatctgatta ccccggcatg gttatgggaa aaatatggtt acgtccgga tcagtgggca       540 gattatcgtg cactgaccgg tgacgaatca gataatctgc cgggcgttaa aggtattggt       600
gaaaaaaccg cccggaaatt attagaagaa tggggtagtc tggaagcatt actgaaaaat       660
ctggatcgcc tgaaaccggc aattcgcgaa aaaattttag cccacatgga tgacttaaaa       720
ctgtcttggg atctggccaa agtgcgtacc gatctgccgt tagaagttga ttttgccaaa       780
cgtcgcgaac cggatcgtga acgcctacga gcctttctgg aacgcttaga atttggctca       840
ctgttacatg aatttggctt actggaatct ccgaaagcat agaagaagc cccgtggccg       900 ccgccggaag gcgcctttgt gggctttgtg ctgagtagga agaaccgat gtgggcagac       960 ttgctggccc tggccgcagc acgcggcggt cgcgttcatc gtgccccgga accgtacaaa      1020
gccctgcgtg acctgaaaga agcacgcggc ttattagcca aagacctgag tgttctggca      1080
ttaagggaag gcttaggcct gccgccgggc gatgatccga tgctgctggc ctatctgctt      1140
gacccgagta ataccacccc ggaaggcgtt gcacgtcgct atggcggcga gtggaccgaa      1200
gaagcaggcg aacgtgcagc cctgtcagaa cgtctgtttg ccaatctgtg gggtcgctta      1260
gaaggcgaag aacgcttact gtggttatat cgtgaagtgg aacgtccgct gagcgcagtg      1320
ctggcacaca tggaagccac cggtgtgcgc ttagatgttg catatctgcg tgccctgtct      1380
ctggaagttg cagaagaaat tgcacgctta gaattcgaag tttttcgctt agcaggtcat      1440
ccgtttaact aaatagtcg cgatcagctg gaaagggttc tgtttgatga attaggcctg      1500
ccggcaattg gcaagaccga aaaaaccggt aaacgctcta cctcagccgc agttctggaa      1560

-continued

```
gccctgcgcg aagcccatcc gattgttgaa aaaattttac agtatcgtga actgaccaaa    1620
ctgaaatcta cctatattga tccgttaccg gatctaattc atccgcgtac cggtcgctta    1680
catacccgtt ttaatcagac cgccaccgcc accggtcgct tatcaagtag cgatccgaac    1740
ttgcagaata ttccggtgcg tacccgtta  ggtcagcgca ttcgtcgtgc ctttattgca    1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaattt tggtgtgctg tatggtatga gcgcacatcg cctgtcacag    2040
gaactggcaa ttccgtatga agaagcacag gcctttattg aacgctattt tcagtctttt    2100
ccgaaagttc gcgcatggat tgaaaaaacc ttagaagaag gtcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
ttacaggttc atgatgaatt agttctggaa gccccgaaag aacgcgccga agcagttgca    2400
cgtctggcca agaagtgat  ggaaggtgtg tatccgttag cagttccgtt agaagtggaa    2460
gtgggtattg gtgaagattg gctgagcgcc aaagaaggtt ctggcagttc aggtcatcac    2520
caccatcatc actaa                                                    2535
```

<210> SEQ ID NO 46
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175
```

-continued

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Phe Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala

```
                     595                 600                 605
Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
        835                 840

<210> SEQ ID NO 47
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcagtgattg ttgtgtttga tgccaaagcc ccgagctttc gtcatgaagc ctatggcggc     240
tacaaagcag gtcgcgcccc gacccccgaa gattttccgc gtcagctggc cttaattaaa     300
gaattagttg acttgctggg cttagcacgt ctggaagttc gggctatga agcagatgat     360 gttttagcct cactgccaa aaagccgaa aagaaggct atgaagttcg cattctgacc         420
gcagataagg atctgtatca gctgctgagc gatcgtattc atgtgttaca tccggaaggc      480
tatctgatta ccccggcatg gttatgggaa aaatatggtt acgtccgga tcagtgggca      540 gattatcgtg cactgaccgg tgacgaatca gataatctgc cggcgttaa aggtattggt       600 gaaaaaaccg cccggaaatt attagaagaa tggggtagtc tggaagcatt actgaaaaat      660
```

```
ctggatcgcc tgaaaccggc aattcgcgaa aaaattttag cccacatgga tgacttaaaa    720
ctgtcttggg atctggccaa agtgcgtacc gatctgccgt tagaagttga ttttgccaaa    780
cgtcgcgaac cggatcgtga acgcctacga gcctttctgg aacgcttaga atttggctca    840
ctgttacatg aatttggctt actggaatct ccgaaagcat tagaagaagc cccgtggccg    900
ccgccggaag gcgcctttgt gggctttgtg ctgagtagga agaaccgat gtgggcagac     960
ttgctggccc tggccgcagc acgcggcggt cgcgttcatc gtgccccgga accgtacaaa   1020
gccctgcgtg acctgaaaga agcacgcggc ttattagcca agacctgag tgttctggca    1080
ttaagggaag gcttaggcct gccgccgggc gatgatccga tgctgctggc ctatctgctt   1140
gacccgagta ataccacccc ggaaggcgtt gcacgtcgct atggcggcga gtggaccgaa   1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg   1320
ctggcacaca tggaagccac cggtgtgcgc ttagatgttg catatctgcg tgccctgtct   1380
ctggaagttg cagaagaaat tgcacgctta gaagccgaag ttttcgctt agcaggtcat    1440
ccgtttaact aaatagtcg cgatcagctg gaaagggttc tgtttgataa attaggcctg    1500
ccggcaattg gcaagaccga aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct atcaagtag cgatccgaac   1740
ttgcagaata ttccggtgcg tacccgtta ggtcagcgca ttcgtcgtgc ctttattgca    1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag tcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca agaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                     2535
```

<210> SEQ ID NO 48
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Arg Gly Met Leu Pro Leu Phe Glu Pro Lys Gly Arg Val Leu Leu
1               5                   10                  15

```
Val Asp Gly His His Leu Ala Tyr Arg Thr Phe His Ala Leu Lys Gly
             20                  25                  30

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
        340                 345                 350

Ala Lys Asp Leu Ser Val Leu Ala Leu Arg Glu Gly Leu Gly Leu Pro
    355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
        420                 425                 430

Val Glu Arg Pro Leu Ser Ala Val Leu Ala His Met Glu Ala Thr Gly
```

435                 440                 445
Val Arg Leu Asp Val Ala Tyr Leu Arg Ala Leu Ser Leu Glu Val Ala
450                 455                 460

Glu Glu Ile Ala Arg Leu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Lys Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
                515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
                675                 680                 685

Ala Gln Ala Phe Ile Glu Arg Tyr Phe Gln Ser Phe Pro Lys Val Arg
                690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
                755                 760                 765

Phe Pro Arg Leu Glu Glu Met Gly Ala Arg Met Leu Leu Gln Val His
                770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

Gly Ser Gly Ser Ser Gly His His His His His
                835                 840

<210> SEQ ID NO 49

<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

| | |
|---|---|
| atgcgcggta tgctgccgtt atttgaaccg aaaggtcgtg tgctgctggt tgatggtcat | 60 |
| cacttagcat atcgtacctt tcatgccctg aaaggcctga ccacctctcg cggcgaaccg | 120 |
| gttcaggcag tgtatggttt tgccaaatca ctgctgaaag cattaaaaga agatggcgat | 180 |
| gcagtgattg ttgtgtttga tgccaaagcc ccgagctttc gtcatgaagc ctatggcggc | 240 |
| tacaaagcag gtcgcgcccc gaccccggaa gattttccgc gtcagctggc cttaattaaa | 300 |
| gaattagttg acttgctggg cttagcacgt ctggaagttc cgggctatga agcagatgat | 360 |
| gttttagcct cactggccaa aaaagccgaa aagaaggct atgaagttcg cattctgacc | 420 |
| gcagataagg atctgtatca gctgctgagc gatcgtattc atgtgttaca tccggaaggc | 480 |
| tatctgatta cccggcatg gttatgggaa aaatatggtt acgtccgga tcagtgggca | 540 |
| gattatcgtg cactgaccgg tgacgaatca gataatctgc cggcgttaa aggtattggt | 600 |
| gaaaaaaccg cccggaaatt attagaagaa tggggtagtc tggaagcatt actgaaaaat | 660 |
| ctggatcgcc tgaaaccggc aattcgcgaa aaaattttag cccacatgga tgacttaaaa | 720 |
| ctgtcttggg atctggccaa agtgcgtacc gatctgccgt tagaagttga ttttgccaaa | 780 |
| cgtcgcgaac cggatcgtga acgcctacga gcctttctgg aacgcttaga atttggctca | 840 |
| ctgttacatg aatttggctt actggaatct ccgaaagcat tagaagaagc cccgtggccg | 900 |
| ccgccggaag cgcctttgt gggctttgtg ctgagtagga agaaccgat gtgggcagac | 960 |
| ttgctggccc tggccgcagc acgcggcggt cgcgttcatc gtgccccgga accgtacaaa | 1020 |
| gccctgcgtg acctgaaaga agcacgcggc ttattagcca aagacctgag tgttctggca | 1080 |
| ttaagggaag gcttaggcct gccgccgggc gatgatccga tgctgctggc ctatctgctt | 1140 |
| gacccgagta ataccacccc ggaaggcgtt gcacgtcgct atggcggcga gtggaccgaa | 1200 |
| gaagcaggcg aacgtgcagc cctgtcagaa cgtctgtttg ccaatctgtg gggtcgctta | 1260 |
| gaaggcgaag aacgcttact gtggttatat cgtgaagtgg aacgtccgct gagcgcagtg | 1320 |
| ctggcacaca tggaagccac cggtgtgcgc ttagatgttg catatctgcg tgccctgtct | 1380 |
| ctggaagttg cagaagaaat tgcacgctta gaagccgaag ttttcgctt agcaggtcat | 1440 |
| ccgtttaact aaatagtcg cgatcagctg gaaaggttc tgtttgatga atctggcctg | 1500 |
| ccggcaattg gcaagaccga aaaaaccggt aaacgctcta cctcagccgc agttctggaa | 1560 |
| gccctgcgcg aagcccatcc gattgttgaa aaattttac agtatcgtga actgaccaaa | 1620 |
| ctgaaatcta cctatattga tccgttaccg gatctaattc atccgcgtac cggtcgctta | 1680 |
| catacccgtt taatcagac cgccaccgcc accggtcgct tatcaagtag cgatccgaac | 1740 |
| ttgcagaata ttccggtgcg taccccgtta ggtcagcgca ttcgtcgtgc ctttattgca | 1800 |
| gaagaaggtt ggttattagt tgcattagat tatagtcaga ttgaactgcg tgtgttagcc | 1860 |
| catctgagcg gcgacgaaaa tctgattcgt gtgtttcagg aaggtcgcga tattcatacc | 1920 |
| gaaaccgcct cttggatgtt tggtgttccg cgcgaagcag ttgatccgtt aatgcgccgt | 1980 |
| gcagccaaaa ccattaattt tggtgtgctg tatggtatga gcgcacatcg cctgtcacag | 2040 |
| gaactggcaa ttccgtatga agaagcacag gcctttattg aacgctattt tcagtctttt | 2100 |

```
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtgaagccg ccgaacgcat ggcctttaat atgccggttc agggaacggc agctgacctt   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca agaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                   2535
```

<210> SEQ ID NO 50
<211> LENGTH: 844
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 50

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
```

-continued

|     | 275 |     |     |     | 280 |     |     |     | 285 |     |     |
|-----|-----|-----|-----|-----|-----|-----|-----|-----|-----|-----|-----|

Glu Ser Pro Lys Ala Leu Glu Glu Ala Pro Trp Pro Pro Glu Gly
       290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Ser Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

```
Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
            725                 730                 735

Val Lys Ser Val Arg Glu Ala Ala Glu Arg Met Ala Phe Asn Met Pro
        740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
        835                 840

<210> SEQ ID NO 51
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atgcgcggta tgctgccgtt atttgaaccg aaaggtcgtg tgctgctggt tgatggtcat       60
cacttagcat atcgtacctt tcatgccctg aaaggcctga ccacctctcg cggcgaaccg      120
gttcaggcag tgtatggttt tgccaaatca ctgctgaaag cattaaaaga agatggcgat      180
gcagtgattg ttgtgtttga tgccaaagcc ccgagctttc gtcatgaagc ctatggcggc      240
tacaaagcag tcgcgcccc gaccccggaa gattttccgc gtcagctggc cttaattaaa      300
gaattagttg acttgctggg cttagcacgt ctggaagttc cgggctatga agcagatgat      360
gttttagcct cactggccaa aaaagccgaa aagaaggct atgaagttcg cattctgacc      420
gcagataagg atctgtatca gctgctgagc gatcgtattc atgtgttaca tccggaaggc      480
tatctgatta ccccggcatg gttatgggaa aaatatggtt acgtccggaa tcagtgggca      540
gattatcgtg cactgaccgg tgacgaatca gataatctgc cggcgttaa aggtattggt      600 gaaaaaccg cccggaaatt attagaagaa tggggtagtc tggaagcatt actgaaaaat      660
ctggatcgcc tgaaaccggc aattcgcgaa aaaattttag cccacatgga tgacttaaaa      720
ctgtcttggg atctggccaa agtgcgtacc gatctgccgt agaagttga ttttgccaaa      780 cgtcgcgaac cggatcgtga acgcctacga gcctttctgg aacgcttaga atttggctca      840
ctgttacatg aatttggctt actggaatct ccgaaagcat agaagaagc cccgtggccg      900 ccgccggaag cgccctttgt gggctttgtg ctgagtagga agaaccgat gtgggcagac      960 ttgctggccc tggccgcagc acgcggcggt cgcgttcatc gtgccccgga accgtacaaa     1020
gccctgcgtg acctgaaaga agcacgcggc ttattagcca aagacctgag tgttctggca     1080
ttaagggaag gcttaggcct gccgccgggc gatgatccga tgctgctggc ctatctgctt     1140
gacccgagta ataccacccc ggaaggcgtt gcacgtcgct atggcggcga gtggaccgaa     1200
```

```
gaagcaggcg aacgtgcagc cctgtcagaa cgtctgtttg ccaatctgtg gggtcgctta      1260
gaaggcgaag aacgcttact gtggttatat cgtgaagtgg aacgtccgct gagcgcagtg      1320
ctggcacaca tggaagccac cggtgtgcgc ttagatgttg catatctgcg tgccctgtct      1380
ctggaagttg cagaagaaat tgcacgctta gaagccgaag tttttcgctt agcaggtcat      1440
ccgtttaact aaatagtcg cgatcagctg gaaagggttc tgtttgatga attaggcctg       1500
ccggcaattg caagaccga aaaaaccggt aaacgctcta cctcagccgc agttctggaa       1560
gccctgcgca agcccatcc gattgttgaa aaaattttac agtatcgtga actgaccaaa       1620
ctgaaatcta cctatattga tccgttaccg gatctaattc atccgcgtac cggtcgctta      1680
catacccgtt ttaatcagac cgccaccgcc accggtcgct tatcaagtag cgatccgaac      1740
ttgcagaata ttccggtgcg taccccgtta ggtcagcgca ttcgtcgtgc ctttattgca      1800
gaagaaggtt ggttattagt tgcattagat tatagtcaga ttgaactgcg tgtgttagcc      1860
catctgagcg gcgacgaaaa tctgattcgt gtgtttcagg aaggtcgcga tattcatacc      1920
gaaaccgcct cttggatgtt tggtgttccg cgcgaagcag ttgatccgtt aatgcgccgt      1980
gcagccaaaa ccattaattt tggtgtgctg tatggtatga gcgcacatcg cctgtcacag      2040
gaactggcaa ttccgtatga agaagcacag gcctttattg aacgctattt tcagtctttt      2100
ccgaaagttc gcgcatggat tgaaaaaacc ttagaagaag gtcgtcgtcg cggctatgtg      2160
gaaaccctgt ttggtcgtcg tcgctatgtt ccggatctgg aagcgagagt taaatcagtg      2220
cgtgaagccg ccgaacgcat ggcctttaat atgccggttc agggaacggc agctgacctt      2280
atgaaactgg caatggttaa actgtttccg cgcctggaaa aaatgggtgc acgaatgctg      2340
ttacaggttc atgatgaatt agttctggaa gccccgaaag aacgcgccga agcagttgca      2400
cgtctggcca aagaagtgat ggaaggtgtg tatccgttag cagttccgtt agaagtggaa      2460
gtgggtattg gtgaagattg gctgagcgcc aaagaaggtt ctggcagttc aggtcatcac      2520
caccatcatc actaa                                                       2535
```

<210> SEQ ID NO 52
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys

```
            115                 120                 125
Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Lys Ala His Pro Ile
        515                 520                 525

Val Glu Lys Ile Leu Gln Tyr Arg Glu Leu Thr Lys Leu Lys Ser Thr
    530                 535                 540
```

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
        835                 840

<210> SEQ ID NO 53
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcagtgattg ttgtgtttga tgccaaagcc ccgagctttc gtcatgaagc ctatggcggc     240
tacaaagcag gtcgcgcccc gaccccggaa gattttccgc gtcagctggc cttaattaaa     300

```
gaattagttg acttgctggg cttagcacgt ctggaagttc cgggctatga agcagatgat      360
gttttagcct cactgccaaa aaaagccgaa aagaaggct atgaagttcg cattctgacc       420
gcagataagg atctgtatca gctgctgagc gatcgtattc atgtgttaca tccggaaggc     480
tatctgatta ccccggcatg gttatgggaa aaatatggtt tacgtccgga tcagtgggca     540
gattatcgtg cactgaccgg tgacgaatca gataatctgc cgggcgttaa aggtattggt     600
gaaaaaccg cccggaaatt attagaagaa tggggtagtc tggaagcatt actgaaaaat      660
ctggatcgcc tgaaaccggc aattcgcgaa aaaattttag cccacatgga tgacttaaaa    720
ctgtcttggg atctgccaa agtgcgtacc gatctgccgt tagaagttga ttttgccaaa     780
cgtcgcgaac cggatcgtga acgcctacga gcctttctgg aacgcttaga atttggctca     840
ctgttacatg aatttggctt actgaatct ccgaaagcat tagaagaagc cccgtggccg     900
ccgccggaag gcgcctttgt gggctttgtg ctgagtagga agaaccgat gtgggcagac     960
ttgctggccc tggccgcagc acgcggcggt cgcgttcatc gtgccccgga accgtacaaa    1020
gccctgcgtg acctgaaaga agcacgcggc ttattagcca aagacctgag tgttctggca   1080
ttaaggaag gcttaggcct gccgccgggc gatgatccga tgctgctggc ctatctgctt    1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta   1260
gaaggcgaag aacgcttact gtggttatat cgtgaagtgg aacgtccgct gagcgcagtg 1320
ctggcacaca tggaagccac cggtgtgcgc ttagatgttg catatctgcg tgccctgtct   1380
ctggaagttg cagaagaaat tgcacgctta gaagccgaag tttttcgctt agcaggtcat  1440
ccgtttaact aaatagtcg cgatcagctg gaaagggttc tgtttgatga attaggcctg   1500
ccggcaattg gcaagaccga aaaaccggt aaacgctcta cctcagccgc agttctggaa   1560
gccctgcgcg aagcccatcc gattgttgaa aaaattttac agtatcgtga actgaccaaa 1620
ctgaaatcta cctatattga tccgttaccg cgtctaattc atccgcgtac cggtcgctta  1680
catacccgtt ttaatcagac cgccaccgcc accggtcgct tatcaagtag cgatccgaac  1740
ttgcagaata ttccggtgcg tacccccgtta ggtcagcgca ttcgtcgtgc ctttattgca 1800
gaagaaggtt ggttattagt tgcattagat tatagtcaga ttgaactgcg tgtgttagcc 1860
catctgagcg cgacgaaaa tctgattcgt gtgtttcagg aaggtcgcga tattcatacc   1920
gaaaccgcct cttggatgtt tggtgttccg cgcgaagcag ttgatccgtt aatgcgccgt 1980
gcagccaaaa ccattaattt tggtgtgctg tatggtatga gcgcacatcg cctgtcacag  2040
gaactggcaa ttccgtatga agaagcacag gcctttattg aacgctattt tcagtctttt  2100
ccgaaagttc gcgcatggat tgaaaaaacc ttagaagaag tcgtcgtcg cggctatgtg  2160
gaaaccctgt ttggtcgtcg tcgctatgtt ccggatctgg aagcgagagt taaatcagtg 2220
cgtgaagccg ccgaacgcat ggcctttaat atgccggttc agggaacggc agctgacctt  2280
atgaaactgg caatggttaa actgtttccg cgcctggaag aaatgggtgc acgaatgctg 2340
ttacaggttc atgatgaatt agttctggaa gccccgaaag aacgcgccga agcagttgca 2400
cgtctggcca aagaagtgat ggaagtgtgt atccgttag cagttccgtt agaagtggaa  2460
gtgggtattg gtgaagattg gctgagcgcc aaagaaggtt ctggcagttc aggtcatcac  2520
caccatcatc actaa                                                      2535

<210> SEQ ID NO 54
<211> LENGTH: 844
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54
```

| | | | | | | | | | | | | | | |
|---|---|---|---|---|---|---|---|---|---|---|---|---|---|---|
| Met | Arg | Gly | Met | Leu | Pro | Leu | Phe | Glu | Pro | Lys | Gly | Arg | Val | Leu | Leu |
| 1 | | | | 5 | | | | | 10 | | | | | 15 | |

| Val | Asp | Gly | His | His | Leu | Ala | Tyr | Arg | Thr | Phe | His | Ala | Leu | Lys | Gly |
|---|---|---|---|---|---|---|---|---|---|---|---|---|---|---|---|
| | | | 20 | | | | | 25 | | | | | 30 | | |

| Leu | Thr | Thr | Ser | Arg | Gly | Glu | Pro | Val | Gln | Ala | Val | Tyr | Gly | Phe | Ala |
|---|---|---|---|---|---|---|---|---|---|---|---|---|---|---|---|
| | | | 35 | | | | | 40 | | | | | 45 | | |

| Lys | Ser | Leu | Leu | Lys | Ala | Leu | Lys | Glu | Asp | Gly | Asp | Ala | Val | Ile | Val |
|---|---|---|---|---|---|---|---|---|---|---|---|---|---|---|---|
| | 50 | | | | | 55 | | | | | 60 | | | | |

| Val | Phe | Asp | Ala | Lys | Ala | Pro | Ser | Phe | Arg | His | Glu | Ala | Tyr | Gly | Gly |
|---|---|---|---|---|---|---|---|---|---|---|---|---|---|---|---|
| 65 | | | | | 70 | | | | | 75 | | | | | 80 |

| Tyr | Lys | Ala | Gly | Arg | Ala | Pro | Thr | Pro | Glu | Asp | Phe | Pro | Arg | Gln | Leu |
|---|---|---|---|---|---|---|---|---|---|---|---|---|---|---|---|
| | | | | 85 | | | | | 90 | | | | | 95 | |

| Ala | Leu | Ile | Lys | Glu | Leu | Val | Asp | Leu | Leu | Gly | Leu | Ala | Arg | Leu | Glu |
|---|---|---|---|---|---|---|---|---|---|---|---|---|---|---|---|
| | | | 100 | | | | | 105 | | | | | 110 | | |

| Val | Pro | Gly | Tyr | Glu | Ala | Asp | Asp | Val | Leu | Ala | Ser | Leu | Ala | Lys | Lys |
|---|---|---|---|---|---|---|---|---|---|---|---|---|---|---|---|
| | | | 115 | | | | | 120 | | | | | 125 | | |

| Ala | Glu | Lys | Glu | Gly | Tyr | Glu | Val | Arg | Ile | Leu | Thr | Ala | Asp | Lys | Asp |
|---|---|---|---|---|---|---|---|---|---|---|---|---|---|---|---|
| | 130 | | | | | 135 | | | | | 140 | | | | |

| Leu | Tyr | Gln | Leu | Leu | Ser | Asp | Arg | Ile | His | Val | Leu | His | Pro | Glu | Gly |
|---|---|---|---|---|---|---|---|---|---|---|---|---|---|---|---|
| 145 | | | | | 150 | | | | | 155 | | | | | 160 |

| Tyr | Leu | Ile | Thr | Pro | Ala | Trp | Leu | Trp | Glu | Lys | Tyr | Gly | Leu | Arg | Pro |
|---|---|---|---|---|---|---|---|---|---|---|---|---|---|---|---|
| | | | | 165 | | | | | 170 | | | | | 175 | |

| Asp | Gln | Trp | Ala | Asp | Tyr | Arg | Ala | Leu | Thr | Gly | Asp | Glu | Ser | Asp | Asn |
|---|---|---|---|---|---|---|---|---|---|---|---|---|---|---|---|
| | | | 180 | | | | | 185 | | | | | 190 | | |

| Leu | Pro | Gly | Val | Lys | Gly | Ile | Gly | Glu | Lys | Thr | Ala | Arg | Lys | Leu | Leu |
|---|---|---|---|---|---|---|---|---|---|---|---|---|---|---|---|
| | | | 195 | | | | | 200 | | | | | 205 | | |

| Glu | Glu | Trp | Gly | Ser | Leu | Glu | Ala | Leu | Leu | Lys | Asn | Leu | Asp | Arg | Leu |
|---|---|---|---|---|---|---|---|---|---|---|---|---|---|---|---|
| | 210 | | | | | 215 | | | | | 220 | | | | |

| Lys | Pro | Ala | Ile | Arg | Glu | Lys | Ile | Leu | Ala | His | Met | Asp | Asp | Leu | Lys |
|---|---|---|---|---|---|---|---|---|---|---|---|---|---|---|---|
| 225 | | | | | 230 | | | | | 235 | | | | | 240 |

| Leu | Ser | Trp | Asp | Leu | Ala | Lys | Val | Arg | Thr | Asp | Leu | Pro | Leu | Glu | Val |
|---|---|---|---|---|---|---|---|---|---|---|---|---|---|---|---|
| | | | | 245 | | | | | 250 | | | | | 255 | |

| Asp | Phe | Ala | Lys | Arg | Arg | Glu | Pro | Asp | Arg | Glu | Arg | Leu | Arg | Ala | Phe |
|---|---|---|---|---|---|---|---|---|---|---|---|---|---|---|---|
| | | | 260 | | | | | 265 | | | | | 270 | | |

| Leu | Glu | Arg | Leu | Glu | Phe | Gly | Ser | Leu | Leu | His | Glu | Phe | Gly | Leu | Leu |
|---|---|---|---|---|---|---|---|---|---|---|---|---|---|---|---|
| | | 275 | | | | | 280 | | | | | 285 | | | |

| Glu | Ser | Pro | Lys | Ala | Leu | Glu | Glu | Ala | Pro | Trp | Pro | Pro | Pro | Glu | Gly |
|---|---|---|---|---|---|---|---|---|---|---|---|---|---|---|---|
| | 290 | | | | | 295 | | | | | 300 | | | | |

| Ala | Phe | Val | Gly | Phe | Val | Leu | Ser | Arg | Lys | Glu | Pro | Met | Trp | Ala | Asp |
|---|---|---|---|---|---|---|---|---|---|---|---|---|---|---|---|
| 305 | | | | | 310 | | | | | 315 | | | | | 320 |

| Leu | Leu | Ala | Leu | Ala | Ala | Ala | Arg | Gly | Gly | Arg | Val | His | Arg | Ala | Pro |
|---|---|---|---|---|---|---|---|---|---|---|---|---|---|---|---|
| | | | | 325 | | | | | 330 | | | | | 335 | |

| Glu | Pro | Tyr | Lys | Ala | Leu | Arg | Asp | Leu | Lys | Glu | Ala | Arg | Gly | Leu | Leu |
|---|---|---|---|---|---|---|---|---|---|---|---|---|---|---|---|
| | | | 340 | | | | | 345 | | | | | 350 | | |

| Ala | Lys | Asp | Leu | Ser | Val | Leu | Ala | Leu | Arg | Glu | Gly | Leu | Gly | Leu | Pro |
|---|---|---|---|---|---|---|---|---|---|---|---|---|---|---|---|
| | | 355 | | | | | 360 | | | | | 365 | | | |

| Pro | Gly | Asp | Asp | Pro | Met | Leu | Leu | Ala | Tyr | Leu | Leu | Asp | Pro | Ser | Asn |
|---|---|---|---|---|---|---|---|---|---|---|---|---|---|---|---|
| | 370 | | | | | 375 | | | | | 380 | | | | |

```
Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
        420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Arg Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800
```

```
Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

Gly Ser Gly Ser Ser Gly His His His His His His
        835                 840

<210> SEQ ID NO 55
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga gatggcgat     180 gcagtgattg ttgtgtttga tgccaaagcc ccgagctttc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc gggctatga agcagatgat     360 gttttagcct cactggccaa aaaagccgaa aagaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt acgtccgga tcagtgggca     540 gattatcgtg cactgaccgg tgacgaatca gataatctgc cggcgttaa aggtattggt     600 gaaaaaaccg cccggaaatt attagaagaa tggggtagtc tggaagcatt actgaaaaat     660
ctggatcgcc tgaaaccggc aattcgcgaa aaaattttag cccacatgga tgacttaaaa     720
ctgtcttggg atctggccaa agtgcgtacc gatctgccgt tagaagttga ttttgccaaa     780
cgtcgcgaac cggatcgtga acgcctacga gcctttctgg aacgcttaga atttggctca     840
ctgttacatg aatttggctt actggaatct ccgaaagcat agaagaagc cccgtggccg     900 ccgccggaag gcgcctttgt gggctttgtg ctgagtagga aagaaccgat gtgggcagac     960
ttgctggccc tggccgcagc acgcggcggt cgcgttcatc gtgccccgga accgtacaaa    1020
gccctgcgtg aacctgaaaga agcacgcggc ttattagcca aagacctgag tgttctggca    1080
ttaagggaag gcttaggcct gccgccgggc gatgatccga tgctgctggc ctatctgctt    1140
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
ctggaagttg cagaagaaat tgcacgctta gaagccgaag ttttttcgctt agcaggtcat    1440 ccgtttaact taaatagtcg cgatcagctg gaaagggttc tgtttgatga attaggcctg    1500
ccggcaattg gcaagaccga aaaaaccggt aaacgctcta cctcagccgc agttctggaa    1560
gccctgcgcg aagcccatcc gattgttgaa aaaattttac agtatcgtga actgaccaaa    1620
ctgaaatcta cctatattga tccgttaccg gatctaattc atccggatac cggtcgctta    1680 cataccccgtt ttaatcagac cgccaccgcc accggtcgct atcaagtag cgatccgaac    1740 ttgcagaata ttccggtgcg taccccgtta ggtcagcgca ttcgtcgtgc ctttattgca    1800
```

-continued

```
gaagaaggtt ggttattagt tgcattagat tatagtcaga ttgaactgcg tgtgttagcc      1860
catctgagcg gcgacgaaaa tctgattcgt gtgtttcagg aaggtcgcga tattcatacc      1920
gaaaccgcct cttggatgtt tggtgttccg cgcgaagcag ttgatccgtt aatgcgccgt      1980
gcagccaaaa ccattaattt tggtgtgctg tatggtatga gcgcacatcg cctgtcacag      2040
gaactggcaa ttccgtatga agaagcacag gcctttattg aacgctattt tcagtctttt      2100
ccgaaagttc gcgcatggat tgaaaaaacc ttagaagaag gtcgtcgtcg cggctatgtg      2160
gaaaccctgt ttggtcgtcg tcgctatgtt ccggatctgg aagcgagagt taaatcagtg      2220
cgtgaagccg ccgaacgcat ggcctttaat atgccggttc agggaacggc agctgacctt      2280
atgaaactgg caatggttaa actgtttccg cgcctggaag aaatgggtgc acgaatgctg      2340
ttacaggttc atgatgaatt agttctggaa gccccgaaag aacgcgccga agcagttgca      2400
cgtctggcca agaagtgat ggaaggtgtg tatccgttag cagttccgtt agaagtggaa       2460
gtgggtattg gtgaagattg gctgagcgcc aaagaaggtt ctggcagttc aggtcatcac      2520
caccatcatc actaa                                                       2535
```

<210> SEQ ID NO 56
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220
```

-continued

```
Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Asp Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640
```

| | | | | | | | | | | | |
|---|---|---|---|---|---|---|---|---|---|---|---|
|Glu|Thr|Ala|Ser|Trp|Met|Phe|Gly|Val|Pro|Arg|Glu|Ala|Val|Asp|Pro|
| | | | |645| | | |650| | | |655| | | |

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
            835                 840

<210> SEQ ID NO 57
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga gatggcgat      180 gcagtgattg ttgtgtttga tgccaaagcc ccgagctttc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc cgggctatga agcagatgat     360
gttttagcct cactggccaa aaaagccgaa aagaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt acgtccgga tcagtgggca     540 gattatcgtg cactgaccgg tgacgaatca gataatctgc cggcgttaa aggtattggt     600 gaaaaaaccg cccggaaatt attagaagaa tgggtagtc tggaagcatt actgaaaaat     660
ctggatcgcc tgaaaccggc aattcgcgaa aaaattttag cccacatgga tgacttaaaa     720
ctgtcttggg atctggccaa agtgcgtacc gatctgccgt tagaagttga ttttgccaaa     780
cgtcgcgaac cggatcgtga acgcctacga gcctttctgg aacgcttaga atttggctca     840
ctgttacatg aatttggctt actggaatct ccgaaagcat agaagaagc cccgtggccg     900
```

```
ccgccggaag gcgcctttgt gggctttgtg ctgagtagga aagaaccgat gtgggcagac   960
ttgctggccc tggccgcagc acgcggcggt cgcgttcatc gtgccccgga accgtacaaa  1020
gccctgcgtg acctgaaaga agcacgcggc ttattagcca aagacctgag tgttctggca  1080
ttaagggaag gcttaggcct gccgccgggc gatgatccga tgctgctggc ctatctgctt  1140
gacccgagta ataccacccc ggaaggcgtt gcacgtcgct atggcggcga gtggaccgaa  1200
gaagcaggcg aacgtgcagc cctgtcagaa cgtctgtttg ccaatctgtg gggtcgctta  1260
gaaggcgaag aacgcttact gtggttatat cgtgaagtgg aacgtccgct gagcgcagtg  1320
ctggcacaca tggaagccac cggtgtgcgc ttagatgttg catatctgcg tgccctgtct  1380
ctggaagttg cagaagaaat tgcacgctta gaagccgaag ttttttcgctt agcaggtcat  1440
ccgtttaact aaatagtcg cgatcagctg aaagggttc tgtttgatga attaggcctg  1500
ccggcaattg gcaagaccga aaaaaccggt aaacgctcta cctcagccgc agttctggaa  1560
gccctgcgcg aagcccatcc gattgttgaa aaaattttac agtatcgtga actgaccaaa  1620
ctgaaatcta cctatattga tccgttaccg gatctaattc atccgcgtac cggtcgctta  1680
cataccccgtt ttaatcagac cgccaccgcc accggtcgct tatcaagtag cgatccgaac  1740
ttgcagaata ttccggtgcg taccccgtta ggtcagcgca ttcgtcgtgc ctttattgca  1800
gaagaaggtt ggttattagt tgcattagat tatagtcaga ttgaactgcg tgtgttagcc  1860
catctgagcg gcgacgaaaa tctgattcgt gtgtttcagg aaggtcgcga tattcatacc  1920
gaaaccgcct cttggatgtt tggtgttccg cgcgaagcag ttgatccgtt aatgcgccgt  1980
gcagccaaaa ccattaattt tggtgtgctg tatggtatga gcgcacatcg cctgatacag  2040
gaactggcaa ttccgtatga agaagcacag gcctttattg aacgctatttt tcagtctttt  2100
ccgaaagttc gcgcatggat tgaaaaaacc ttagaagaag gtcgtcgtcg cggctatgtg  2160
gaaaccctgt ttggtcgtcg tcgctatgtt ccggatctgg aagcgagagt taaatcagtg  2220
cgtgaagccg ccgaacgcat ggcctttaat atgccggttc agggaacggc agctgacctt  2280
atgaaactgg caatggttaa actgtttccg cgcctggaag aaatgggtgc acgaatgctg  2340
ttacaggttc atgatgaatt agttctggaa gccccgaaag aacgcgccga agcagttgca  2400
cgtctggcca aagaagtgat ggaaggtgtg tatccgttag cagttccgtt agaagtggaa  2460
gtgggtattg gtgaagattg gctgagcgcc aaagaaggtt ctggcagttc aggtcatcac  2520
caccatcatc actaa                                                   2535

<210> SEQ ID NO 58
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60
```

```
Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480
```

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
        500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ile Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
        835                 840

<210> SEQ ID NO 59
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

-continued

```
atgcgcggta tgctgccgtt atttgaaccg aaaggtcgtg tgctgctggt tgatggtcat      60
cacttagcat atcgtacctt tcatgccctg aaaggcctga ccacctctcg cggcgaaccg     120
gttcaggcag tgtatggttt tgccaaatca ctgctgaaag cattaaaaga agatggcgat     180
gcagtgattg ttgtgtttga tgccaaagcc ccgagctttc gtcatgaagc ctatggcggc     240
tacaaagcag gtcgcgcccc gaccccggaa gattttccgc gtcagctggc cttaattaaa     300
gaattagttg acttgctggg cttagcacgt ctggaagttc cgggctatga agcagatgat     360
gttttagcct cactggccaa aaaagccgaa aagaaggct atgaagttcg cattctgacc     420
gcagataagg atctgtatca gctgctgagc gatcgtattc atgtgttaca tccggaaggc     480
tatctgatta ccccggcatg gttatgggaa aaatatggtt tacgtccgga tcagtgggca     540
gattatcgtg cactgaccgg tgacgaatca gataatctgc cggcgttaa aggtattggt     600
gaaaaaccg cccggaaatt attagaagaa tggggtagtc tggaagcatt actgaaaaat     660
ctggatcgcc tgaaaccggc aattcgcgaa aaaattttag cccacatgga tgacttaaaa     720
ctgtcttggg atctggccaa agtgcgtacc gatctgccgt tagaagttga ttttgccaaa     780
cgtcgcgaac cggatcgtga acgcctacga gcctttctgg aacgcttaga atttggctca     840
ctgttacatg aatttggctt actggaatct ccgaaagcat tagaagaagc cccgtggccg     900
ccgccggaag gcgcctttgt gggctttgtg ctgagtagga aagaaccgat gtgggcagac     960
ttgctggccc tggccgcagc acgcggcggt cgcgttcatc gtgccccgga accgtacaaa    1020
gccctgcgtg acctgaaaga agcacgcggc ttattagcca aagacctgag tgttctggca    1080
ttaagggaag gcttaggcct gccgccgggc gatgatccga tgctgctggc ctatctgctt    1140
gacccgagta ataccacccc ggaaggcgtt gcacgtcgct atggcggcga gtggaccgaa    1200
gaagcaggcg aacgtgcagc cctgtcagaa cgtctgtttg ccaatctgtg gggtcgctta    1260
gaaggcgaag aacgcttact gtggttatat cgtgaagtgg aacgtccgct gagcgcagtg    1320
ctggcacaca tggaagccac cggtgtgcgc ttagatgttg catatctgcg tgccctgtct    1380
ctggaagttg cagaagaaat tgcacgctta gaagccgaag ttttcgctt agcaggtcat    1440
ccgtttaact aaatagtcg cgatcagctg gaaagggttc tgtttgatga attaggcctg    1500
ccggcaattg gcaagaccga aaaaaccggt aaacgctcta cctcagccgc agttctggaa    1560
gccctgcgcg aagcccatcc gattgttgaa aaattttac agtatcgtga actgaccaaa    1620
ctgaaatcta cctatattga tccgttaccg gatctaattc atccgcgtac cggtcgctta    1680
catacccgtt ttaatcagac cgccaccgcc accggtcgct tatcaagtag cgatccgaac    1740
ttgcagaata ttccggtgcg taccccgtta ggtcagcgca ttcgtcgtgc ctttattgca    1800
gaagaaggtt ggttattagt tgcattagat tatagtcaga ttgaactgcg tgtgttagcc    1860
catctgagcg gcgacgaaaa tctgattcgt gtgtttcagg aaggtcgcga tattcatacc    1920
gaaaccgcct cttggatgtt tggtgttccg cgcgaagcag ttgatccgtt aatgcgccgt    1980
gcagccaaaa ccattaattt tggtgtgctg tatggtatga gcgcacatcg cctgtcacag    2040
gaactggcaa ttccgtatga agaagcacag gcctttattg aacgctattt tcagtctttt    2100
ccgaaagttc gcgcatggat tgaaaaaacc ttagaagaag tcgtcgtcg cggctatgtg    2160
gaaaccctgt ttggtcgtcg tcgctatgtt ccggatctgg aagcgagagt taaatcagtg    2220
cgtgaagccg ccgaacgcat ggcctttaat atgccggttc agggaacggc agctgacctt    2280
atgaaactgg caatggttaa actgtttccg cgcctggaag aaatgggtgc acgaatgctg    2340
```

-continued

```
ttacaggttc atgatgaatt agtttctgaa gccccgaaag aacgcgccga agcagttgca      2400
cgtctggcca agaagtgat ggaaggtgtg tatccgttag cagttccgtt agaagtggaa       2460
gtgggtattg gtgaagattg gctgagcgcc aaagaaggtt ctggcagttc aggtcatcac     2520
caccatcatc actaa                                                       2535
```

<210> SEQ ID NO 60
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320
```

```
Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
        340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
```

```
            740                 745                 750
Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Ser Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His His
            835                 840

<210> SEQ ID NO 61
<211> LENGTH: 2535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgcgcggta tgctgccgtt atttgaaccg aaaggtcgtg tgctgctggt tgatggtcat         60
cacttagcat atcgtacctt tcatgccctg aaaggcctga ccacctctcg cggcgaaccg        120
gttcaggcag tgtatggttt tgccaaatca ctgctgaaag cattaaaaga agatggcgat        180
gcagtgattg ttgtgtttga tgccaaagcc ccgagctttc gtcatgaagc ctatggcggc        240
tacaaagcag gtcgcgcccc gaccccggaa gattttccgc gtcagctggc cttaattaaa        300
gaattagttg acttgctggg cttagcacgt ctggaagttc gggctatga agcagatgat        360 gttttagcct cactgccaa aaaagccgaa aagaaggct atgaagttcg cattctgacc         420
gcagataagg atctgtatca gctgctgagc gatcgtattc atgtgttaca tccggaaggc        480
tatctgatta ccccggcatg gttatgggaa aaatatggtt acgtccgga tcagtgggca        540 gattatcgtg cactgaccgg tgacaaatca gataatctgc cgggcgttaa aggtattggt        600
gaaaaaaccg cccggaaatt attagaagaa tggggtagtc tggaagcatt actgaaaaat        660
ctggatcgcc tgaaaccggc aattcgcgaa aaattttag cccacatgga tgacttaaaa         720
ctgtcttggg atctggccaa agtgcgtacc gatctgccgt tagaagttga ttttgccaaa        780
cgtcgcgaac cggatcgtga cgcctacga gcctttctgg aacgcttaga atttggctca         840
ctgttacatg aatttggctt actggaatct ccgaaagcat agaagaagc ccgtggccg          900 ccgccggaag cgcctttgt gggctttgtg ctgagtagga agaaccgat gtgggcagac          960 ttgctggccc tggccgcagc acgcggcggt cgcgttcatc gtgccccgga accgtacaaa       1020
gccctgcgtg acctgaaaga agcacgcggc ttattagcca agacctgag tgttctggca       1080 ttaagggaag gcttaggcct gccgccgggc gatgatccga tgctgctggc ctatctgctt       1140
gacccgagta ataccacccc ggaaggcgtt gcacgtcgct atggcggcga gtggaccgaa       1200
gaagcaggcg aacgtgcagc cctgtcagaa cgtctgtttg ccaatctgtg gggtcgctta       1260
gaaggcgaag aacgcttact gtggttatat cgtgaagtgg aacgtccgct gagcgcagtg       1320
ctggcacaca tggaagccac cggtgtgcgc ttagatgttg catatctgcg tgccctgtct       1380
ctggaagttg cagaagaaat tgcacgctta gaagccgaag ttttttcgctt agcaggtcat     1440
```

```
ccgtttaact taaatagtcg cgatcagctg gaaagggttc tgtttgatga attaggcctg   1500
ccggcaattg gcaagaccaa aaaaaccggt aaacgctcta cctcagccgc agttctggaa   1560
gccctgcgcg aagcccatcc gattgttgaa aaaattttac agtatcgtga actgaccaaa   1620
ctgaaatcta cctatattga tccgttaccg gatctaattc atccgcgtac cggtcgctta   1680
catacccgtt ttaatcagac cgccaccgcc accggtcgct tatcaagtag cgatccgaac   1740
ttgcagaata ttccggtgcg taccccgtta ggtcagcgca ttcgtcgtgc ctttattgca   1800
gaagaaggtt ggttattagt tgcattagat tatagtcaga ttgaactgcg tgtgttagcc   1860
catctgagcg gcgacgaaaa tctgattcgt gtgtttcagg aaggtcgcga tattcatacc   1920
gaaaccgcct cttggatgtt tggtgttccg cgcgaagcag ttgatccgtt aatgcgccgt   1980
gcagccaaaa ccattaattt tggtgtgctg tatggtatga gcgcacatcg cctgtcacag   2040
gaactggcaa ttccgtatga agaagcacag gcctttattg aacgctattt tcagtctttt   2100
ccgaaagttc gcgcatggat tgaaaaaacc ttagaagaag gtcgtcgtcg cggctatgtg   2160
gaaaccctgt ttggtcgtcg tcgctatgtt ccggatctgg aagcgagagt taaatcagtg   2220
cgtaaagccg ccgaacgcat ggcctttaat atgccggttc agggaacggc agctgaccct   2280
atgaaactgg caatggttaa actgtttccg cgcctggaag aaatgggtgc acgaatgctg   2340
ttacaggttc atgatgaatt agttctggaa gccccgaaag aacgcgccga agcagttgca   2400
cgtctggcca aagaagtgat ggaaggtgtg tatccgttag cagttccgtt agaagtggaa   2460
gtgggtattg gtgaagattg gctgagcgcc aaagaaggtt ctggcagttc aggtcatcac   2520
caccatcatc actaa                                                   2535
```

<210> SEQ ID NO 62
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
              165                 170                 175

Asp Gln Trp Ala Asp Tyr Arg Ala Leu Thr Gly Asp Lys Ser Asp Asn
        180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
        260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
        340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Lys Thr Gly Lys Arg
        500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln

```
                580                 585                 590
Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Lys Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

Gly Ser Gly Ser Ser Gly His His His His His
        835                 840

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttacaaacat tggccgcaaa                                                 20

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcgcgacatt ccgaagaa                                                   18

<210> SEQ ID NO 65
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
acaatttgcc cccagcgctt cag                                             23
```

TAQ DNA POLYMERASE MUTANTS FOR PROBE QPCR

BACKGROUND

Taq DNA polymerase is commonly used in molecular biology for extending nucleic acid amplicons in polymerase chain reactions (PCR). In PCR, designated segments of DNA (amplicons) are amplified by the repeated cycling of three steps: denaturation, annealing, and elongation/extension of the amplicon. With qualitative, real-time PCR (qPCR), fluorescent signal generated through dyes or probes allows for data collection during PCR cycling so that target amplification can be measured and recorded. Probe-based chemistries utilize fluorescently labeled, target-specific probes which only release a reporter dye when bound to target sequence, allowing for real-time detection of target amplification as fluorescent signal intensity increases.

Two inherent enzyme activities of Taq DNA polymerase, DNA polymerization and 5' to 3' exonuclease activity, are the basis of probe-based qPCR. As qPCR probe amplicons are generally very short, wild type Taq polymerization activity is normally enough to extend those probe amplicons even at very short extension intervals of one second. However, the rate-limiting factor in probe-based qPCR is the 5' to 3' exonuclease activity responsible for releasing the reporter signal. Wild type Taq DNA polymerase is unable to cleave the probe from its attached fluorophore within one second, irrespective of polymerization during that period, thus inhibiting detection. Thus what is needed are Taq DNA polymerase mutants having increased efficiency of Taq polymerase 5' to 3' exonuclease activity and which allow for detection of rapid amplification during qPCR.

SUMMARY

Taq DNA polymerase mutants of the invention exhibit enhanced efficiency in qPCR compared to the wild type Taq DNA polymerase. Taq DNA polymerase mutants of the invention were engineered, characterized, and selected via probe-based qualitative, real-time PCR (qPCR) with a cycling protocol using a rapid extension time (one second per cycle). A number of suitable mutants were found, including: V62S, V64S, A70F, F73A, A77F, P253G, E255K, D257R, A259F, A271F, L288S, E289K, S357I, L361S, L376S, P382G, T385I, G418P, R419D, E421K, L461S, A472F, E497K, L498S, E524K, D551R, R556D, S679I, L789S, E189K/E507K/E742K (See Sequence Listing Guide below, where the DNA and protein sequence for each mutant is indicated by the associated listing number).

Compared to traditional, longer protocols for wild-type enzyme, the engineered mutants' ability to detect rapid extension significantly decreases the total run time required for a qPCR run, significantly boosting the efficiency of detecting target nucleic acids with qPCR or real time qPCR. This would be a significant economic advantage for use of the mutants.

Taq DNA polymerase mutants of the invention can be used in conventional qPCR assays, including for gene expression analysis and other DNA quantification.

SEQUENCE LISTING GUIDE

Figure 1A:
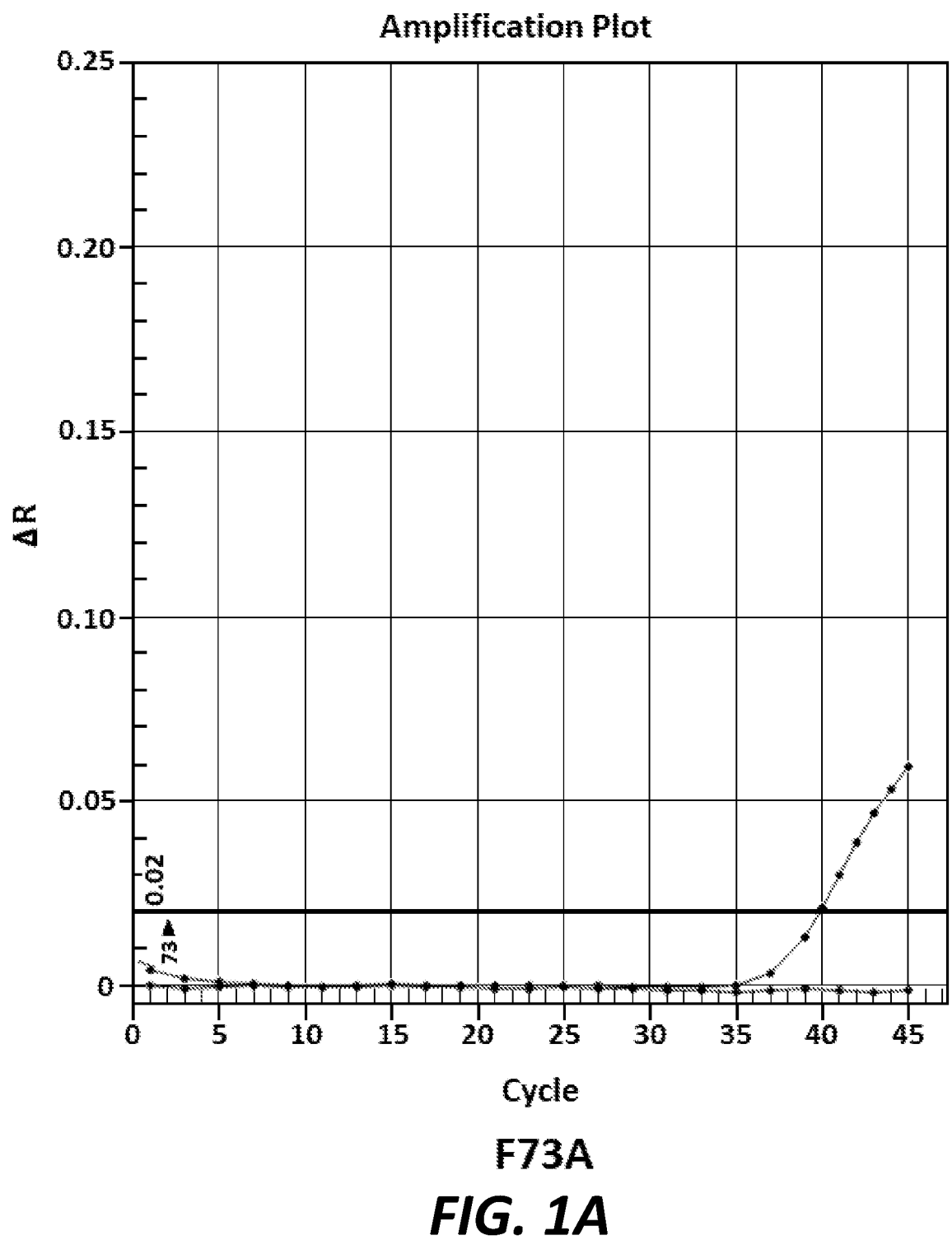
FIGS. 1A to 1II are each amplification plots showing probe qPCR signal comparisons of Taq DNA wild type (FIGS. 1E, 1M, 1U, 1CC, 1GG, each labeled "WT") and a number of the Taq DNA polymerase mutants, as identified below the X axis in each figure. The X axis in each figure is the cycle number and the Y axis is the change in fluorescent signal detected (ΔR), representing the indicated mutant's the change in fluorescence throughout the cycling protocol, with dots indicating specific measured signal value per cycle. All detection threshold lines are fixed at 0.02. The qPCR protocol for all mutants was run in duplicate, as indicated in figures where two distinct sets of dots and lines can be seen.

SEQ ID NO: 1 is the DNA sequence of Wild Type Taq DNA polymerase with a C terminal Histag.
SEQ ID NO: 2 is the protein sequence of Wild Type Taq DNA polymerase with a C terminal Histag.
SEQ ID NO: 3 is the DNA sequence of mutant (V62S) Taq DNA polymerase with a C terminal Histag.
SEQ ID NO: 4 is the protein sequence of mutant (V62S) Taq DNA polymerase with a C terminal Histag.
SEQ ID NO: 5 is the DNA sequence of mutant (V64S) Taq DNA polymerase with a C terminal Histag.
SEQ ID NO: 6 is the protein sequence of mutant (V64S) Taq DNA polymerase with a C terminal Histag.
SEQ ID NO: 7 is the DNA sequence of mutant (A70F) Taq DNA polymerase with a C terminal Histag.
SEQ ID NO: 8 is the protein sequence of mutant (A70F) Taq DNA polymerase with a C terminal Histag.
SEQ ID NO: 9 is the DNA sequence of mutant (F73A) Taq DNA polymerase with a C terminal Histag.
SEQ ID NO: 10 is the protein sequence of mutant (F73A) Taq DNA polymerase with a C terminal Histag.
SEQ ID NO: 11 is the DNA sequence of mutant (A77F) Taq DNA polymerase with a C terminal Histag.
SEQ ID NO: 12 is the protein sequence of mutant (A77F) Taq DNA polymerase with a C terminal Histag.
SEQ ID NO: 13 is the DNA sequence of mutant (P253G) Taq DNA polymerase with a C terminal Histag.
SEQ ID NO: 14 is the protein sequence of mutant (P253G) Taq DNA polymerase with a C terminal Histag.
SEQ ID NO: 15 is the DNA sequence of mutant (E255K) Taq DNA polymerase with a C terminal Histag.
SEQ ID NO: 16 is the protein sequence of mutant (E255K) Taq DNA polymerase with a C terminal Histag.
SEQ ID NO: 17 is the DNA sequence of mutant (D257R) Taq DNA polymerase with a C terminal Histag.
SEQ ID NO: 18 is the protein sequence of mutant (D257R) Taq DNA polymerase with a C terminal Histag.
SEQ ID NO: 19 is the DNA sequence of mutant (A259F) Taq DNA polymerase with a C terminal Histag.
SEQ ID NO: 20 is the protein sequence of mutant (A259F) Taq DNA polymerase with a C terminal Histag.
SEQ ID NO: 21 is the DNA sequence of mutant (A271F) Taq DNA polymerase with a C terminal Histag.
SEQ ID NO: 22 is the protein sequence of mutant (A271F) Taq DNA polymerase with a C terminal Histag.
SEQ ID NO: 23 is the DNA sequence of mutant (L288S) Taq DNA polymerase with a C terminal Histag.
SEQ ID NO: 24 is the protein sequence of mutant (L288S) Taq DNA polymerase with a C terminal Histag.
SEQ ID NO: 25 is the DNA sequence of mutant (E289K) Taq DNA polymerase with a C terminal Histag.
SEQ ID NO: 26 is the protein sequence of mutant (E289K) Taq DNA polymerase with a C terminal Histag.
SEQ ID NO: 27 is the DNA sequence of mutant (S357I) Taq DNA polymerase with a C terminal Histag.
SEQ ID NO: 28 is the protein sequence of mutant (S357I) Taq DNA polymerase with a C terminal Histag.

SEQ ID NO: 29 is the DNA sequence of mutant (L361S) Taq DNA polymerase with a C terminal Histag.
SEQ ID NO: 30 is the protein sequence of mutant (L361S) Taq DNA polymerase with a C terminal Histag.
SEQ ID NO: 31 is the DNA sequence of mutant (L376S) Taq DNA polymerase with a C terminal Histag.
SEQ ID NO: 32 is the protein sequence of mutant (L376S) Taq DNA polymerase with a C terminal Histag.
SEQ ID NO: 33 is the DNA sequence of mutant (P382G) Taq DNA polymerase with a C terminal Histag.
SEQ ID NO: 34 is the protein sequence of mutant (P382G) Taq DNA polymerase with a C terminal Histag.
SEQ ID NO: 35 is the DNA sequence of mutant (T385I) Taq DNA polymerase with a C terminal Histag.
SEQ ID NO: 36 is the protein sequence of mutant (T385I) Taq DNA polymerase with a C terminal Histag.
SEQ ID NO: 37 is the DNA sequence of mutant (G418P) Taq DNA polymerase with a C terminal Histag.
SEQ ID NO: 38 is the protein sequence of mutant (G418P) Taq DNA polymerase with a C terminal Histag.
SEQ ID NO: 39 is the DNA sequence of mutant (R419D) Taq DNA polymerase with a C terminal Histag.
SEQ ID NO: 40 is the protein sequence of mutant (R419D) Taq DNA polymerase with a C terminal Histag.
SEQ ID NO: 41 is the DNA sequence of mutant (E421K) Taq DNA polymerase with a C terminal Histag.
SEQ ID NO: 42 is the protein sequence of mutant (E421K) Taq DNA polymerase with a C terminal Histag.
SEQ ID NO: 43 is the DNA sequence of mutant (L461S) Taq DNA polymerase with a C terminal Histag.
SEQ ID NO: 44 is the protein sequence of mutant (L461S) Taq DNA polymerase with a C terminal Histag.
SEQ ID NO: 45 is the DNA sequence of mutant (A472F) Taq DNA polymerase with a C terminal Histag.
SEQ ID NO: 46 is the protein sequence of mutant (A472F) Taq DNA polymerase with a C terminal Histag.
SEQ ID NO: 47 is the DNA sequence of mutant (E497K) Taq DNA polymerase with a C terminal Histag.
SEQ ID NO: 48 is the protein sequence of mutant (E497K) Taq DNA polymerase with a C terminal Histag.
SEQ ID NO: 49 is the DNA sequence of mutant (L498S) Taq DNA polymerase with a C terminal Histag.
SEQ ID NO: 50 is the protein sequence of mutant (L498S) Taq DNA polymerase with a C terminal Histag.
SEQ ID NO: 51 is the DNA sequence of mutant (E524K) Taq DNA polymerase with a C terminal Histag.
SEQ ID NO: 52 is the protein sequence of mutant (E524K) Taq DNA polymerase with a C terminal Histag.
SEQ ID NO: 53 is the DNA sequence of mutant (D551R) Taq DNA polymerase with a C terminal Histag.
SEQ ID NO: 54 is the protein sequence of mutant (D551R) Taq DNA polymerase with a C terminal Histag.
SEQ ID NO: 55 is the DNA sequence of mutant (R556D) Taq DNA polymerase with a C terminal Histag.
SEQ ID NO: 56 is the protein sequence of mutant (R556D) Taq DNA polymerase with a C terminal Histag.
SEQ ID NO: 57 is the DNA sequence of mutant (S679I) Taq DNA polymerase with a C terminal Histag.
SEQ ID NO: 58 is the protein sequence of mutant (S679I) Taq DNA polymerase with a C terminal Histag.
SEQ ID NO: 59 is the DNA sequence of mutant (L789S) Taq DNA polymerase with a C terminal Histag.
SEQ ID NO: 60 is the protein sequence of mutant (L789S) Taq DNA polymerase with a C terminal Histag.
SEQ ID NO: 61 is the DNA sequence of mutant (E189K/E507K/E742K) Taq DNA polymerase with a C terminal Histag.
SEQ ID NO: 62 is the protein sequence of mutant (E189K/E507K/E742K) Taq DNA polymerase with a C terminal Histag.
SEQ ID NO: 63 is the DNA sequence of the 2019-nCoV_N2 Forward Primer.
SEQ ID NO: 64 is the DNA sequence of the 2019-nCoV_N2 Reverse Primer.
SEQ ID NO: 65 is the DNA sequence of the 2019-nCoV_N2 Probe.

The respective DNA and protein sequences of wild type Taq DNA polymerase and each mutant above, with a C terminal Histag, is shown in the sequence listing attached.

DETAILED DESCRIPTION

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

The term "labeled probe" refers to a labeling probe used in an amplification reaction, typically for quantitative or qPCR analysis, as well as end-point analysis. Such labeling probes may be used to monitor the amplification of the target polynucleotide, and are suitable for monitoring the amount of amplicon(s) produced as a function of time. Such oligonucleotide labeling probes include, but are not limited to, the 5'-exonuclease assay TaqMan labeling probes (see U.S. Pat. No. 5,538,848), various stem-loop molecular beacons (see e.g., U.S. Pat. Nos. 6,103,476 and 5,925,517, stemless or linear beacons (WO 99/21881), PNA Molecular Beacons (see, e.g., U.S. Pat. Nos. 6,355,421 and 6,593,091), linear PNA beacons, non-FRET labeling probes (see, e.g., U.S. Pat. No. 6,150,097), Sunrise/Amplifluor labeling probes (U.S. Pat. No. 6,548,250), stem-loop and duplex Scorpion labeling probes (U.S. Pat. No. 6,589,743), bulge loop labeling probes (U.S. Pat. No. 6,590,091), pseudo knot labeling probes (U.S. Pat. No. 6,589,250), cyclicons (U.S. Pat. No. 6,383,752), hairpin labeling probes (U.S. Pat. No. 6,596,490), peptide nucleic acid (PNA) light-up labeling probes, self-assembled nanoparticle labeling probes, and ferrocene-modified labeling probes described, for example, in U.S. Pat. No. 6,485,901. Labeling probes can also comprise black hole quenchers (Biosearch), Iowa Black (IDT), QSY quencher (Molecular Labeling probes), and Dabsyl and Dabcel sulfonate/carboxylate Quenchers (Epoch). Labeling probes can also comprise two labeling probes, wherein for example a fluorophore is on one probe, and a quencher on the other, wherein hybridization of the two labeling probes together on a target quenches the signal, or wherein hybridization on target alters the signal signature via a change in fluorescence. Labeling probes can also comprise sulfonate derivatives of fluorescein dyes with a sulfonic acid group instead of the carboxylate group, phosphoramidite forms of fluorescein, phosphoramidite forms of CY 5 (available from Amersham).

The term "sample" refers to biological samples from any source which include nucleic acid or DNA.

The term "real time quantitative PCR" and "real time qPCR", is used interchangeably with the term "quantitative PCR" (abbreviated "qPCR"), and refers to a method for simultaneous amplification, detection, and quantification of a target polynucleotide using labeled probes during PCR and further includes the protocols in the examples herein and such methods as TaqMan, SYBR Green assays, and the like;

whether in a system performing quantitative real-time PCR or semi-quantitative real-time PCR.

The term "target," refers to a polynucleotide sequence that is sought to be amplified and can exist in the presence of other nucleic acid molecules or within a larger nucleic acid molecule or in a sample. The target polynucleotide can be obtained from any source, and can DNA or cDNA from RNA, or can be methylated, non-methylated, or both.

The term "threshold cycle" or "CT" is defined as a fractional cycle number at which a reporter signal rises above a threshold value, including where DNA quantification by real-time PCR relies on plotting fluorescence against the number of cycles on a logarithmic scale. A threshold for detection of DNA-based fluorescence is, preferably, set 3-5 times of the standard deviation of the signal noise above background. The number of cycles at which the fluorescence exceeds the threshold is called the threshold cycle (Ct) or quantification cycle (Cq).

The term "threshold" or "threshold value" is defined as the reporter signal value that is used for calculation of threshold cycle (CT).

The term "reporter signal" is defined as the signal generated by a PCR product reporter (typically a dye or a labeled probe) which is correlated with the concentration of PCR product, in an assay for measuring biological data, including but not limited to data for cycling reactions. Examples of suitable data include but are not limited to, fluorescent signal data, optical signal data, magnetic signal data, and electronic signal data. Suitable assays include DNA quantification by qPCR. The reporter signal can be generated by a DNA-binding or intercalating dye (e.g. SYBR Green or EvaGreen) that binds to all double-stranded (ds) DNA in PCR, increasing the fluorescence quantum yield of the dye, and leading to an increase in fluorescence intensity measured at each cycle. The assay should be adjusted so that the increasing signal intensity does not interfere with, or prevent, accurate quantification of the target.

The mutant Taq polymerase of the invention is suited to improved efficiency qPCR where the cycling includes using a rapid extension time of one second per cycle. It can be used with the commonly employed method of varying primers and templates for increasing the efficiency of target amplification, to find the most efficient primer-template combination together with the most efficient mutant Taq polymerase of the invention, as assessed in a titration experiment with serial dilutions of DNA template to create a standard curve of the change in (CT), as determined from reporter signal, with each dilution. The slope of the linear regression is then used to determine the efficiency of amplification, which is 100% if a dilution of 1:2 results in a (CT) difference of 1.

The efficiency of qPCR can also be determined by mechanism-based qPCR quantification methods, which do not require a standard curve for quantification. Methods such as MAK2 (see Boggy G, Woolf P J (2010); Ravasi T (ed.). "A Mechanistic Model of PCR for Accurate Quantification of Quantitative PCR Data" PLOS ONE 5 (8): e12355) have been shown to have equal or better quantitative performance to standard curve methods. These mechanism-based methods use knowledge about the polymerase amplification process to generate estimates of the original sample concentration and amplification.

Real-time or qPCR with the mutant Taq DNA polymerase of the invention can also be used to quantify nucleic acids, and monitor gene expression, by relative quantification and absolute quantification. Absolute quantification gives the exact number of target DNA molecules by comparison with DNA standards using a calibration curve; which necessitates that the PCR of the sample and the standard have the same amplification efficiency. The mutant Taq DNA polymerase of the invention provides a faster cycle time with a consistent and increased efficiency, making them suitable for absolute quantification. The same properties of the mutant Taq DNA polymerase of the invention also makes them well-suited relative quantification.

Diagnostic qualitative PCR is applied to rapidly detect nucleic acids that are diagnostic of, for example, infectious diseases, cancer and genetic abnormalities. The properties of the mutant Taq DNA polymerase of the invention in qPCR assays allows significantly improved diagnosis of infectious diseases, newly emerging diseases, such as new strains of flu and coronavirus, and in diagnostic tests.

Real time or qPCR with the mutant Taq DNA polymerase of the invention can also be used to assay gene expression and provide meaningful information relating to food safety, food spoilage and fermentation and microbial risk assessment of water quality (drinking and recreational waters) and in public health protection.

Real time or qPCR with the mutant Taq DNA polymerase of the invention may also be used to amplify taxonomic or functional markers of genes in environmentally relevant samples to help determine, e.g., the amount of microorganisms in a sample, and/or, can identify different families, genera, or species based on the marker. Real time or qPCR with the mutant Taq DNA polymerase of the invention may also be used for functional markers (protein-coding genes) to show gene expression within a community, which may reveal information about the environment.

Real time or qPCR with the mutant Taq DNA polymerase of the invention may also be used to detect agricultural pathogens, including those attacking plant propagules or seedlings. Real time or qPCR with the mutant Taq DNA polymerase of the invention may also be used in systems that allow detection and discrimination of small amounts of pathogens like the *Phytophthora ramorum*, an oomycete that kills Oaks and other species, even when mixed in with the DNA of the host plant.

Real time or qPCR with the mutant Taq DNA polymerase of the invention may also be used to detect GMOs given the sensitivity and dynamic range offered in detecting associated sequences, using specific primers that amplify not the transgene but the promoter, terminator or even intermediate sequences used during the process of engineering the vector. As the process of creating a transgenic plant normally leads to the insertion of more than one copy of the transgene its quantity can also be assessed with the mutant Taq DNA polymerase of the invention.

The use of qPCR with the mutant Taq DNA polymerase of the invention allows both the quantification and genotyping (characterization of the strain, carried out using melting curves) of a virus. The degree of infection, quantified with the mutant Taq DNA polymerase of the invention as the copies of the viral genome per unit of the patient's tissue, is relevant in many diagnoses.

EXAMPLES

In gene expression analysis with the Taq DNA polymerase mutants of the invention, one typically performs RNA extraction form the sample followed by reverse transcription, to generate cDNA as the target. The cDNA target can be efficiently quantified with the Taq DNA polymerase mutants of the invention, and one of the methods describe above, where a reporter signal is monitored for threshold and the CT for the sample(s) is determined.

Production of Mutants

Taq DNA polymerase mutants were generated by conventional inverse PCR mutagenesis. All mutants are sequenced verified, expressed in *E. Coli*, and purified. A C-terminal His tag was added to all Taq DNA polymerase mutants and the wild type for ease of purification.

Exemplary Probe qPCR

Probe qPCR was performed under the following conditions:

The target for the qPCR was the SARS-Co N gene, 2019-nCoV_N2, published by the United States Center for Disease Control for the CDC 2019-nCoV Real-Time RT-PCR Diagnostic Panel.

```
Forward Primer: 2019-nCoV_N2 Forward Primer:
                                        (SEQ ID NO: 63)
TTACAAACATTGGCCGCAAA Reverse Primer: 2019-nCoV_N2 Reverse Primer:
                                        (SEQ ID NO: 64)
GCGCGACATTCCGAAGAA Probe: 2019-nCoV_N2 Probe:
                                        (SEQ ID NO: 65)
FAM-ACA ATT TGC CCC CAG CGC TTC AG-BHQ1
```

Initial target concentration was 10 copies of synthesized Covid 19 N gene per reaction (Twist Bioscience, CA).

Each 20 µl reaction contains 4 µl of 50 ng/µl Taq DNA polymerase, 1 µl of 10 µM Forward primer, 1 µl of 10 µM reverse primer, 1 µl of 5 µM Labelling Probe, 1 µl of 10 copies/µl of Covid 19 N gene, and 2 µl of 10× reaction buffer (which makes final of composition of 20 mM Tris-HCl, 80 mM Tris-Acetate, 10 mM (NH4)2SO4, 10 mM KCl, 2 mM MgSO4, 3 mM Mg-Acetate, 0.1% Triton®-X-100, pH 8.8 @ 25° C.) with water comprising the remaining 10 µl.

The qPCR machine used was the Prime Pro 48 Real-time qPCR machine (Cole-Parmer, UK). The reaction protocol was: 95° C. 30 sec denature, followed by 40 cycles of [95° C. 4 sec annealing, 60° C. 1 sec extension]. Fluorescent signal was collected during each cycle the 60° C. extension step.

Figure 1B:
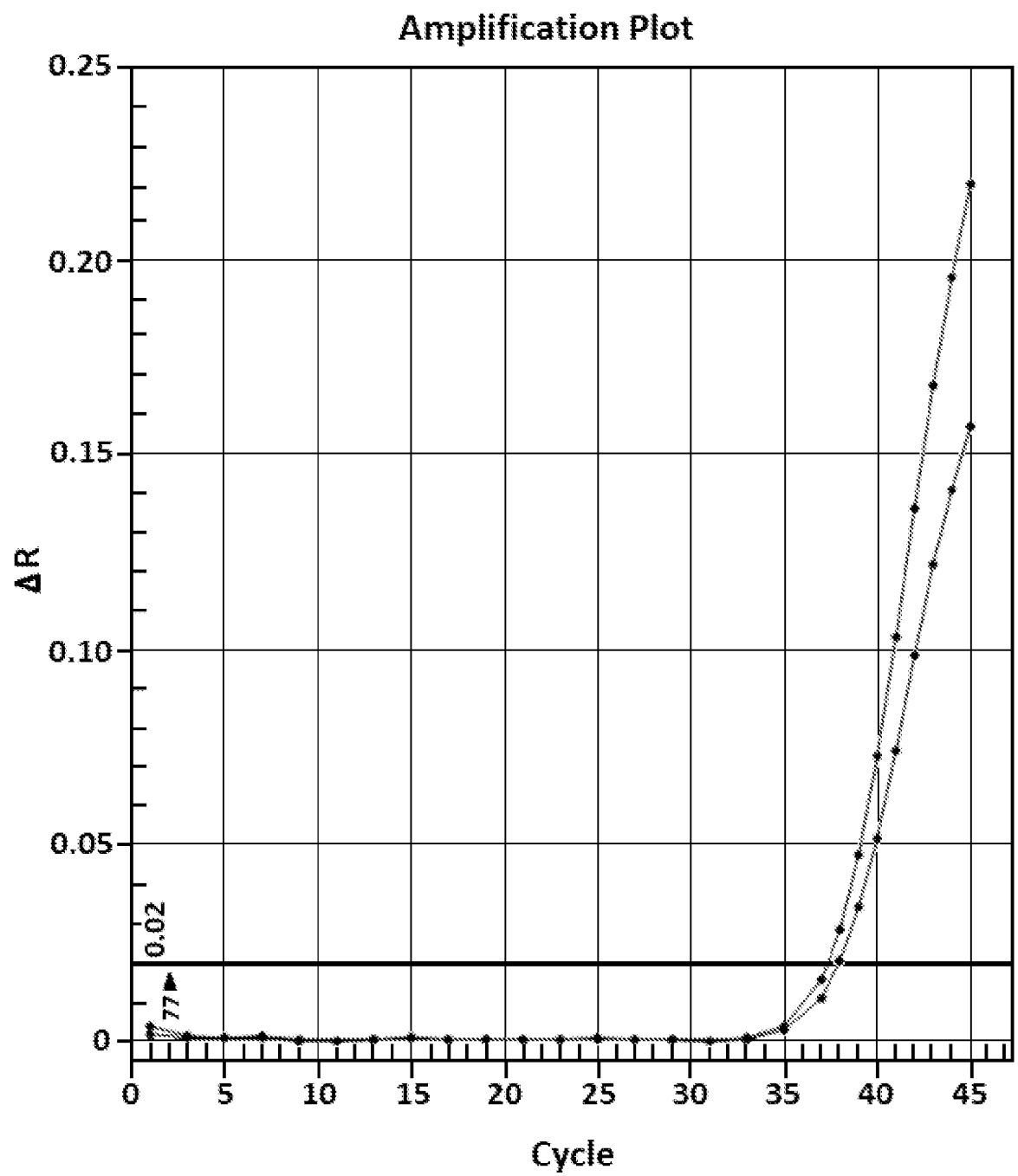
Figure 1C:
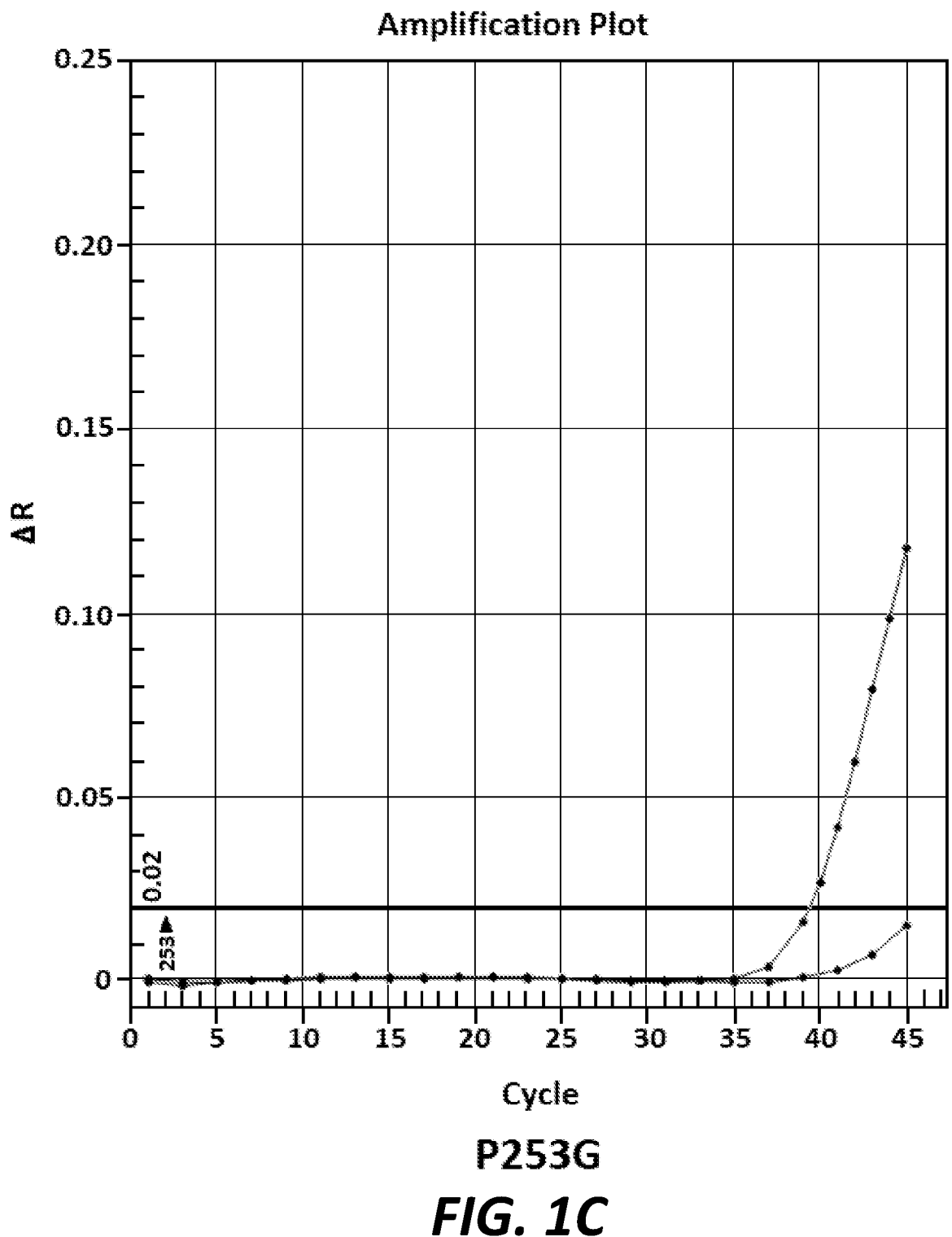
Figure 1D:
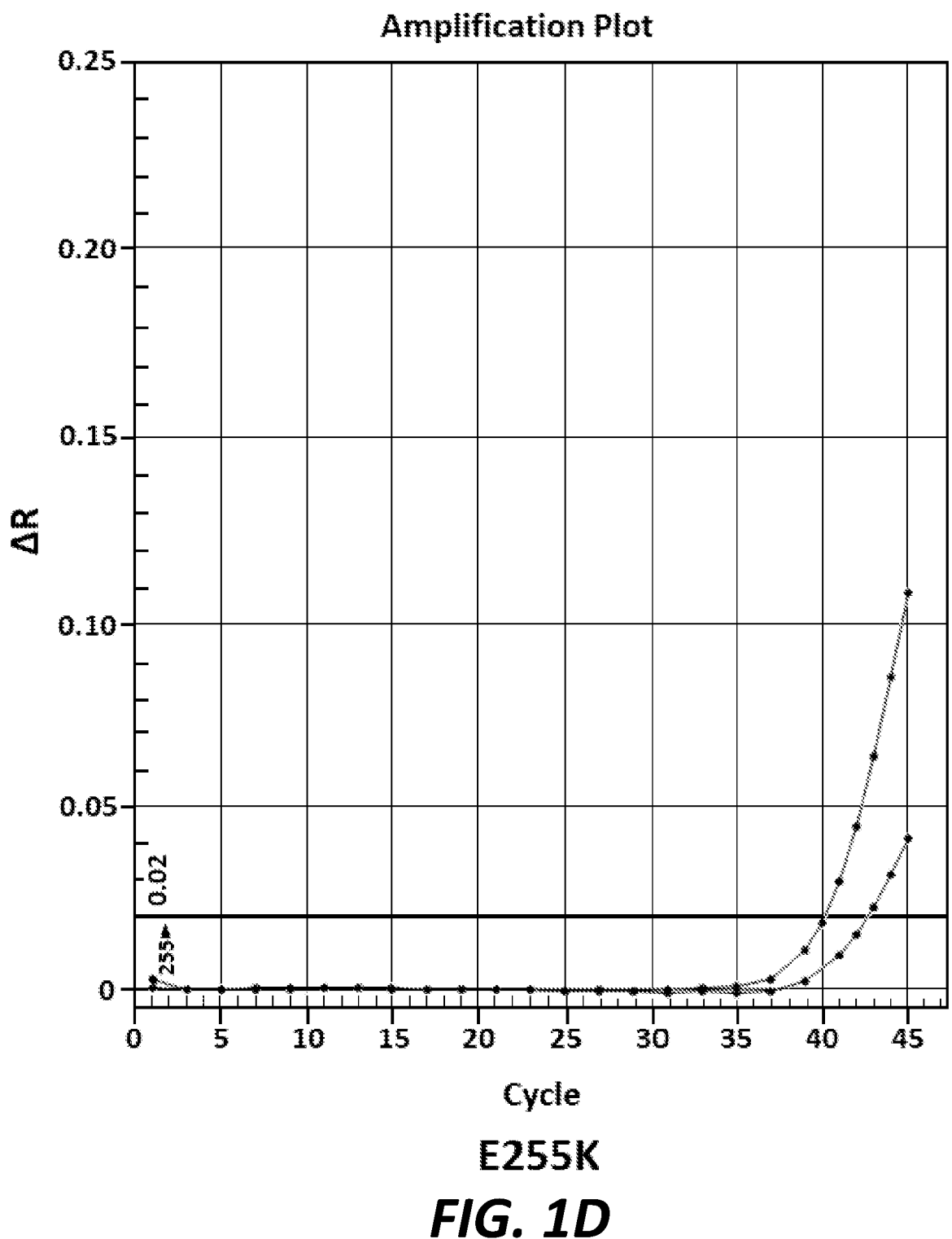
Figure 1E:
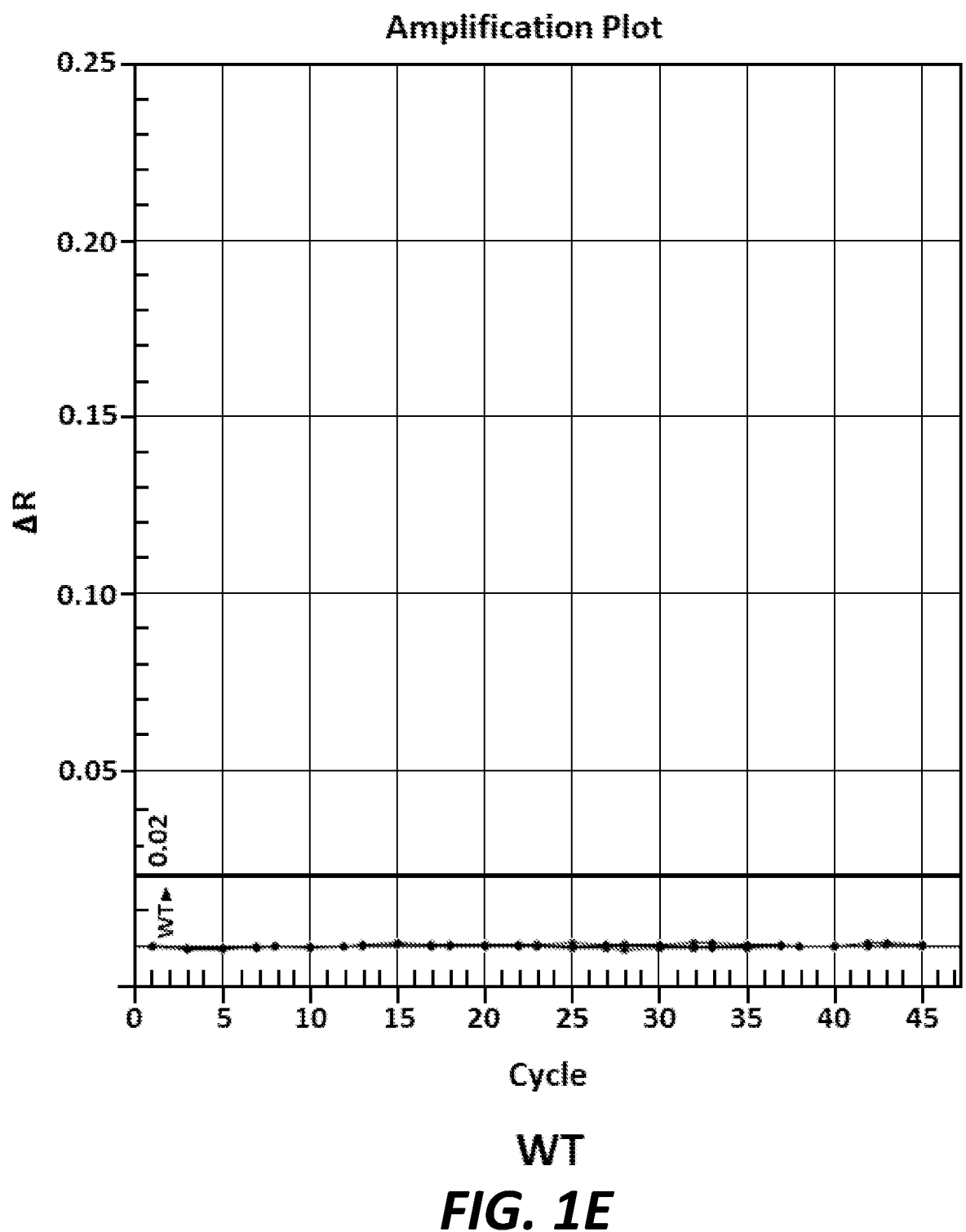
Figure 1F:
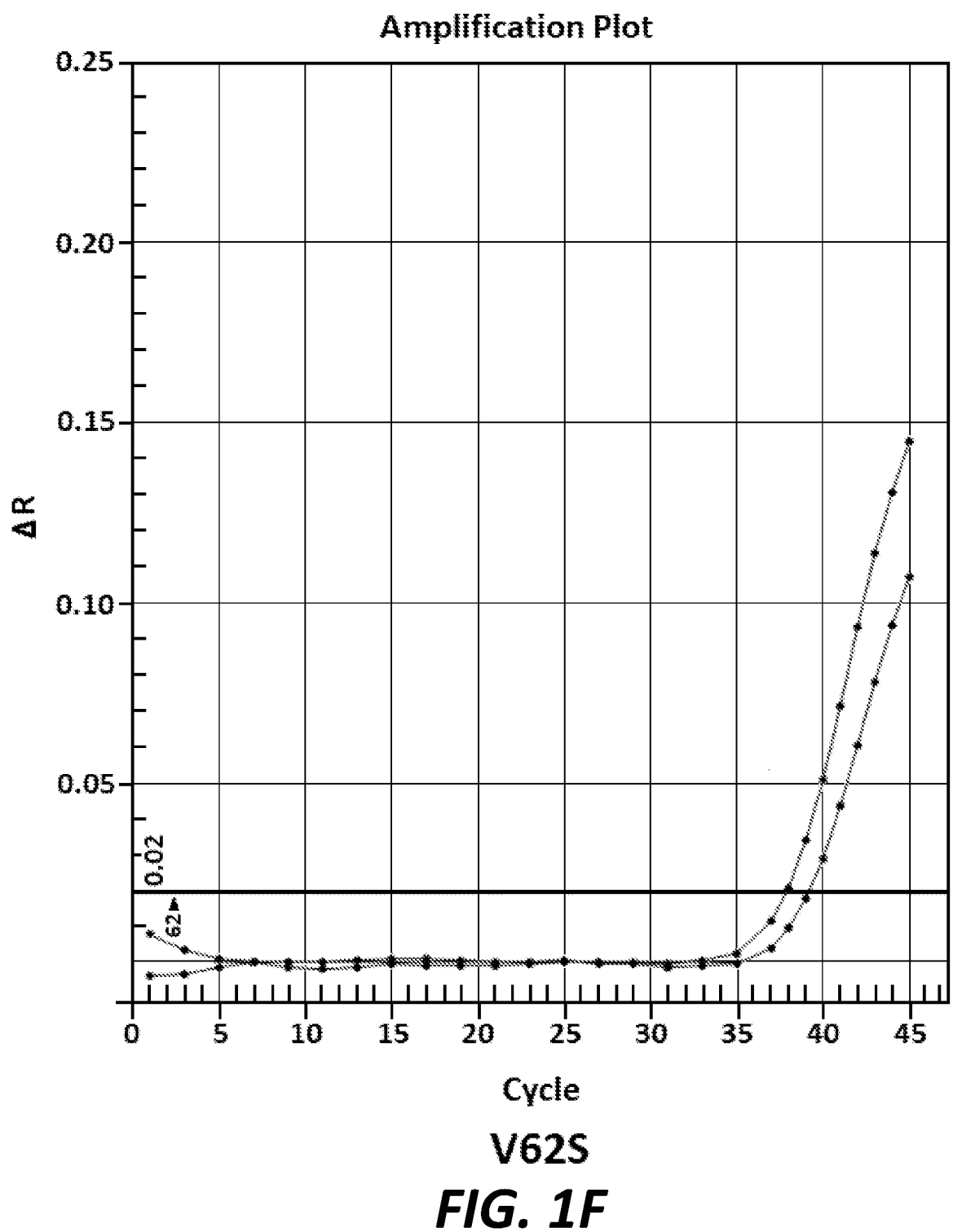
Figure 1G:
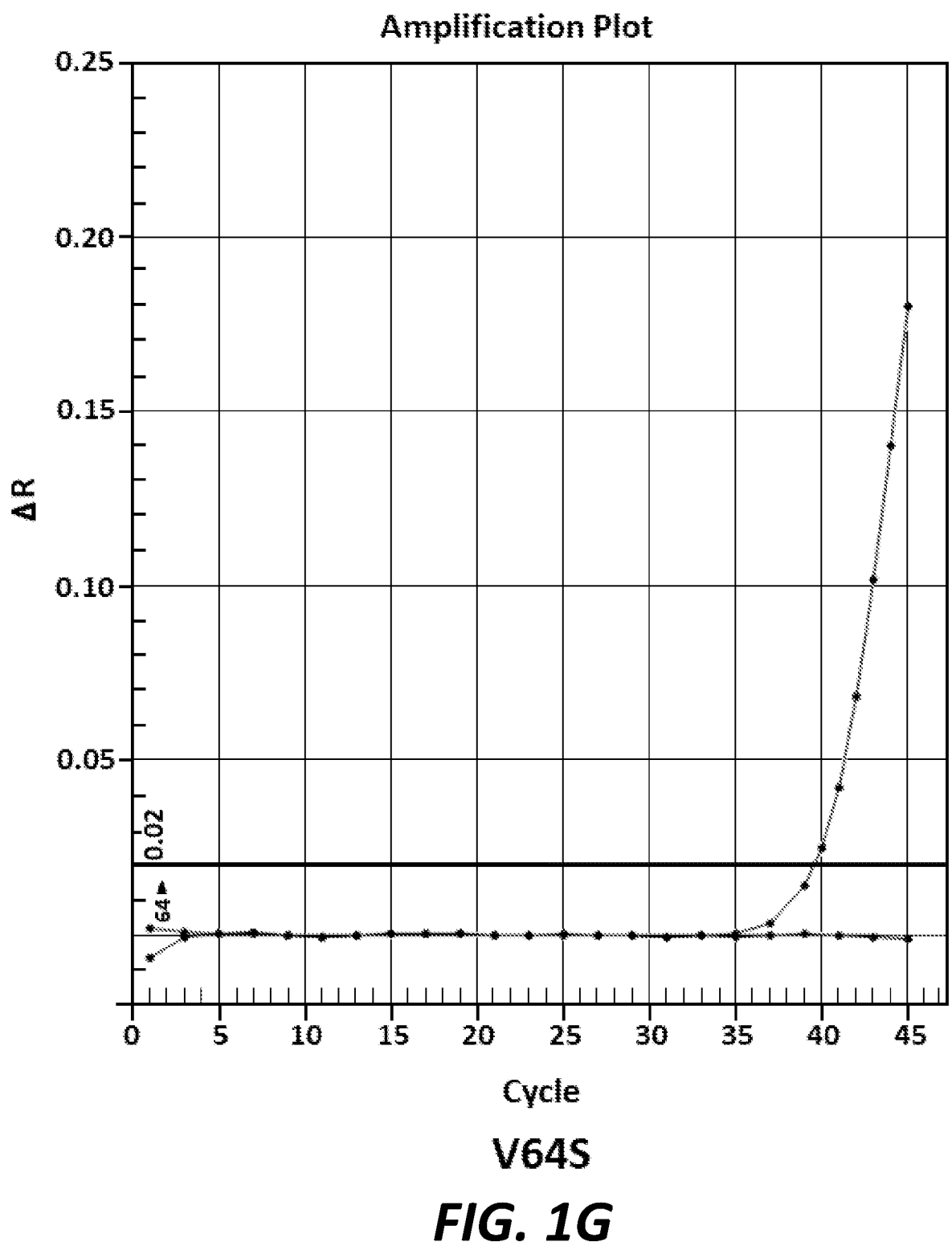
Figure 1H:
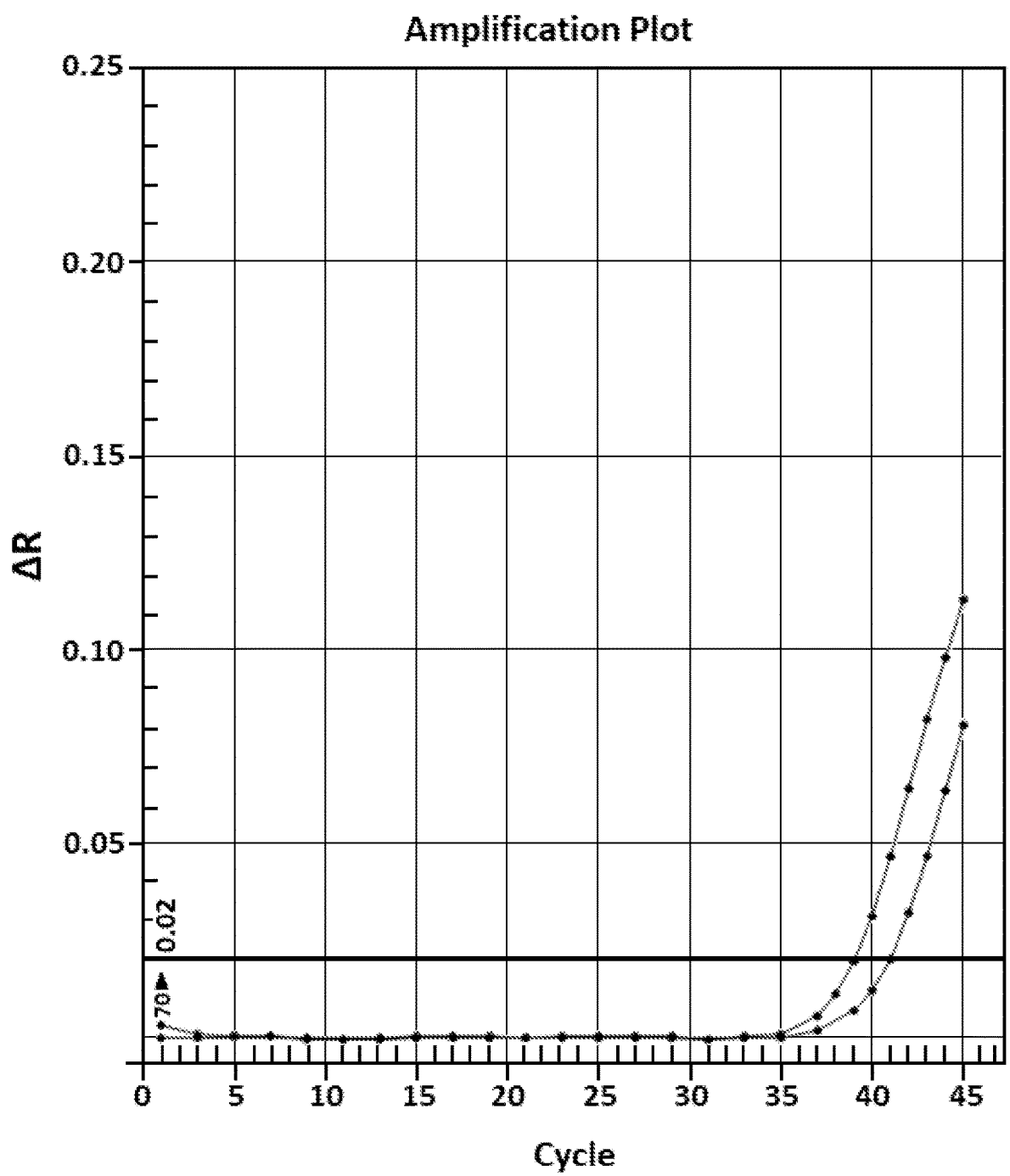
Figure 1I:
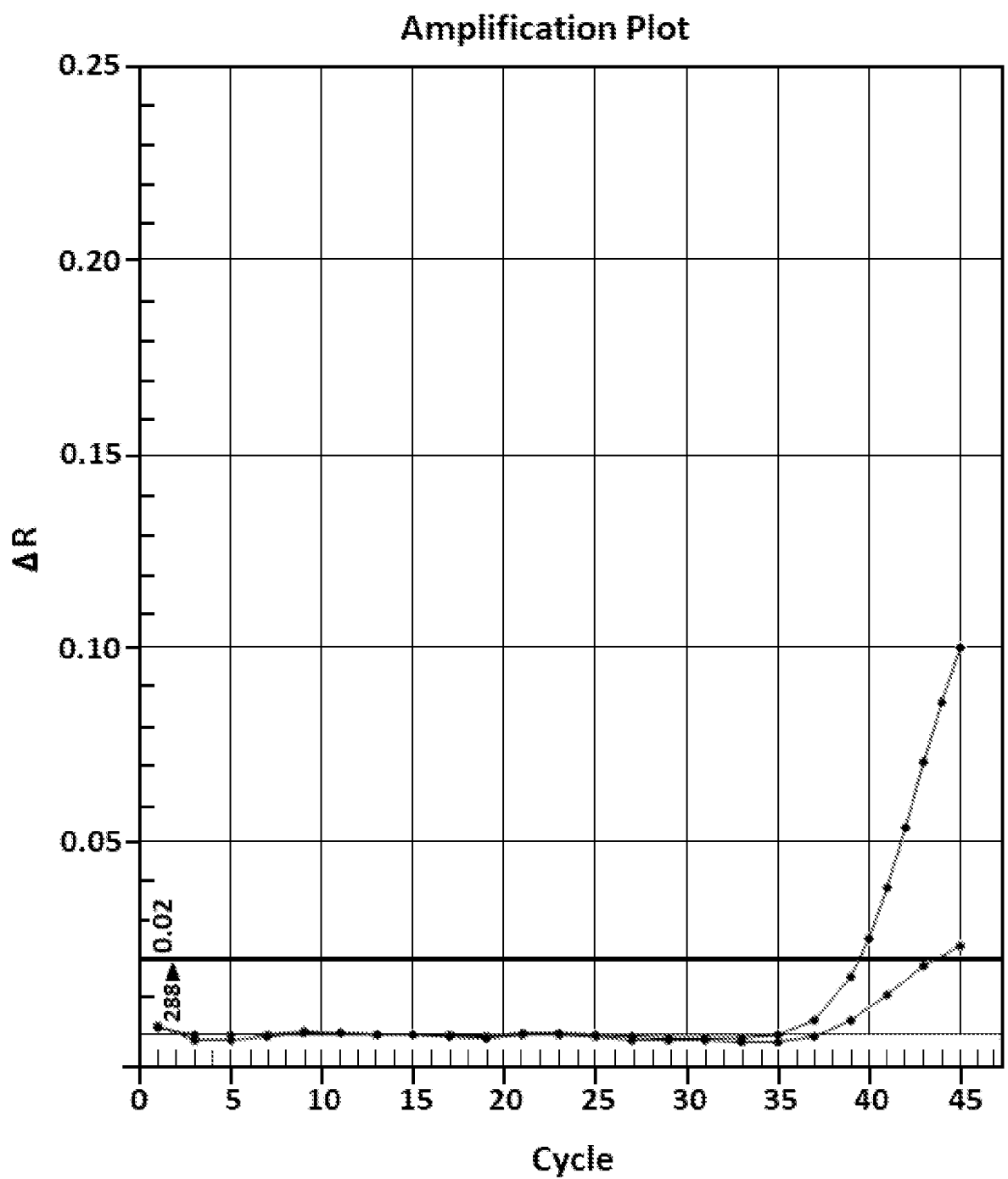
Figure 1J:
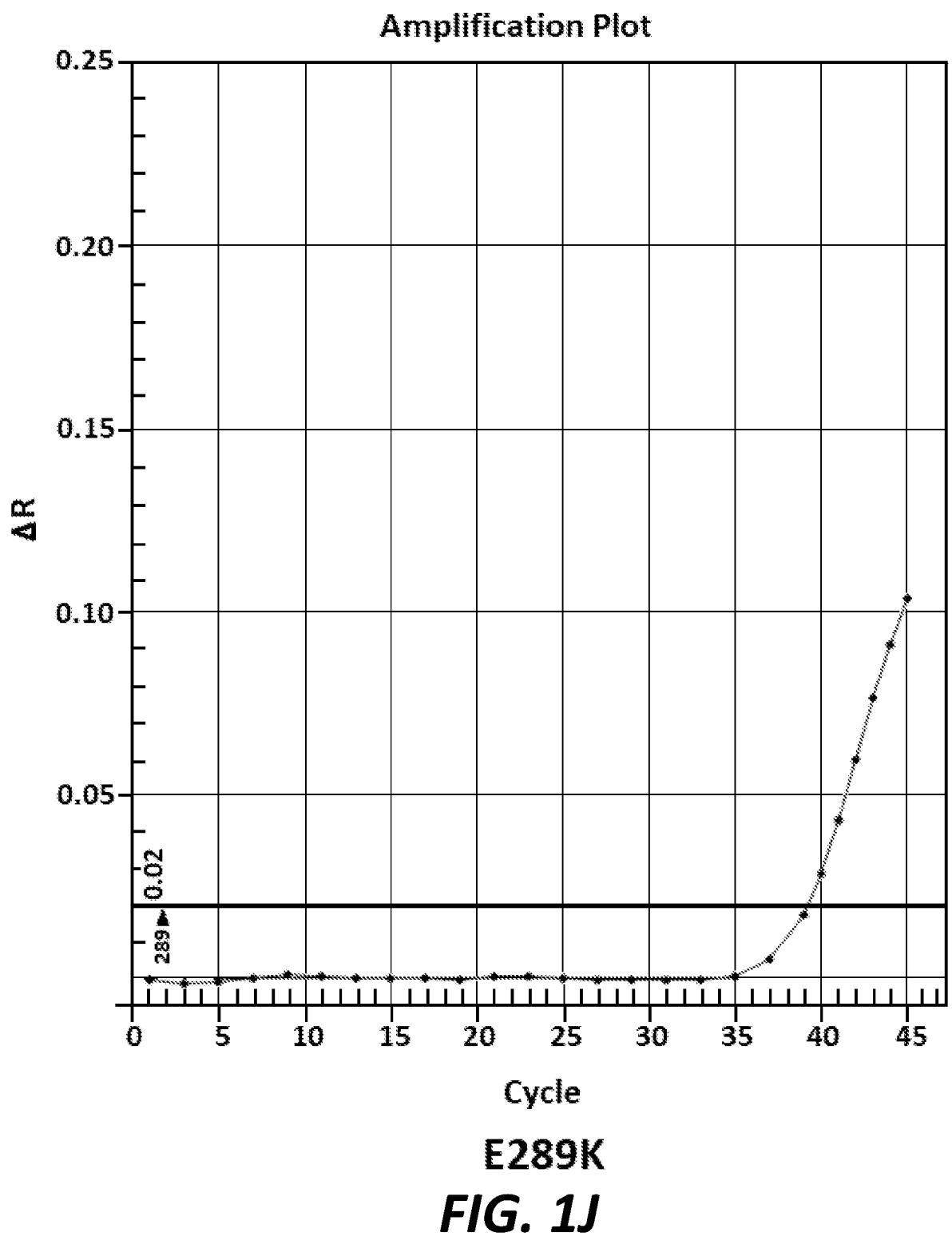
Figure 1K:
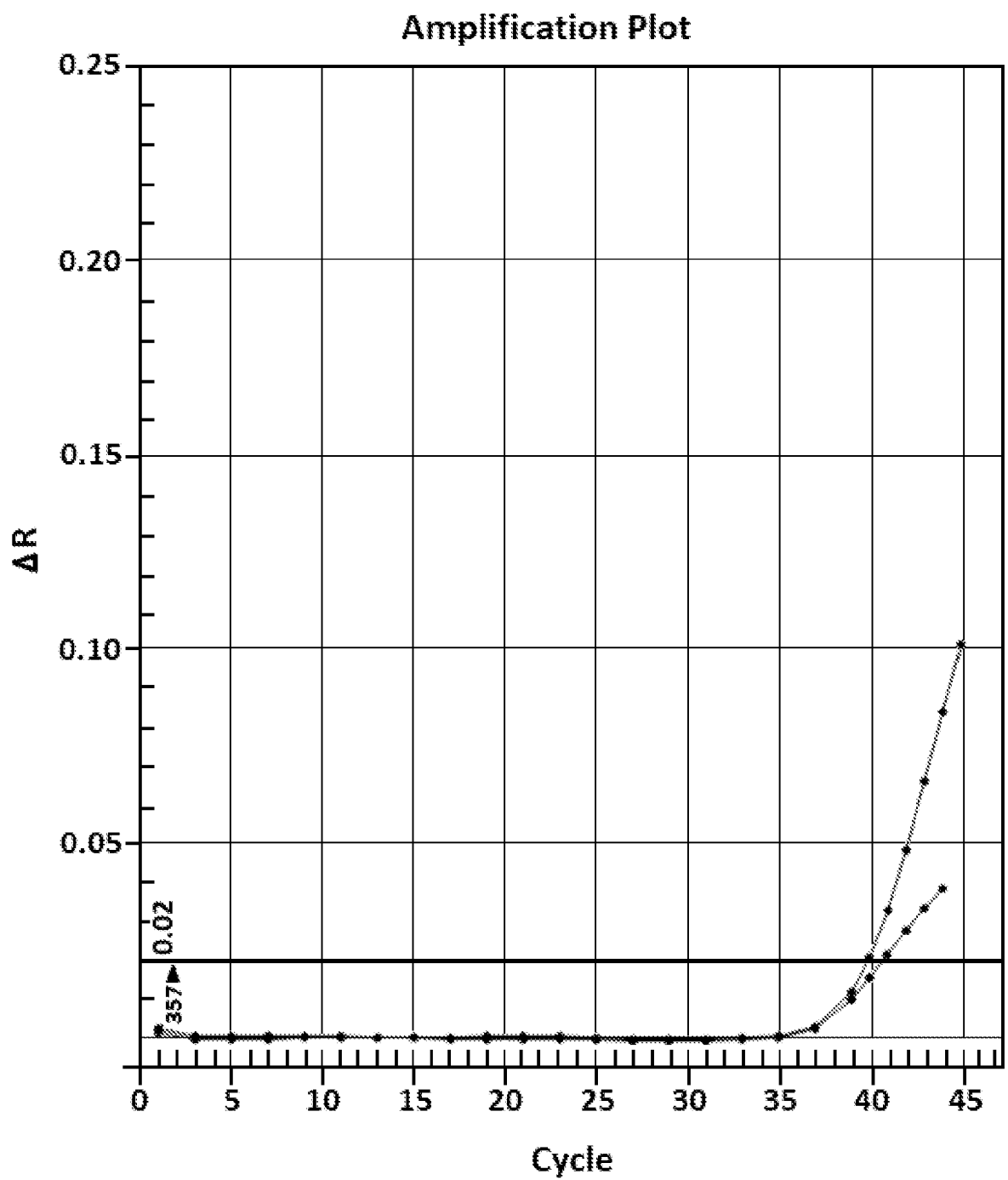
Figure 1L:
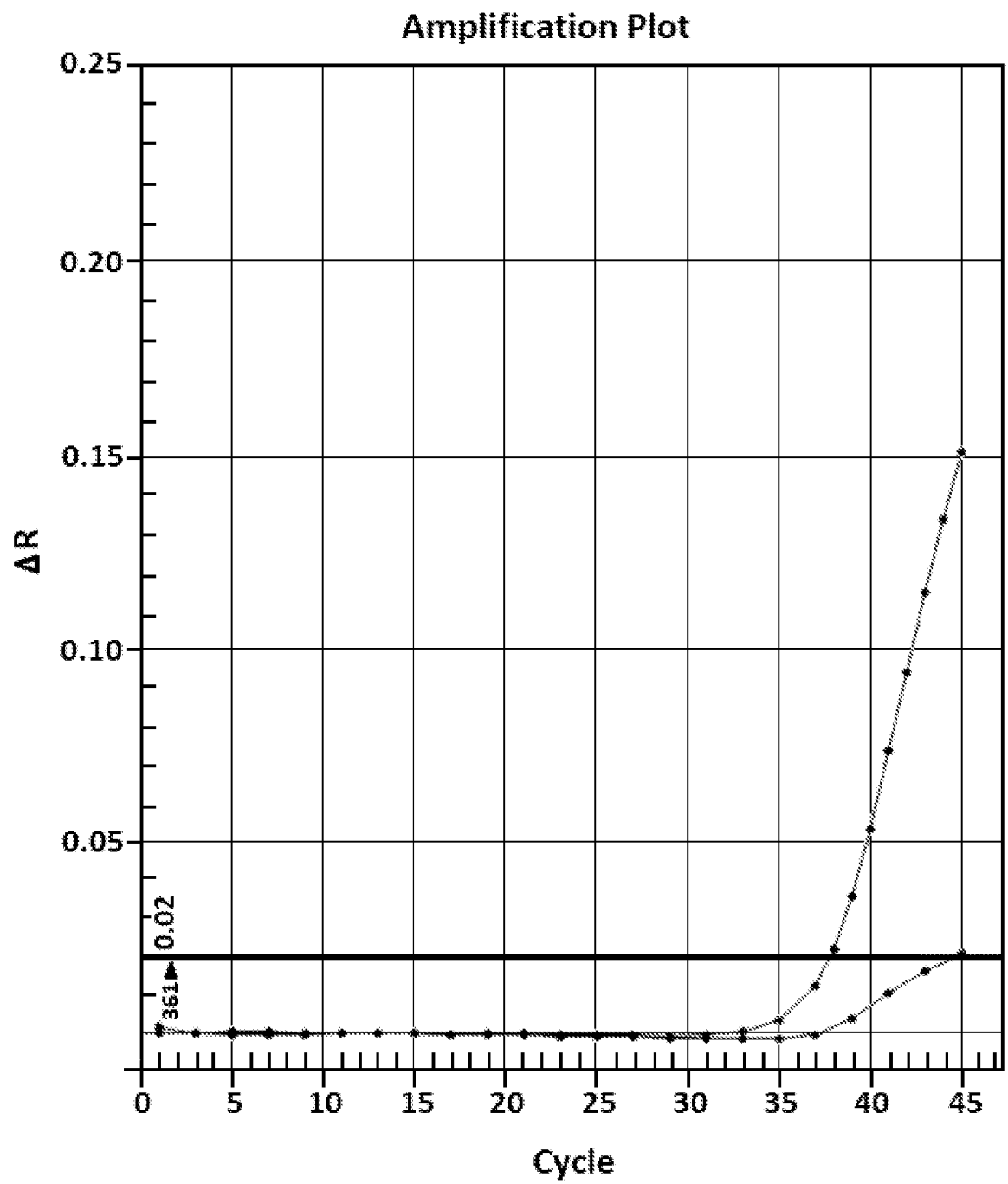
Figure 1M:
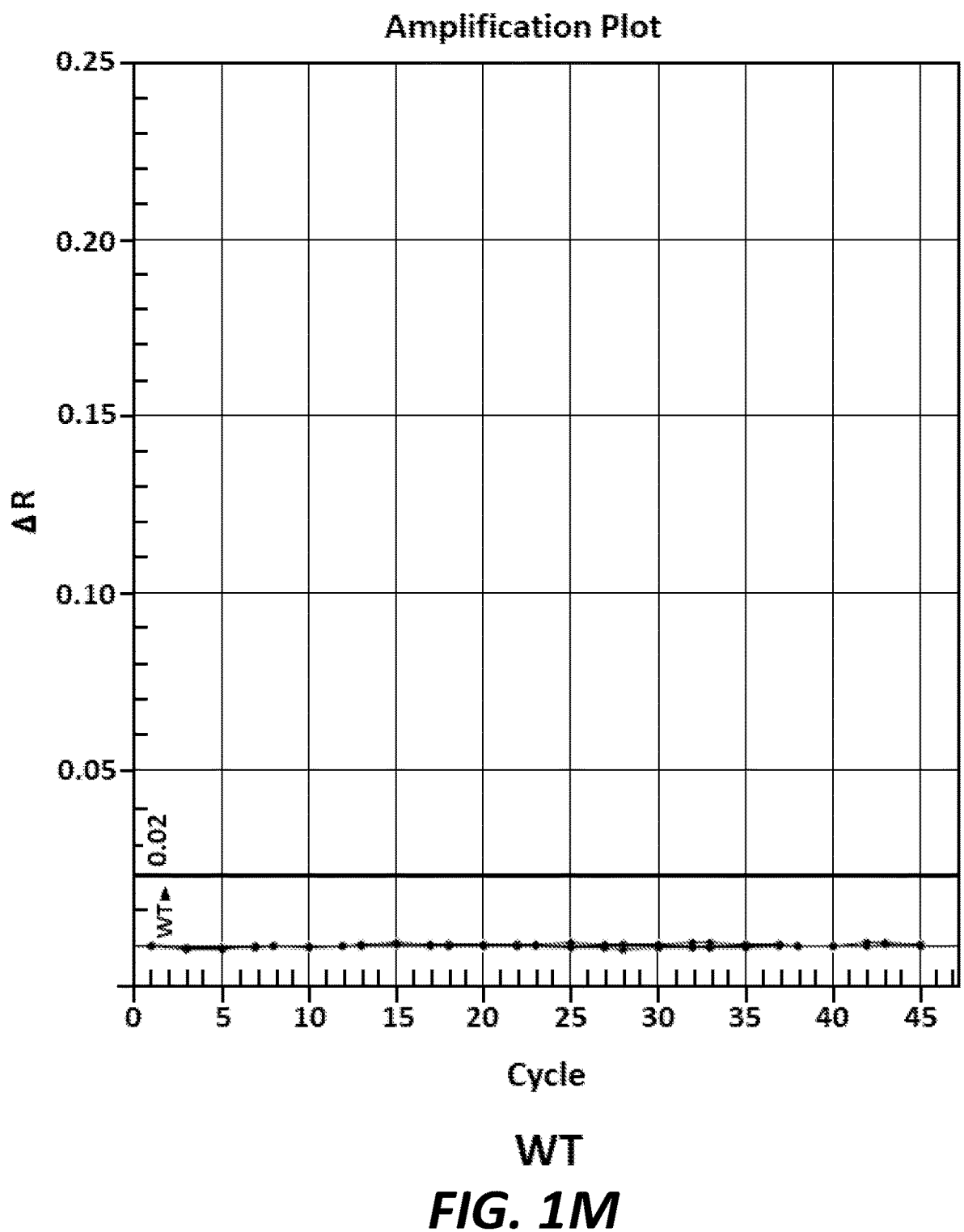
Figure 1N:
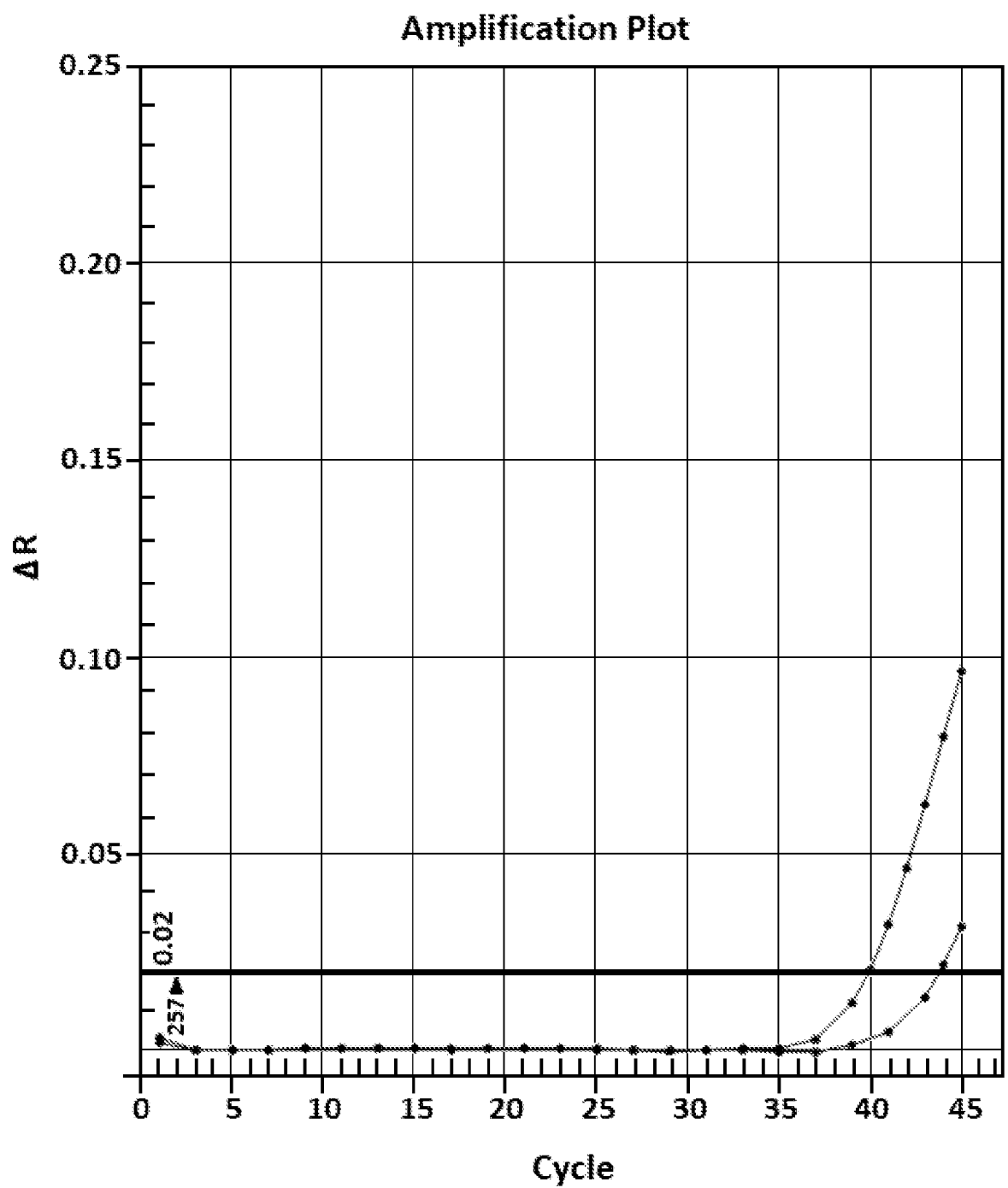
Figure 1O:
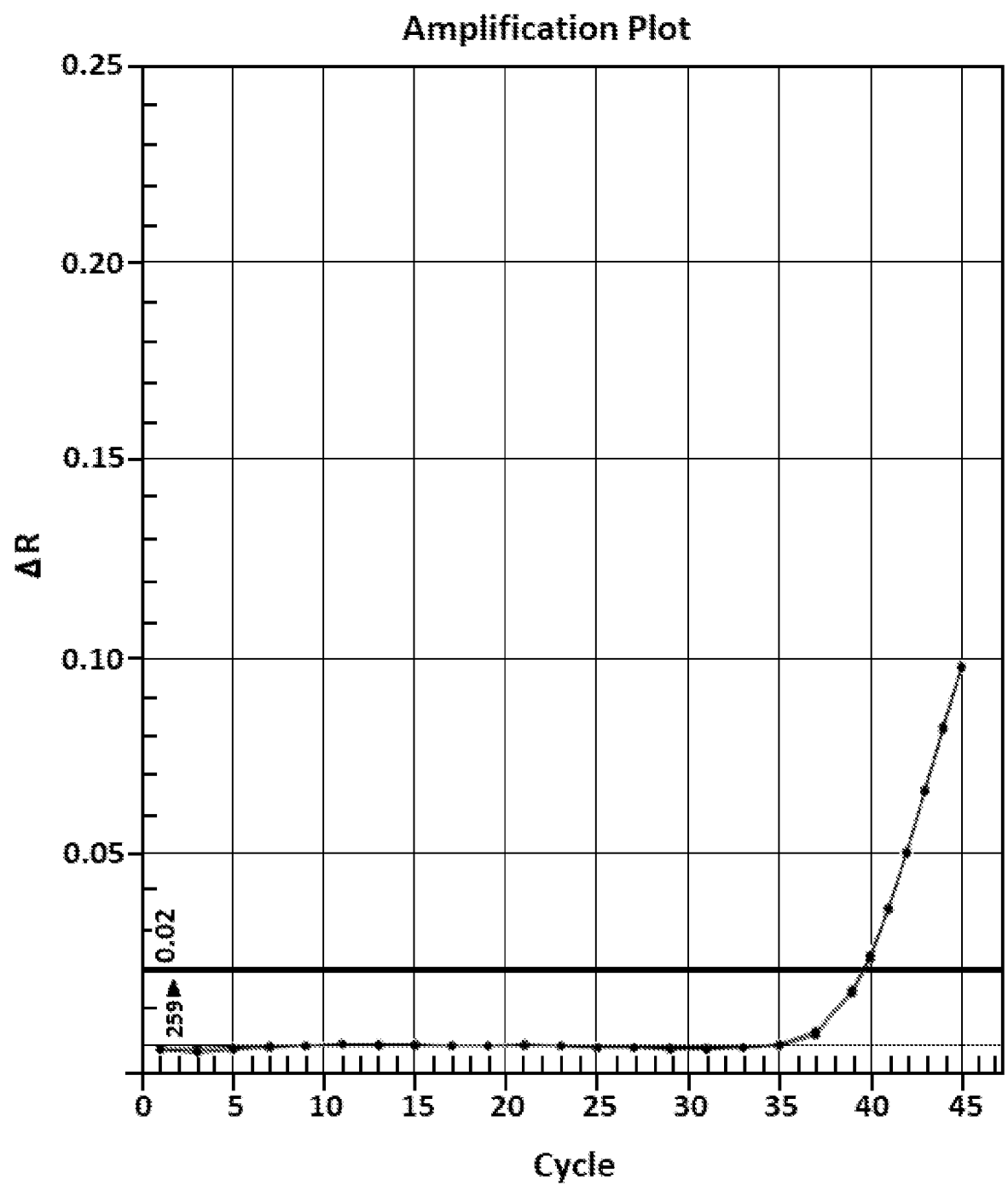
Figure 1P:
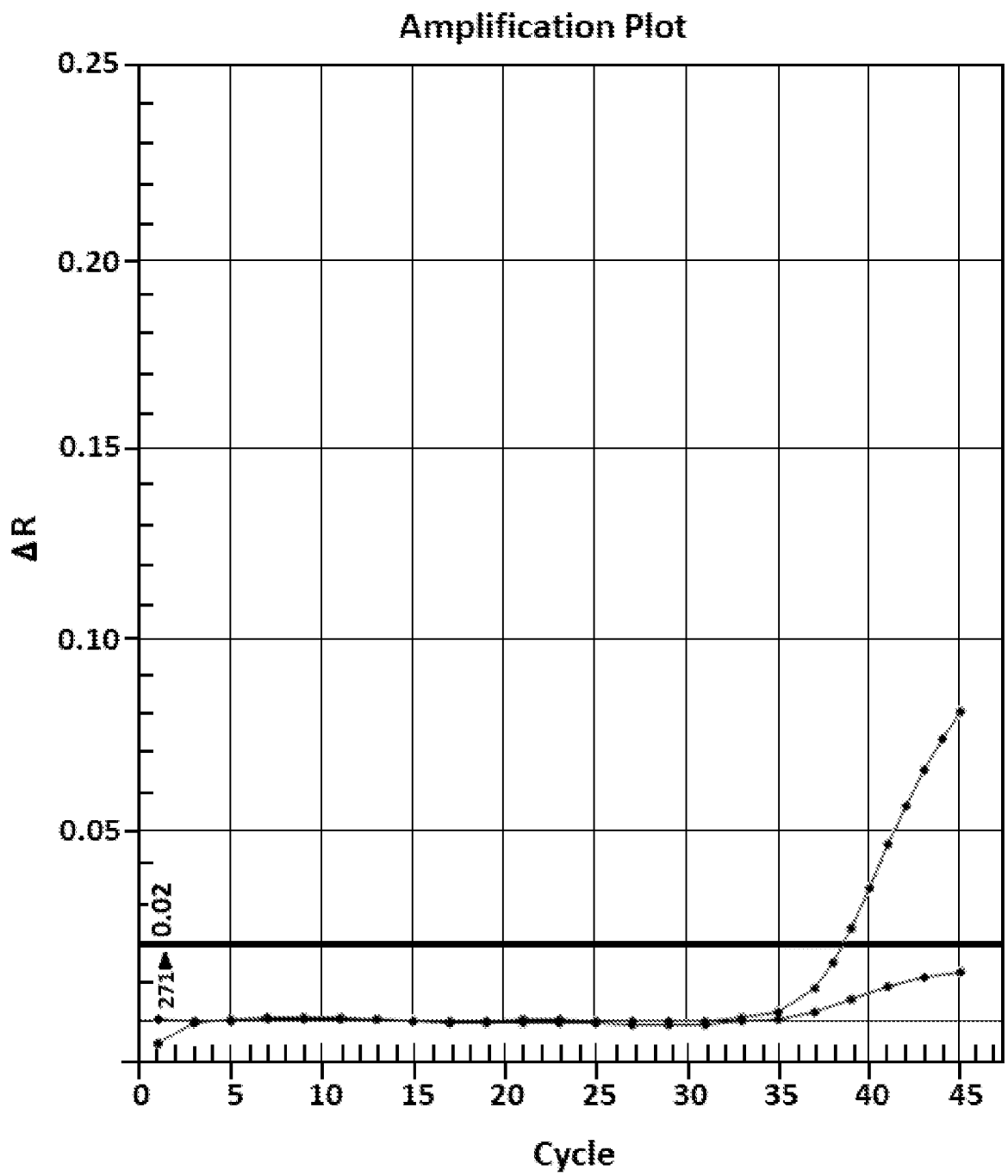
Figure 1Q:
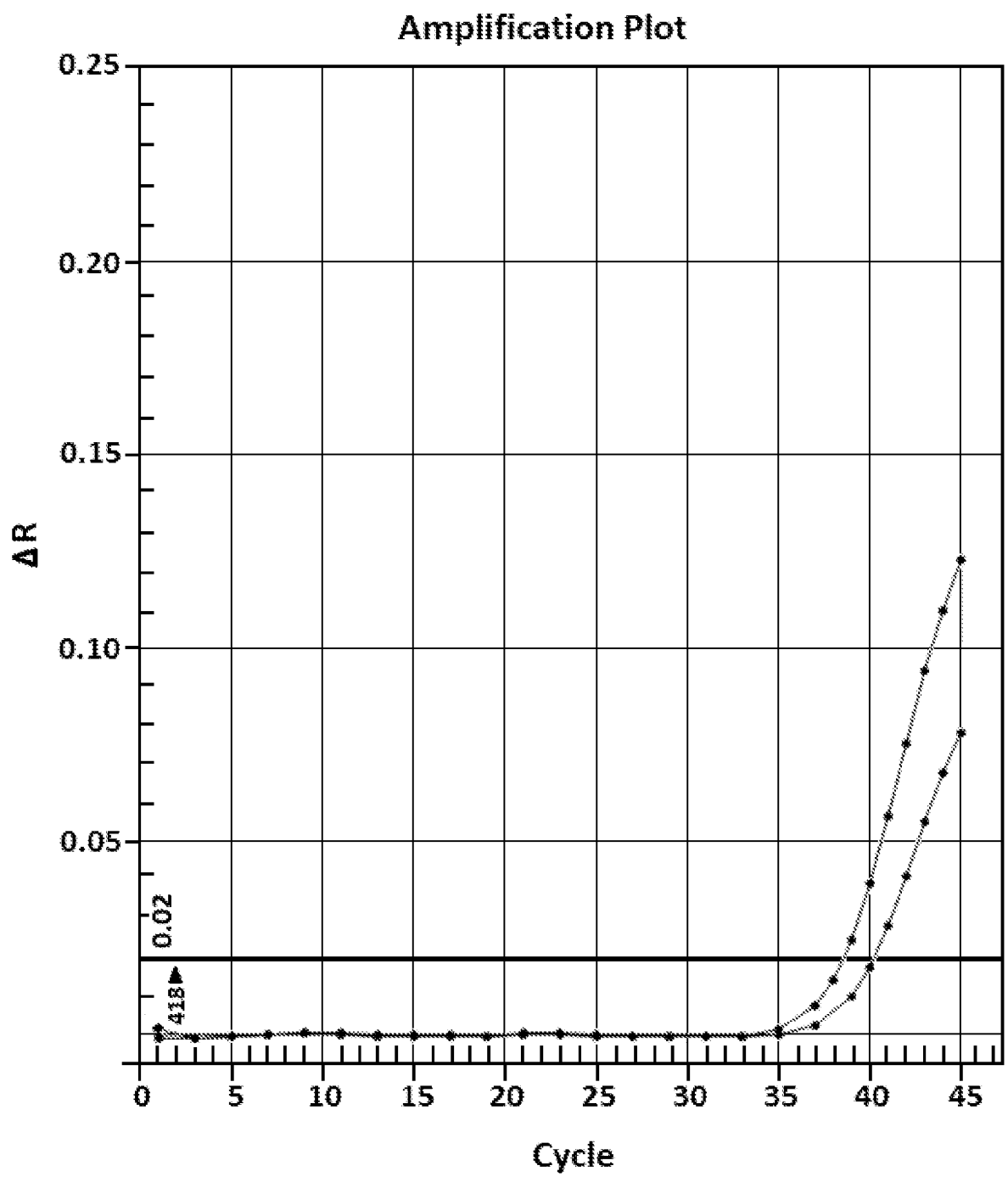
Figure 1R:
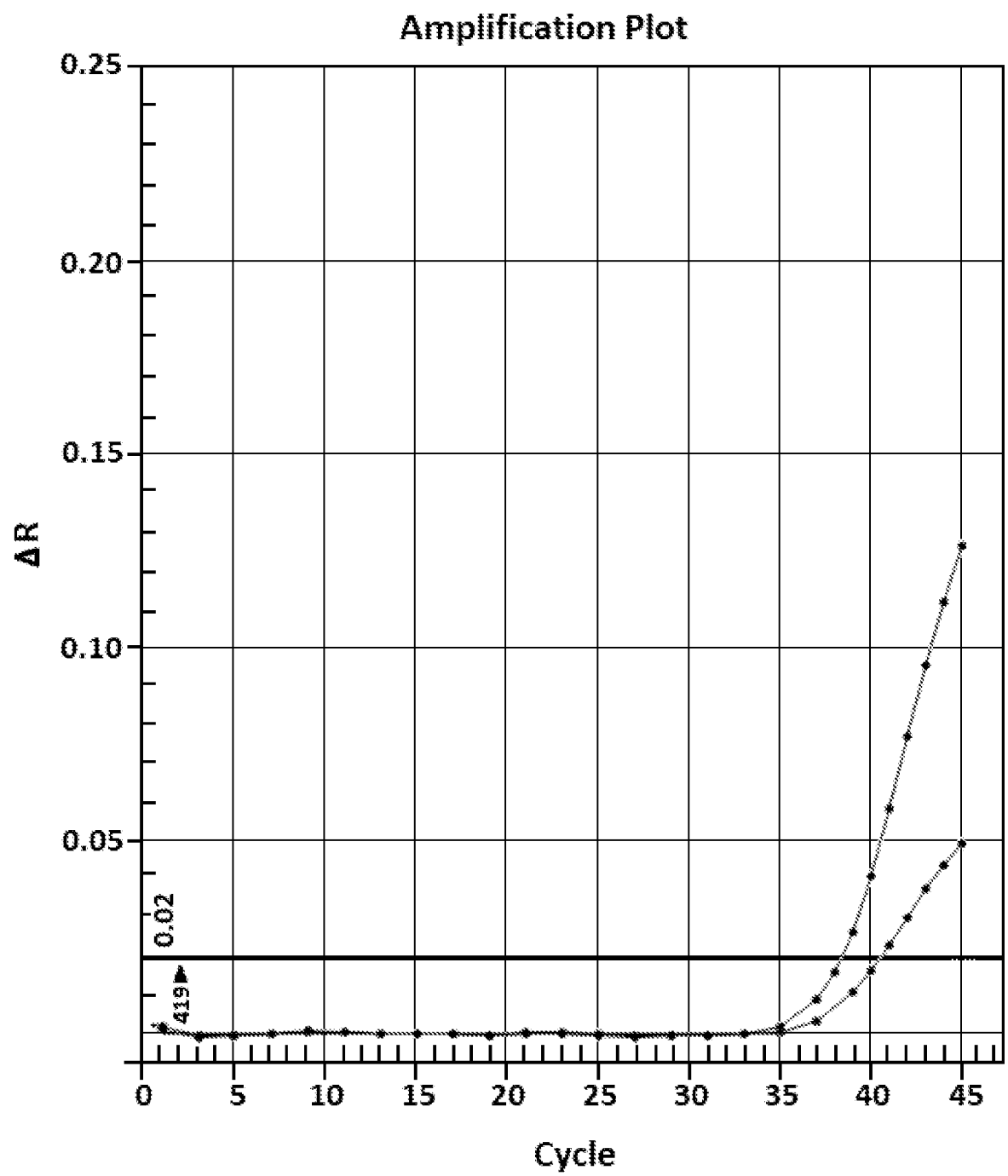
Figure 1S:
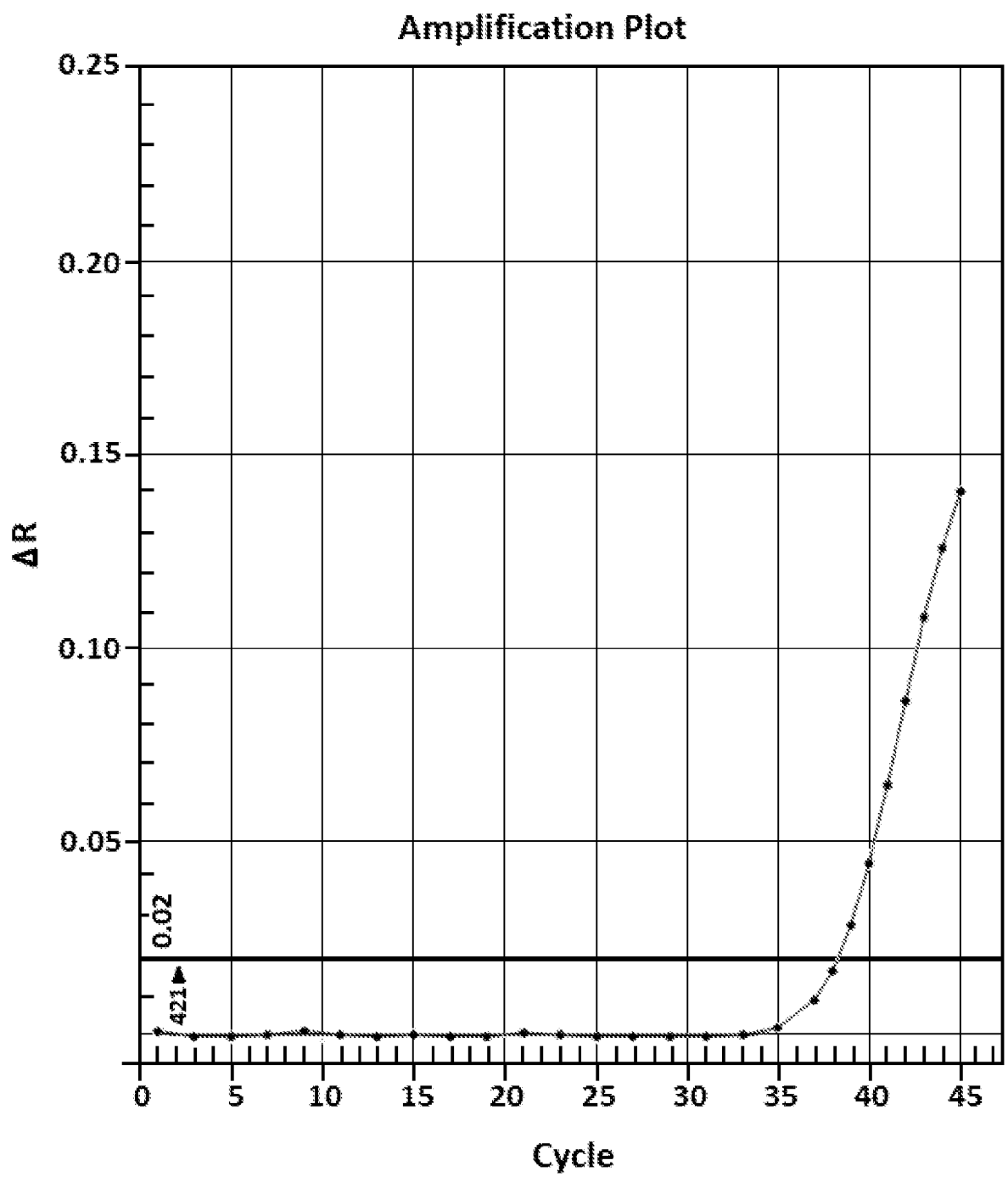
Figure 1T:
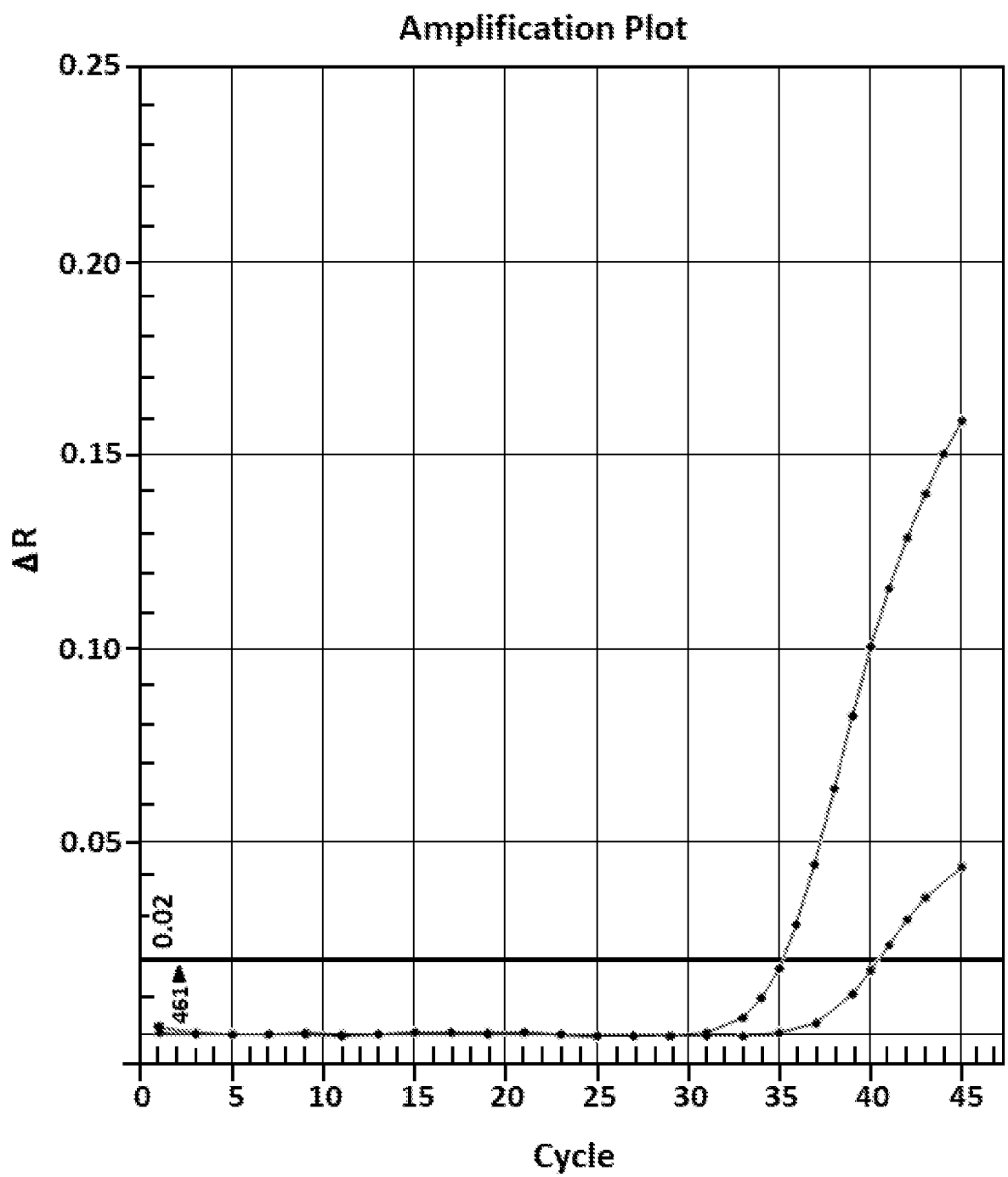
Figure 1U:
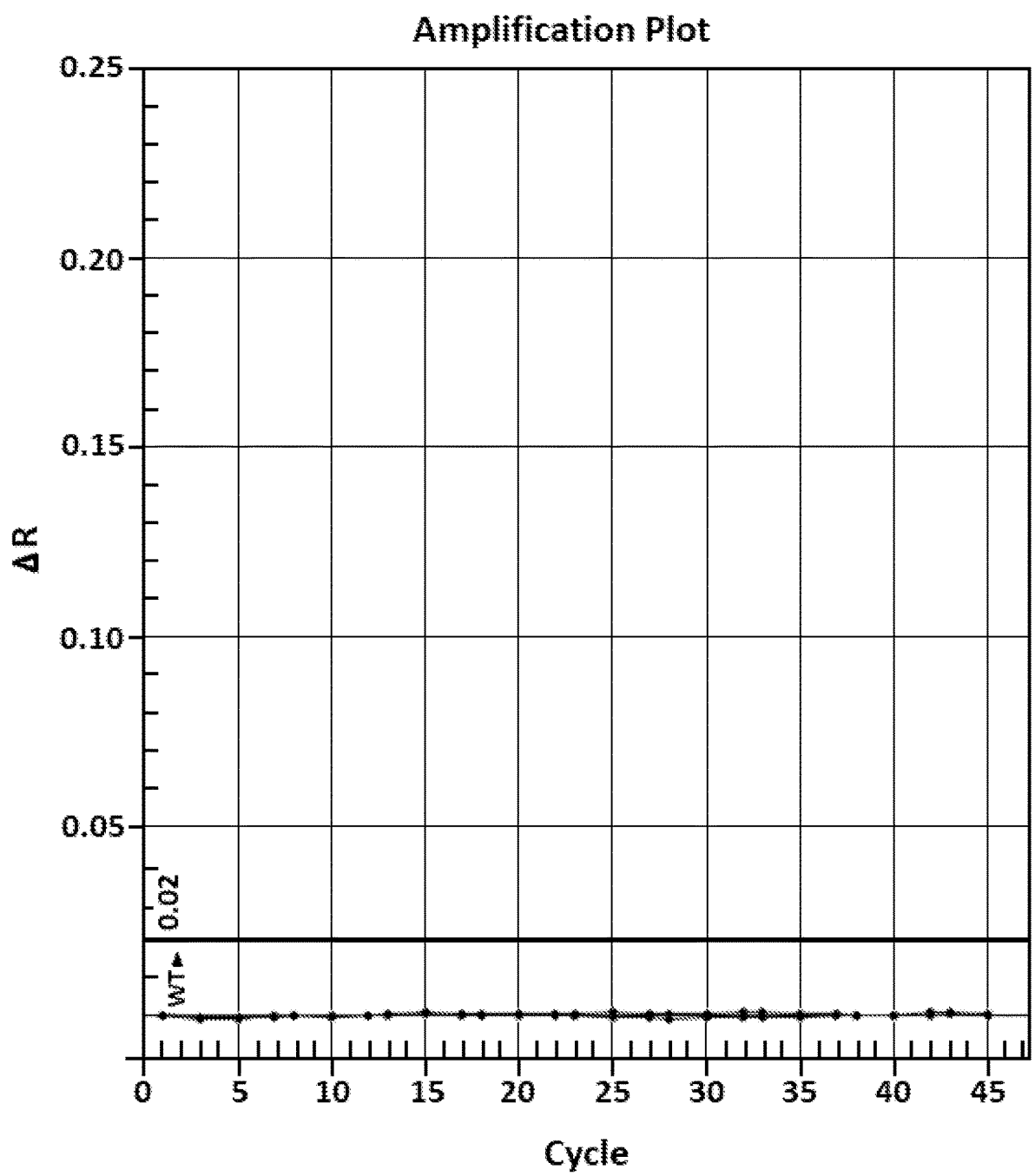
Figure 1V:
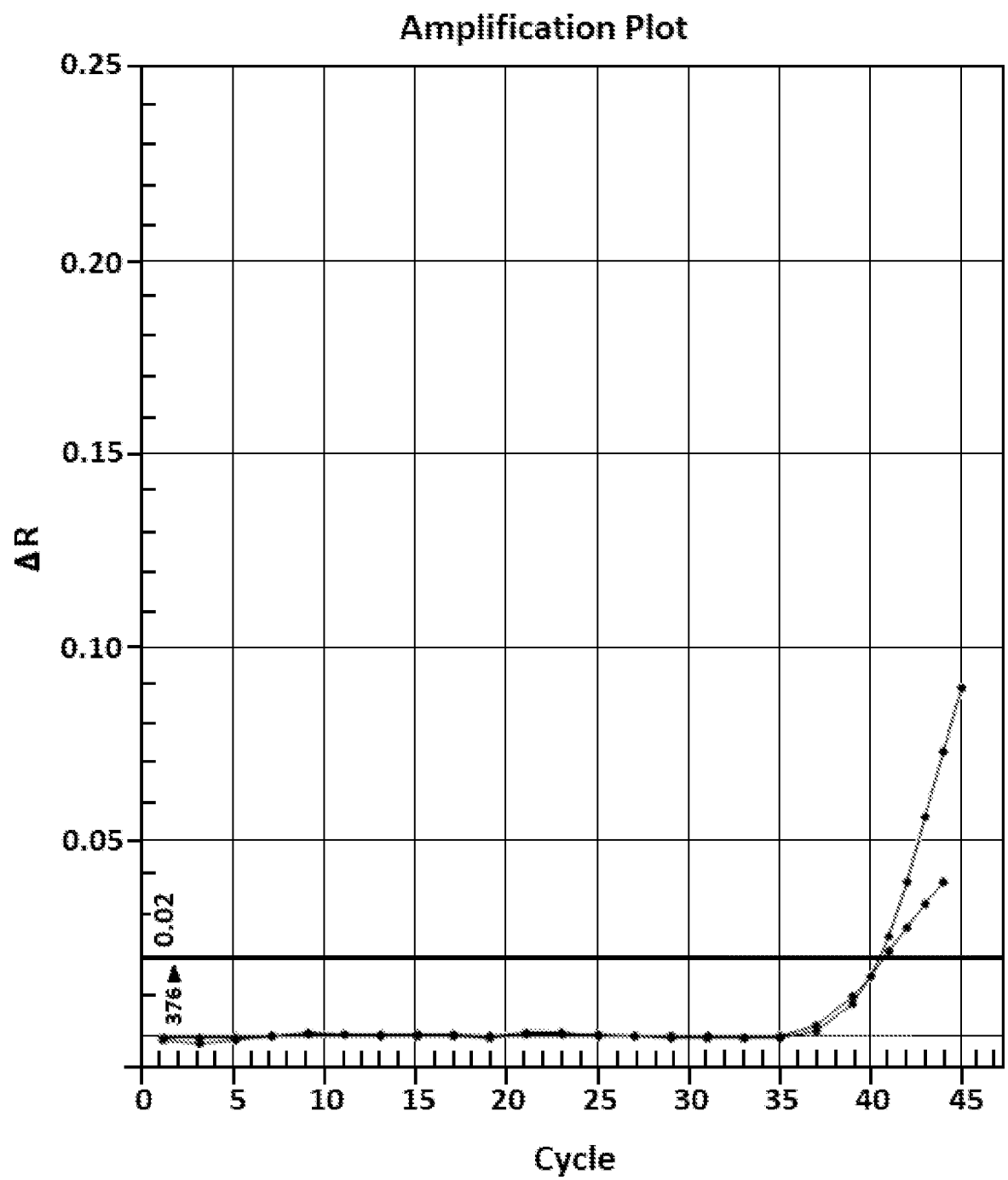
Figure 1W:
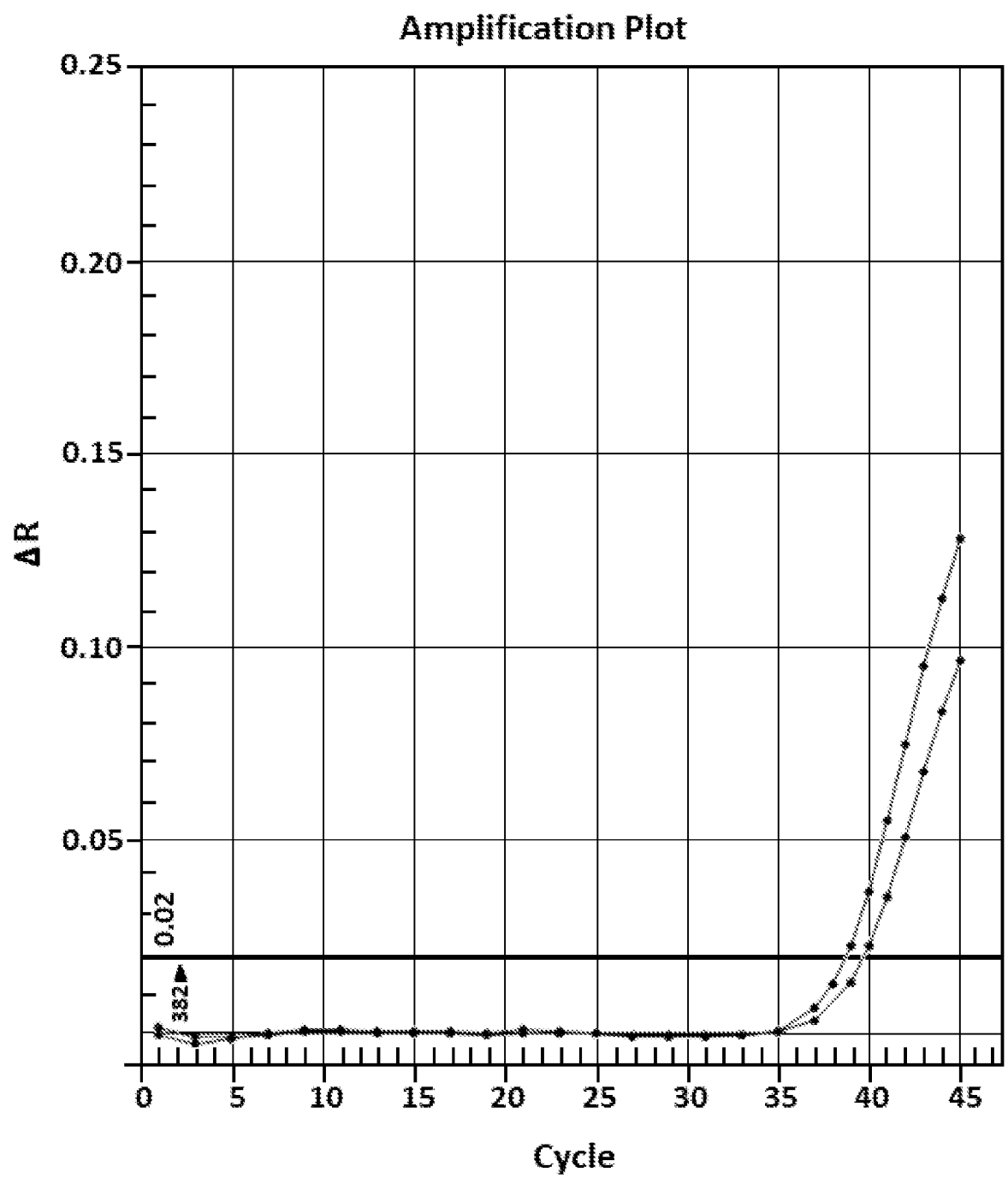
Figure 1X:
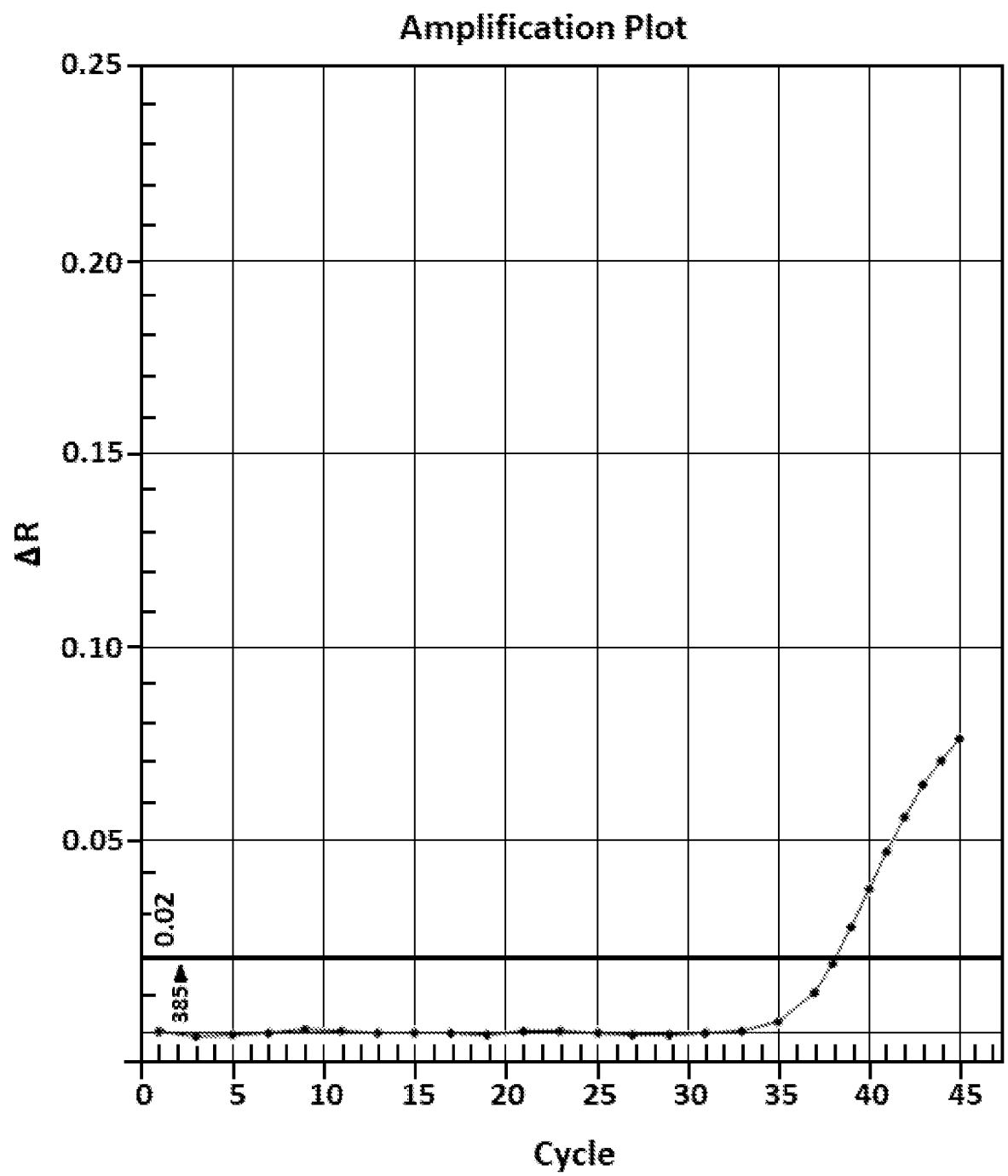
Figure 1Y:
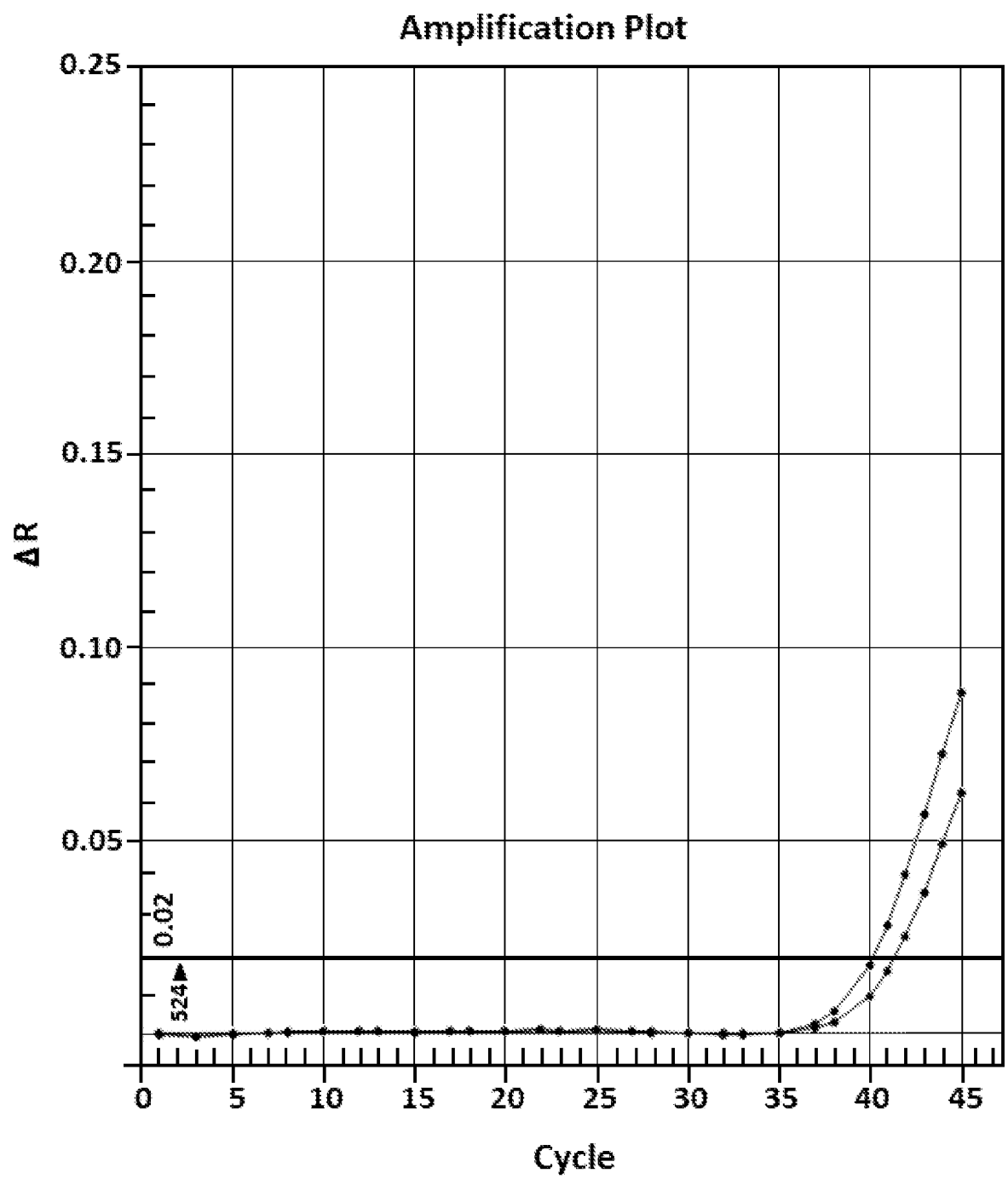
Figure 1Z:
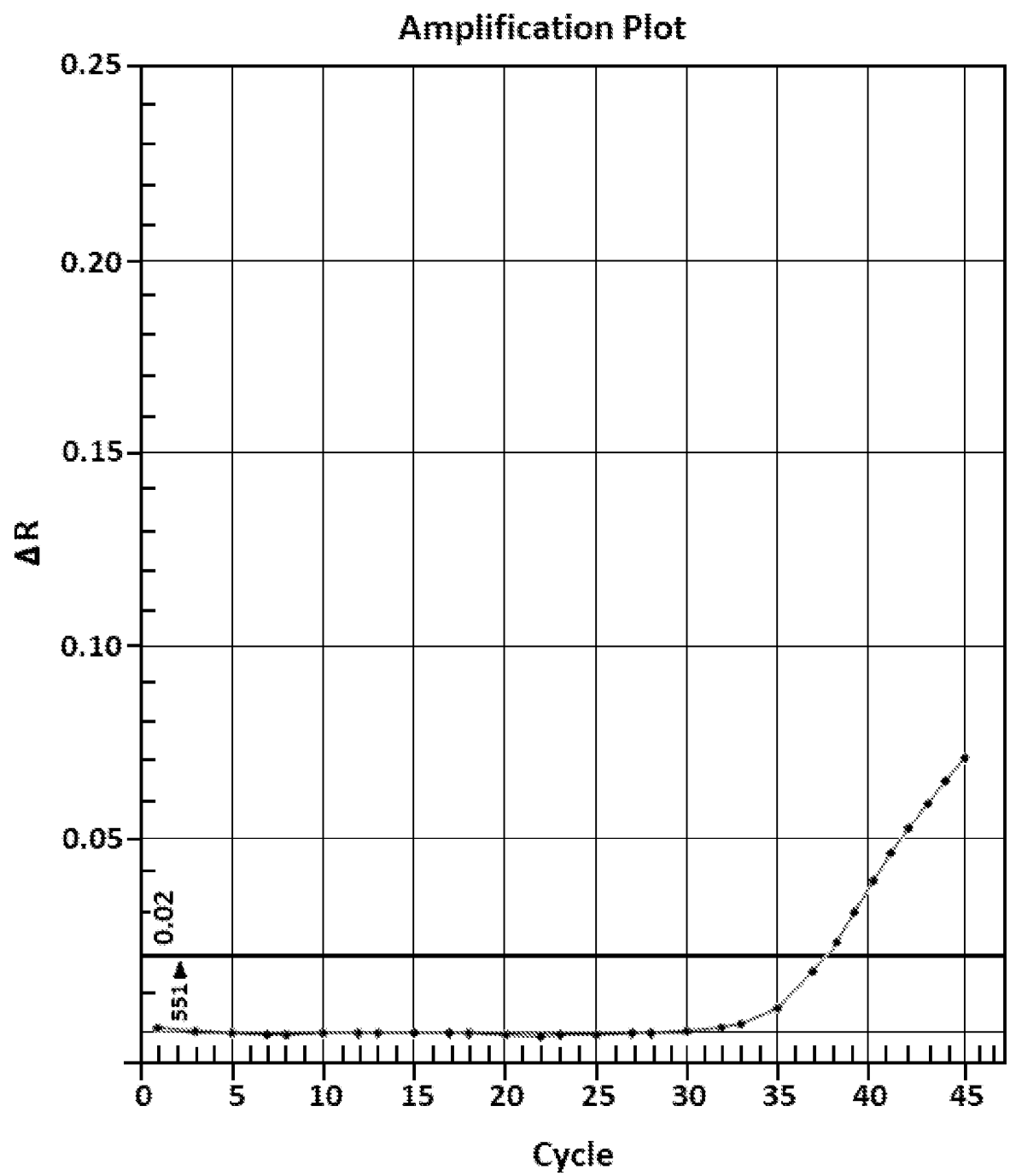
Figure 1A:
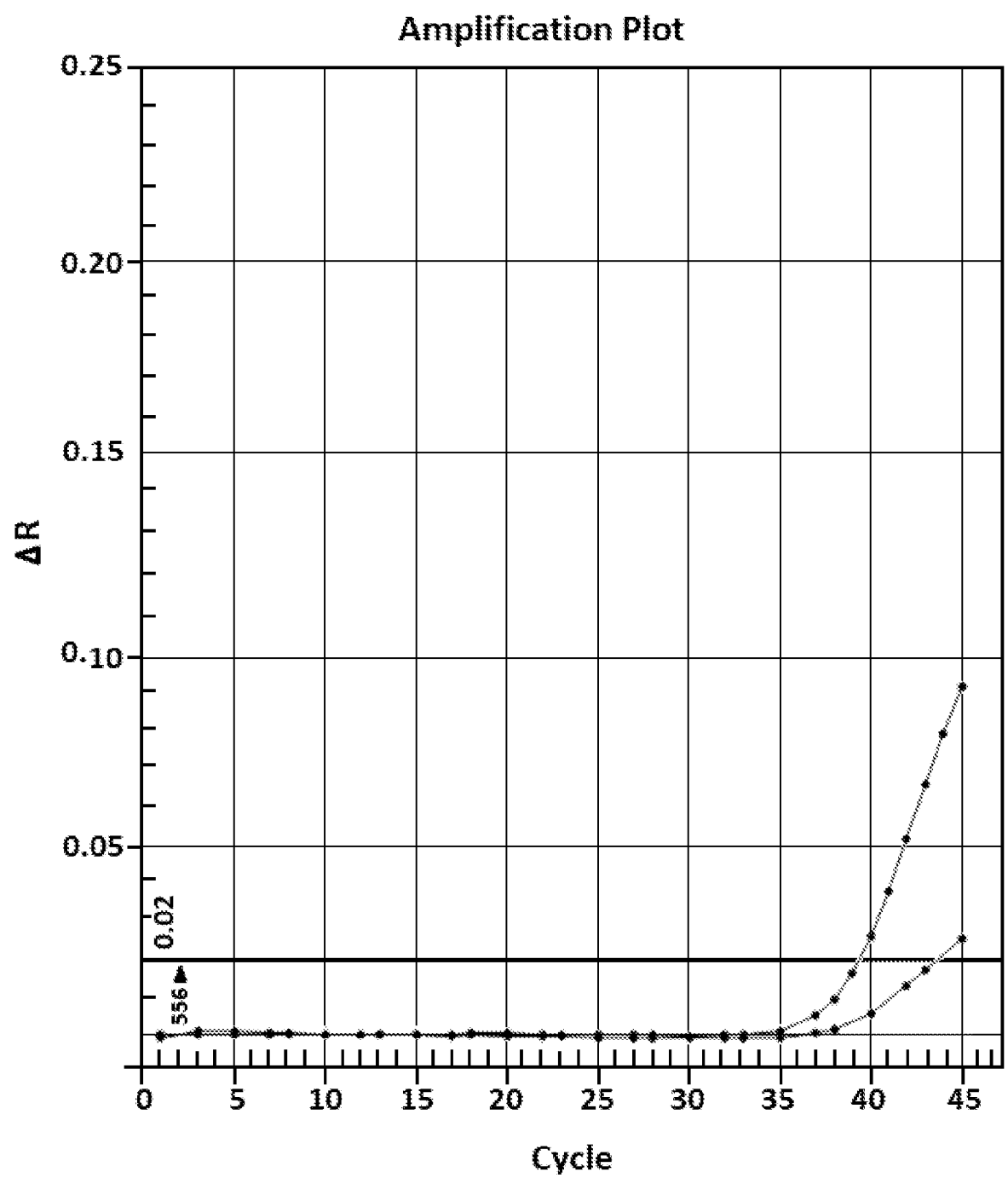
Figure 1B:
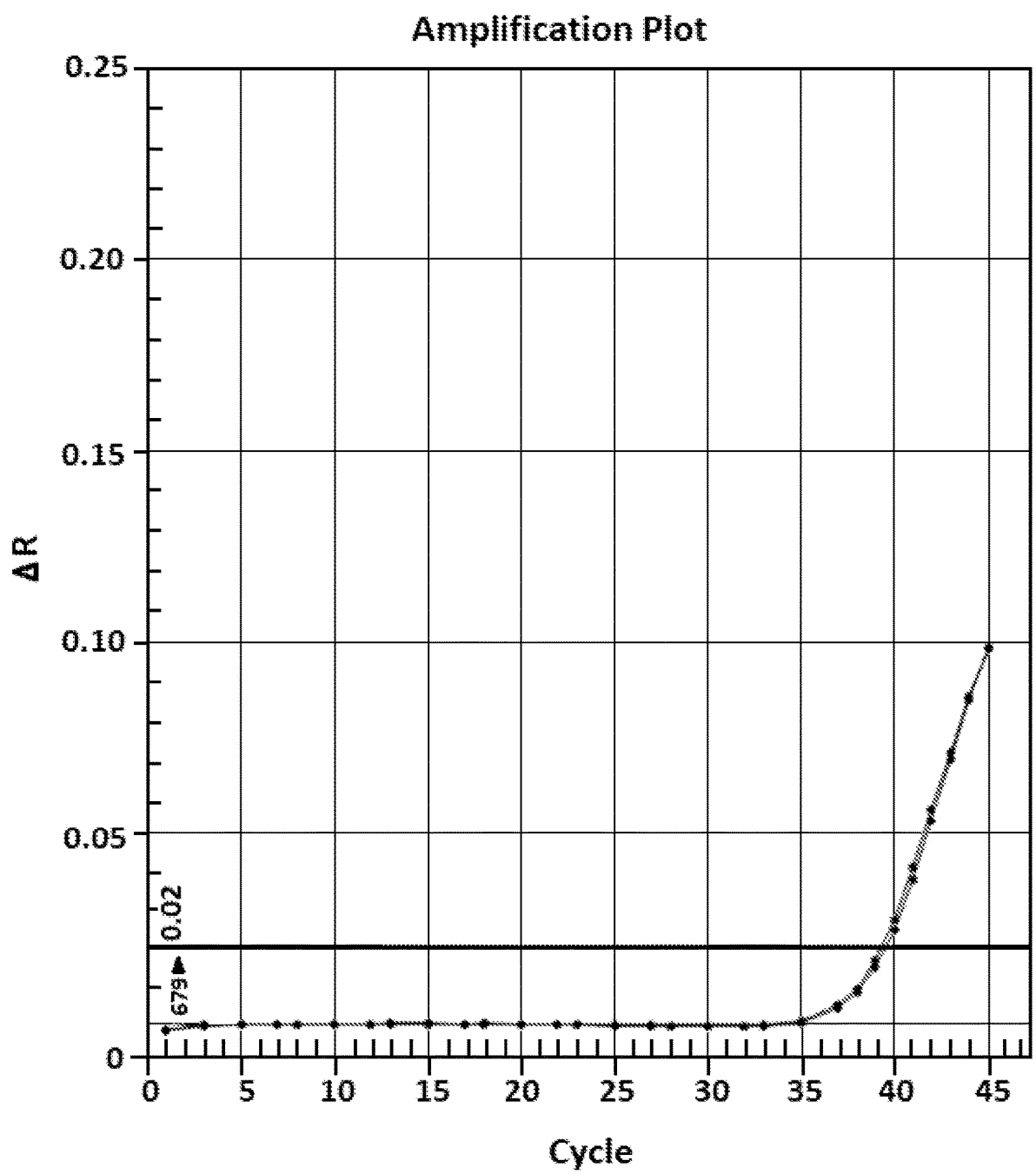
Figure 1C:
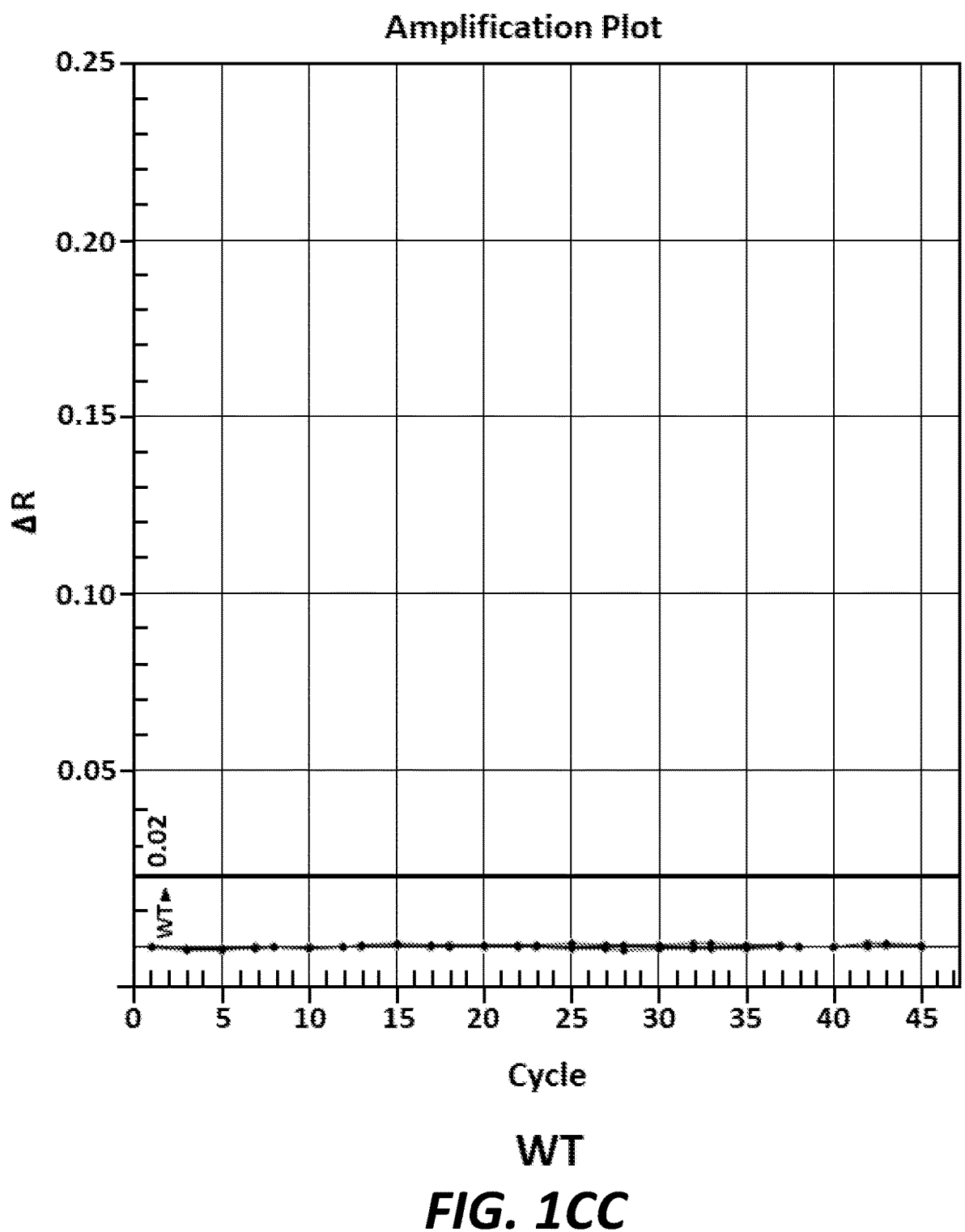
Figure 1D:
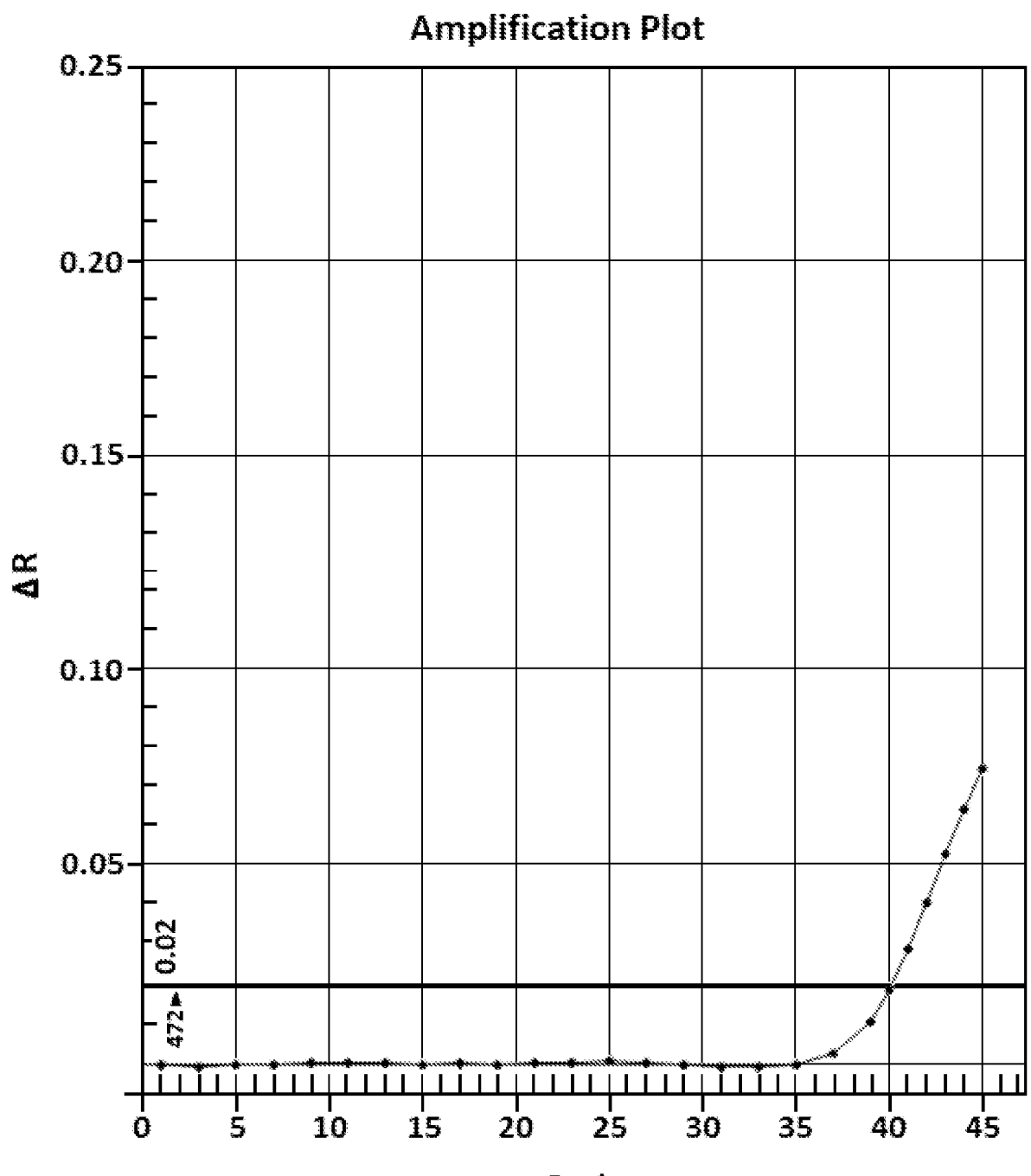
Figure 1E:
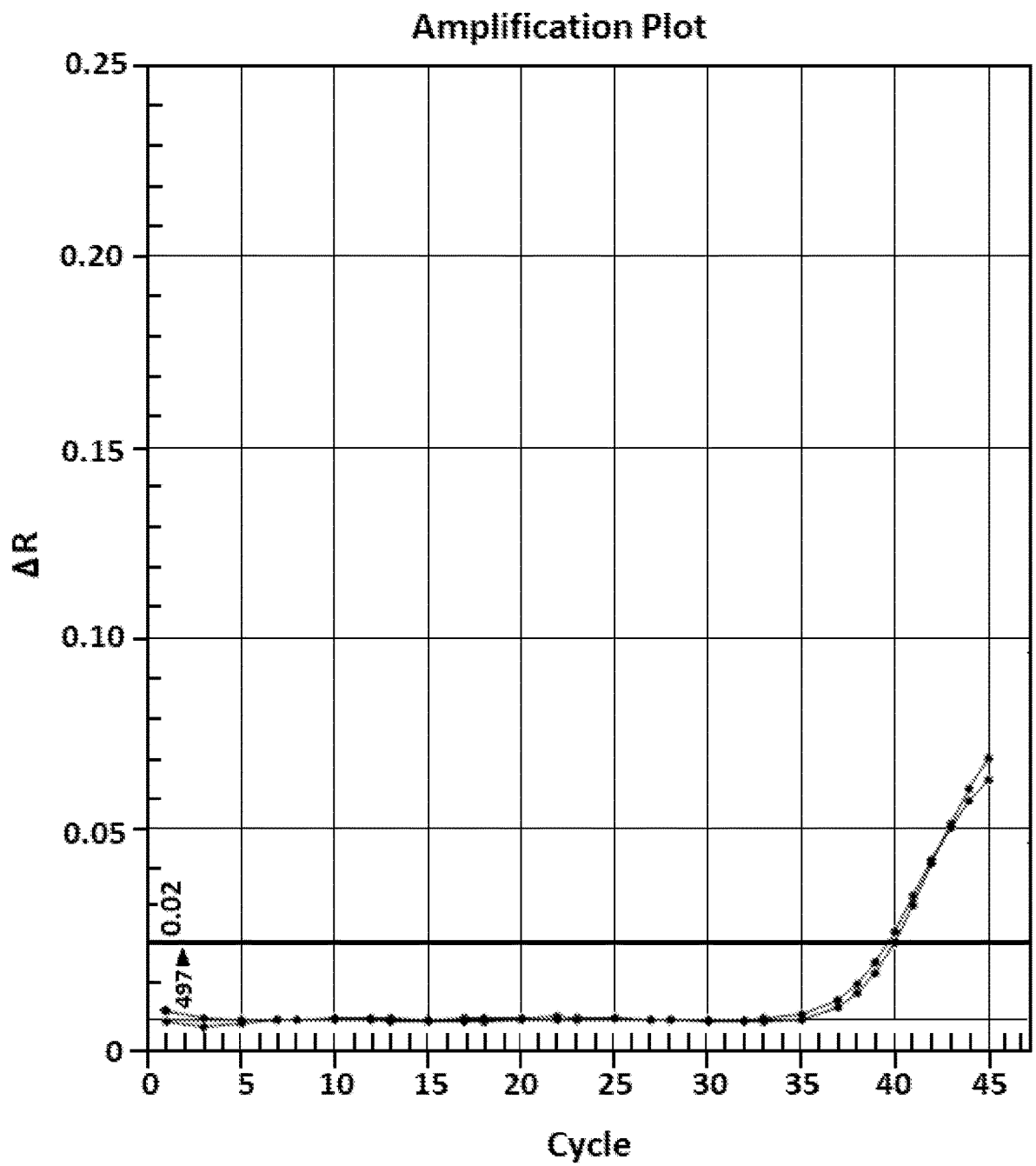
Figure 1F:
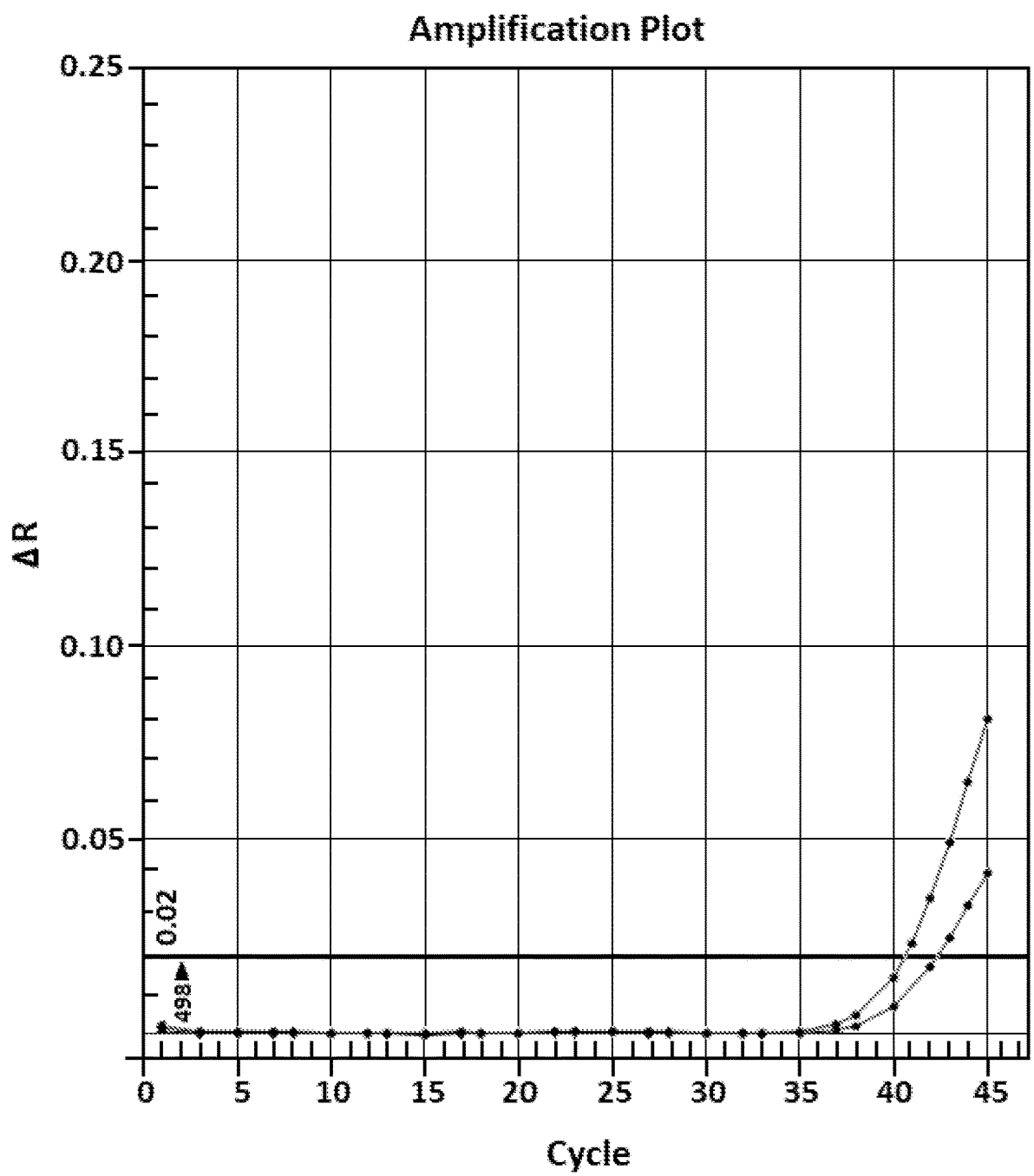
Figure 1G:
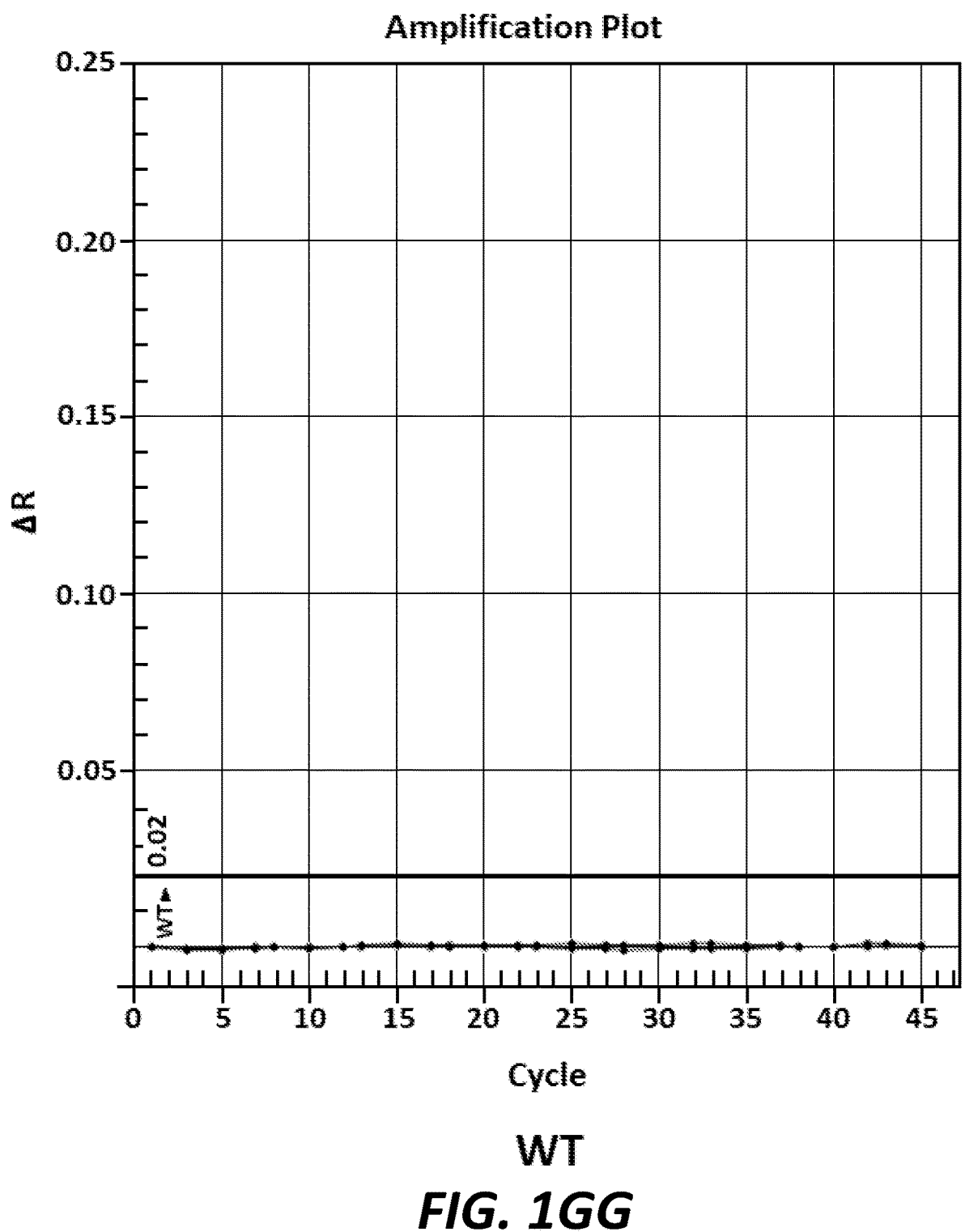
Figure 1H:
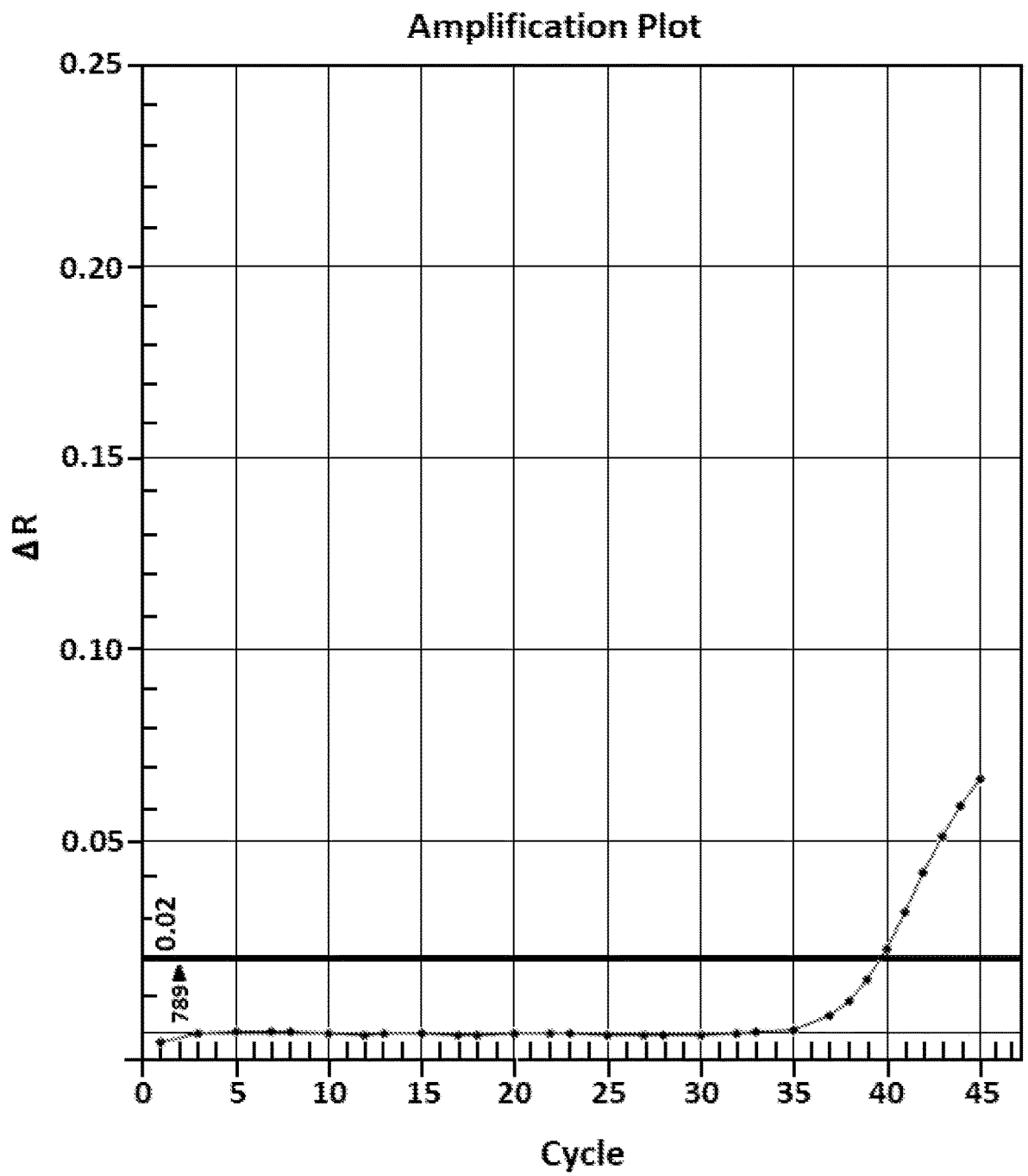
Figure 1I:
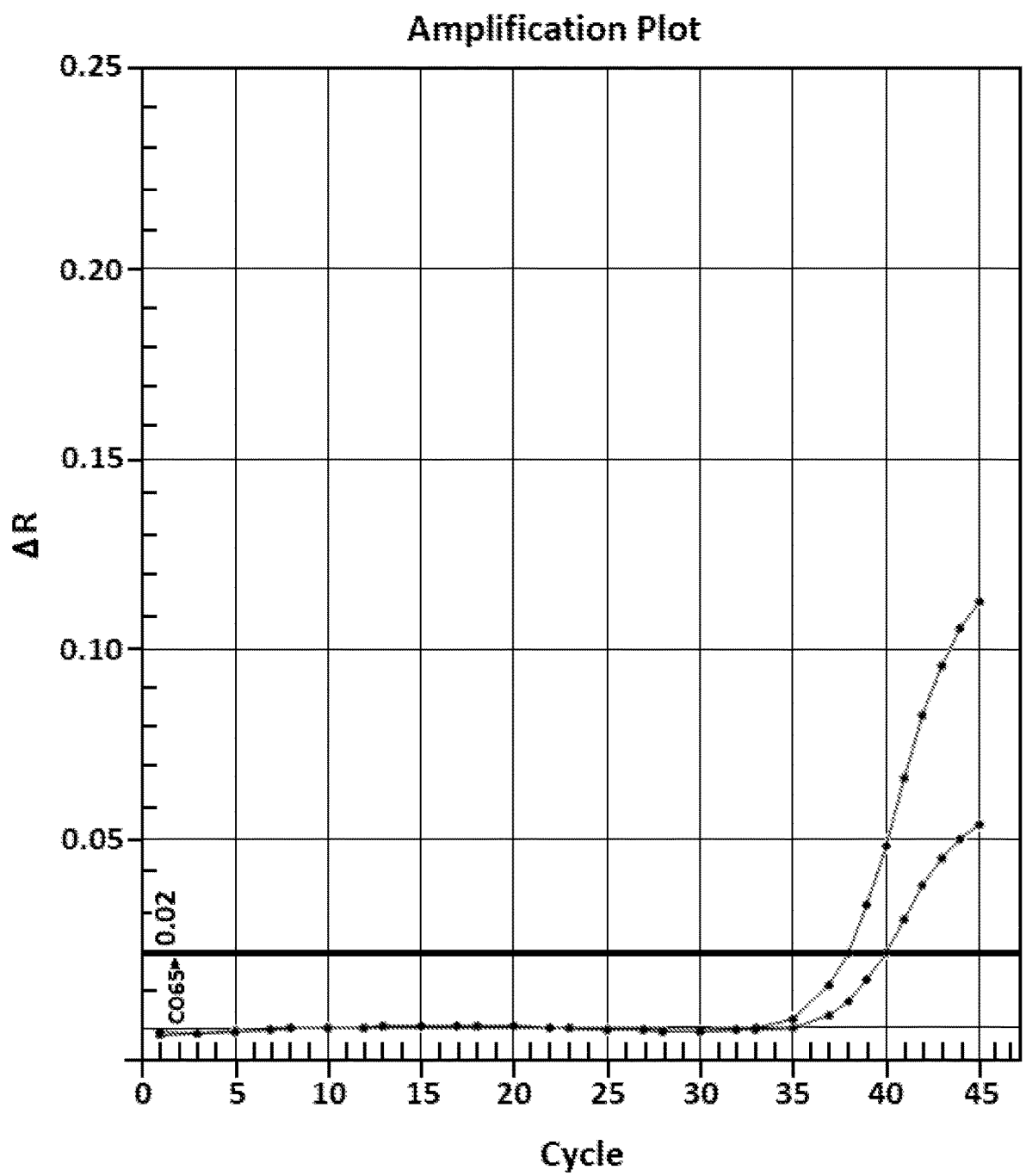

Results are shown in FIGS. 1A to 1II. The wild-type result (WT) is included with each panel, showing that it does not display significant signal. The mutants identified that generated significant signal are the following: V62S, V64S, A70F, F73A, A77F, P253G, E255K, D257R, A259F, A271F, L288S, E289K, S357I, L361S, L376S, P382G, T385I, G418P, R419D, E421K, L461S, A472F, E497K, L498S, E524K, D551R, R556D, S679I, L789S, E189K/E507K/ E742K. The DNA and protein sequence of each of these mutants are in the sequence listing (see sequence listing guide above).

All patents, applications and references above are hereby incorporated by reference. The specific processes, methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A mutant Taq DNA polymerase comprising an amino acid sequence substantially identical to wild type Taq DNA polymerase but having one of the following mutations and amino acid sequences, and wherein said substantially identical amino acid sequence does not include the 6-membered histidine tag at the C-terminus and the six immediately preceding Glycine and Serine amino acids included in each of the following amino acid sequences, and thus differs from wild type Taq DNA polymerase only at the single indicated mutation site: V62S (SEQ ID NO: 4), V64S (SEQ ID NO: 6), A70F (SEQ ID NO: 8), F73A (SEQ ID NO: 10), P253G (SEQ ID NO: 14), E255K (SEQ ID NO: 16), D257R (SEQ ID NO: 18), A259F (SEQ ID NO: 20), A271F (SEQ ID NO: 22), L288S (SEQ ID NO: 24), E289K (SEQ ID NO: 26), S357I (SEQ ID NO: 28), L361S (SEQ ID NO: 30), L376S (SEQ ID NO: 32), P382G (SEQ ID NO: 34), T385I (SEQ ID NO: 36), G418P (SEQ ID NO: 38), R419D (SEQ ID NO: 40), E421K (SEQ ID NO: 42), L461S (SEQ ID NO: 44), A472F (SEQ ID NO: 46), E497K (SEQ ID NO: 48), L498S (SEQ ID NO: 50), E524K (SEQ ID NO: 52), D551R (SEQ ID NO: 54), R556D (SEQ ID NO: 56), S679I (SEQ ID NO: 58), L789S (SEQ ID NO: 60), E189K/E507K/E742K (SEQ ID NO: 62).

2. The mutant Taq DNA polymerase of claim 1 wherein the mutant Taq polymerase is capable of extending a primer where the extension conditions are limited to one second.

3. The mutant Taq DNA polymerase of claim 1 wherein when the extension temperature is 60° C. for 1 second, detectable fluorescent signal is generated in qPCR.

4. A kit for use in qPCR for a sample, comprising an amino acid sequence substantially identical to wild type Taq DNA polymerase but having one of the following mutations and amino acid sequences, and wherein said substantially identical amino acid sequence does not include the 6-membered histidine tag at the C-terminus and the six immediately preceding Glycine and Serine amino acids included in each of the following amino acid sequences, and thus differs from wild type Taq DNA polymerase only at the single indicated mutation site: V62S (SEQ ID NO: 4), V64S (SEQ ID NO: 6), A70F (SEQ ID NO: 8), F73A (SEQ ID NO: 10), P253G (SEQ ID NO: 14), E255K (SEQ ID NO: 16), D257R (SEQ ID NO: 18), A259F (SEQ ID NO: 20), A271F (SEQ ID NO: 22), L288S (SEQ ID NO: 24), E289K (SEQ ID NO: 26), S357I (SEQ ID NO: 28), L361S (SEQ ID NO: 30), L376S (SEQ ID NO: 32), P382G (SEQ ID NO: 34), T385I (SEQ ID NO: 36), G418P (SEQ ID NO: 38), R419D (SEQ ID NO: 40), E421K (SEQ ID NO: 42), L461S (SEQ ID NO: 44), A472F (SEQ ID NO: 46), E497K (SEQ ID NO: 48), L498S (SEQ ID NO: 50), E524K (SEQ ID NO: 52), D551R (SEQ ID NO: 54), R556D (SEQ ID NO: 56), S679I (SEQ ID NO: 58), L789S (SEQ ID NO: 60), E189K/E507K/E742K (SEQ ID NO: 62).

5. The kit of claim 4 further including an intercalating dye.

6. The kit of claim 5 wherein the intercalating dye is SYBR Green or EvaGreen.

* * * * *